US008211635B2

(12) United States Patent
Barton

(10) Patent No.: US 8,211,635 B2
(45) Date of Patent: Jul. 3, 2012

(54) P53 MODULATOR AND CANCER TARGET

(75) Inventor: Michelle Barton, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/667,314

(22) PCT Filed: Jul. 3, 2008

(86) PCT No.: PCT/IB2008/002504
§ 371 (c)(1),
(2), (4) Date: Mar. 5, 2010

(87) PCT Pub. No.: WO2009/004484
PCT Pub. Date: Jan. 8, 2009

(65) Prior Publication Data
US 2010/0189725 A1 Jul. 29, 2010

Related U.S. Application Data

(60) Provisional application No. 60/947,863, filed on Jul. 3, 2007.

(30) Foreign Application Priority Data

Nov. 27, 2007 (GB) .................................. 0723246.5

(51) Int. Cl.
*C12Q 1/68* (2006.01)
(52) U.S. Cl. .............................. 435/6; 435/325; 435/375
(58) Field of Classification Search .......................... None
See application file for complete search history.

(56) References Cited

U.S. PATENT DOCUMENTS

2002/0031818 A1* 3/2002 Ronai et al. .................... 435/226

FOREIGN PATENT DOCUMENTS

| JP | 2005-000056 | 1/2005 |
|---|---|---|
| WO | 02/44427 | 6/2002 |
| WO | 2004/043371 | 5/2004 |
| WO | 2007/041213 | 4/2007 |

OTHER PUBLICATIONS

Wang et al. (EMBO Journal 2005, 24:3279-3290).*
Yaun et al. (Molecular Cell 2005, 19:77-87).*
Meroni et al. (BioEssays 2005, 27L1147-1157).*
El-Deiry, W.S. et al., "Toplogical Control of p21WAF1/CIPI Expression in Normal and Neoplastic Tissues" Cancer Research, 55:2910-2919 (Jul. 1, 1995).
Fraser, R.A. et al., "The Putative Cofactor TIF1α Is a Protein Kinase That Is Hyperphosphorylated upon Interaction with Llganded Nuclear Receptors" The Journal of Biochemistry, 273(26):16199-16204 (1998).
Friedman, J.R. et al., "KAP-1, a novel corepressor for the highly conserved KRAB repression domain" Genes & Development, 10:2067-2078 (1996).
Gack, M.U. et al., "TRIM25 RING-finger E3 ubiquitin ligase is essential for RIG-I-mediated antiviral activity" Nature, 446:916-920 (Apr. 19, 2007).
Haupt, Y. et al., "Mdm2 promotes the rapid degradation of p53" Nature, 387:296-299 (May 15, 1997).
Honda, R. et al., "Oncoprotein MDM2 is a ubiquitin ligase E3 for tumor suppressor p53" FEBS Letters, 420:25-27 (1997).
International Search Report and Written Opinion, Application No. PCT/IB2008/002504, mailed Jul. 7, 2009 (18 pages).
Jacobson, R.H. et al., "Structure and Function of a Human TAFII250 Double Bromodomain Module" Science, 288(5470):1422-1425 (May 26, 2000).
Kim, S. et al., "A novel member of the Ring finger family, KRIP-1 associates with the KRAB-A transcriptional repressor domain of zinc finger proteins" Proc. Natl. Acad. Sci. USA, 93:15299-15304 (Dec. 1996).
Kubbutat, M.H.G. et al., "Regulation of p53 stability by Mdm2" Nature, 387:299-303 (May 15, 1997).
Le Douarin, B. et al., "The N-terminal part of TIF1, a putative mediator of the ligand-dependent activation function (AF-2) of nuclear receptors, is fused to B-raf in the oncogenic protein T18" The EMBO Journal, 14(9): 2020-2033 (1995).
Le Douarin, B. et al., "A possible involvement of TIF1α and TIF1β in the epigenetic control of transcription by nuclear receptors" The EMBO Journal, 15(23):6701-6715 (1996).
Levine A.J., "p53, the Cellular Gatekeeper for Growth and Division" Cell, 88(3):323-331 (Feb. 7, 1997).
Lin, T. et al., "p53 induces differentiation of mouse embryonic stem cells by suppressing Nanog expression" Nature Cell Biology, 7(2):165-171 (Feb. 2005).
Martin, D.G.E. et al., "The Yng1p Plant Homeodomain Finger Is a Methyl-Histone Binding Module That Recognizes Lysine 4-Methylated Histone H3" Molecular and Cellular Biology, 26(21):7871-7879 (Nov. 2006).
Miyashita, T. et al., "Tumor Suppressor p53 Is a Direct Transcriptional Activator of the Human bax Gene" Cell, 80(2):293-299 (1995).
Momand, J. et al., "The mdm-2 Oncogene Product Forms a Complex with the p53 Protein and Inhibits p53-Mediated Transactivation" Cell, 69(7):1237-1245 (1992).
Moosmann, P. et al., "Transcriptional repression by RING finger protein TIF1β that interacts with the KRAB repressor domain of KOX1" Nucleic Acids Research, 24(24):4859-4867 (1996).
Qin, H. et al., "Regulation of Apoptosis and Differentiation by p53 in Human Embryonic Stem Cells" The Journal of Biological Chemistry, 282(8):5842-5852 (Feb. 23, 2007).

(Continued)

*Primary Examiner* — Kimberly Chong
(74) *Attorney, Agent, or Firm* — Fulbright & Jaworski L.L.P.

(57) ABSTRACT

Methods of screening for modulators of TRIM24 (also known as TIF1-ALPHA) expression and/or biological activity are described. In particular, methods of screening of screening for modulators of TRIM24 E3 ligase activity, and specifically an E3 ligase activity directed at p53 as the target polypeptide are also described. Modulators of TRIM24 expression and activity are provided and their use in treatment of cancer, particularly in breast, colon, prostate, renal cancers and in acute lymphoblastic leukaemia. Suitable modulators of TRIM24 expression include siRNA and shRNA and can be used in the treatment of cancer and for targeting cancer stem cells.

7 Claims, 25 Drawing Sheets

OTHER PUBLICATIONS

Seeler, J.S. et al., "Common Properties of Nuclear Body Protein SP100 and TIF1α Chromatin Factor: Role of SUMO Modification" Molecular and Cellular Boilogy, 21(10):3314-3324 (May 2001).

Sripathy, S.P. et al., "The KAP1 Corepressor Functions to Coordinate the Assembly De Novo HP1-Demarcated Microenvironments of Heterochromatin Required for KRAB Zinc Finger Protein-Mediated Transcriptional Repression" Molecular and Cellular Boilogy, 26(22):8623-8638 (Nov. 2006).

Thénot, S. et al., "Differential Interaction of Nuclear Receptors with the Putative Human Transcriptional Coactivator hTIF1" The Journal of Biological Chemistry, 272(18):12062-12068 (May 2, 1997).

Torres-Padilla, M.E. et al., "Role of TIF1α as a modulator of embryonic transcription in the mouse zygote" The Journal of Biological Chemistry, 174(3):329-338 (Jul. 31, 2006).

UK Intellectual Property Office Search Report received in Application No. GB0723246.5, dated Mar. 4, 2008 (3 pages).

Ventura, A. et al., "Restoration of p53 function leads to tumour regression in vivo" Nature, 445(7128):661-665 (Feb. 8, 2007).

Vichi, A. et al., E3 ubiquitin ligase activity of the trifunctional ARD1 (ADP-ribosylation factor domain protein 1) Proc. Natl. Acad. Sci. USA, 102(6):1945-1950 (Feb. 8, 2005).

Xirodimas, D.P. et al., "Mdm2-Mediated NEDD8 Conjugation of p53 Inhibits Its Transcriptional Activity" Cell, 118: 83-97 (Jul. 9, 2004).

Xue, W. et al., "Senescence and tumour clearance is triggered by p53 restoration in murine liver carcinomas" Nature, 445(7128):656-660 (Feb. 8, 2007).

Yang, Y. et al., "Regulating the p53 system through ubiquitination" Oncogene, 23:2096-2106 (2004).

* cited by examiner

| | | | | | |
|---|---|---|---|---|---|
| 1 | gacagatacc | ctccttccgg | ccgcgccact | cgggaggcgg | atcccgtggg | cctgaggagg |
| 61 | cttcccccgc | ccggtttgct | ttccctccct | cgctggcgct | gccgcgagtc | caccgagcgg |
| 121 | cctctgagga | gcagccgcag | gaggaggagg | aggtcgtcgg | gggcggcggg | cggagaccgc |
| 181 | gctctcgctt | ccccggcggc | ggcaagggca | ggacaatgga | ggtggcggtg | gagaaggcgg |
| 241 | tggcggcggc | ggcagcggcc | tcggctgcgg | cctccggggg | gccctcggcg | gcgccgagcg |
| 301 | gggagaacga | ggccgagagt | cggcagggcc | cggactcgga | gcgcggcggc | gaggcggccc |
| 361 | ggctcaacct | gttggacact | tgcgccgtgt | gccaccagaa | catccagagc | cgggcgccca |
| 421 | agctgctgcc | ctgcctgcac | tctttctgcc | agcgctgcct | gcccgcgccc | cagcgctacc |
| 481 | tcatgctgcc | cgcgcccatg | ctgggctcgg | ccgagacccc | gccaccgtc | cctgccccg |
| 541 | gctcgccggt | cagcggctcg | tcgccgttcg | ccacccaagt | tggagtcatt | cgttgcccag |
| 601 | tttgcagcca | agaatgtgca | gagagacaca | tcatagataa | cttttttgtg | aaggacacta |
| 661 | ctgaggttcc | cagcagtaca | gtgaaaaagt | caaatcaggt | atgtacaagc | tgtgaggaca |
| 721 | acgcagaagc | caatgggttt | tgtgtagagt | gtgttgaatg | gctctgcaag | acgtgtatca |
| 781 | gagctcatca | gagggtaaag | ttcacaaaag | accacactgt | cagacagaaa | gaggaagtat |
| 841 | ctccagaggc | agttggtgtc | accagccagc | gaccagtgtt | ttgtcctttt | cataaaaagg |
| 901 | agcagctgaa | gctgtactgt | gagacatgtg | acaaactgac | atgtcgagac | tgtcagttgt |
| 961 | tagaacataa | agagcataga | taccaattta | tagaagaagc | ttttcagaat | cagaaagtga |
| 1021 | tcatagatac | actaatcacc | aaactgatgg | aaaaaacaaa | atacataaaa | ttcacaggaa |
| 1081 | atcagatcca | aaacagaatt | attgaagtaa | atcaaaatca | aagcaggtg | gaacaggata |
| 1141 | ttaaagttgc | tatatttaca | ctgatggtag | aaataaataa | aaaaggaaaa | gctctactgc |
| 1201 | atcagttaga | gagccttgca | aaggaccatc | gcatgaaact | tatgcaacaa | caacaggaag |
| 1261 | tggctggact | ctctaaacaa | ttggagcatg | tcatgcattt | ttctaaatgg | gcagtttcca |
| 1321 | gtggcagcag | tacagcatta | ctttatagca | aacgactgat | tacataccgg | ttacggcacc |
| 1381 | tccttcgtgc | aaggtgtgat | gcatcccag | tgaccaacaa | caccatccaa | tttcactgtg |
| 1441 | atcctagttt | ctgggctcaa | atatcatca | acttaggttc | tttagtaatc | gaggataaag |
| 1501 | agagccagcc | acaaatgcct | aagcagaatc | ctgtcgtgga | acagaattca | cagccaccaa |
| 1561 | gtggtttatc | atcaaaccag | ttatccaagt | tcccaacaca | gatcagccta | gctcaattac |
| 1621 | ggctccagca | tatgcagcaa | cag<u>gtaatgg</u> | <u>ctcagaggca</u> | <u>acaggtgcaa</u> | <u>cggaggccag</u> |
| 1681 | <u>cacctgtggg</u> | <u>tttaccaaac</u> | <u>cctagaatgc</u> | <u>aggggcccat</u> | <u>ccagcaacct</u> | <u>tccatctctc</u> |
| 1741 | <u>atcagcaacc</u> | gcctccacgt | tgataaact | ttcagaatca | cagccccaaa | cccaatggac |
| 1801 | cagttcttcc | tcctcatcct | caacaactga | gatatccacc | aaaccagaac | ataccacgac |
| 1861 | aagcaataaa | gccaaacccc | ctacagatgg | cttcttggc | tcaacaagcc | ataaaacagt |
| 1921 | ggcagatcag | cagtggacag | gaaccccat | caactaccaa | cagcacatcc | tctactcctt |
| 1981 | ccagccccac | gattactagt | gcagcaggat | atgatggaaa | ggcttttggt | tcacctatga |
| 2041 | tcgatttgag | ctcaccagtg | ggagggtctt | ataatcttcc | ctctcttccg | gatattgact |
| 2101 | gttcaagtac | tattatgctg | gacaatattg | tgaggaaaga | tactaatata | gatcatggcc |
| 2161 | agccaagacc | accctcaaac | agaacggtcc | agtcaccaaa | ttcatcagtg | ccatctccag |
| 2221 | gccttgcagg | acctgttact | atgactagtg | tacacccccc | aatacgttca | cctagtgcct |
| 2281 | ccagcgttgg | aagccgagga | agctctggct | cttccagcaa | accagcagga | gctgactcta |
| 2341 | cacacaaagt | cccagtggtc | atgctggagc | caattcgaat | aaaacaagaa | aacagtggac |
| 2401 | caccggaaaa | ttatgatttc | cctgttgtta | tagtgaagca | agaatcagat | gaagaatcta |
| 2461 | ggcctcaaa | tgccaattat | ccaagaagca | tactcacctc | cctgctctta | aatagcagtc |
| 2521 | agagctctac | ttctgaggag | actgtgctaa | gatcagatgc | ccctgatagt | acaggagatc |
| 2581 | aacctggact | tcaccaggac | aattcctcaa | atggaaagtc | tgaatggttg | gatccttccc |
| 2641 | agaagtcacc | tcttcatgtt | ggagagacaa | ggaagagga | tgacccaat | gaggactggt |
| 2701 | gtgcagtttg | tcaaaacgga | ggggaactcc | tctgctgtga | aagtgcccc | aaagtattcc |
| 2761 | atctttcttg | tcatgtgccc | acattgacaa | attttccaag | tggagagtgg | atttgcactt |
| 2821 | tctgccgaga | cttatctaaa | ccagaagttg | aatatgattg | tgatgctccc | agtcacaact |
| 2881 | cagaaaaaaa | gaaaactgaa | ggccttgtta | agttaacacc | tatagataaa | aggaagtgtg |
| 2941 | agcgcctact | tttatttctt | tactgccatg | aaatgagcct | ggcttttcaa | gacctgttc |
| 3001 | ctctaactgt | gcctgattat | tacaaaataa | ttaaaaatcc | aatggatttg | tcaaccatca |
| 3061 | agaaaagact | acaagaagat | tattccatgt | actcaaaacc | tgaagatttt | gtagctgatt |
| 3121 | ttagattgat | ctttcaaaac | tgtgctgaat | tcaatgagcc | tgattcagaa | gtagccaatg |
| 3181 | ctggtataaa | acttgaaaat | tattttgaag | aacttctaaa | gaacctctat | ccagaaaaaa |
| 3241 | ggtttcccaa | accagaattc | aggaatgaat | cagaagataa | taaatttagt | gatgattcag |

FIG. 1A

```
3301  atgatgactt  tgtacagccc  cggaagaaac  gcctcaaaag  cattgaagaa  cgccagttgc
3361  ttaaataata  tgcagcacca  ctagcttgtg  ctggttttta  gattttttg   ttttcaaaaa
3421  aacatttgtc  agtaatttaa  catcactaca  aaaagaagag  tttgtgacta  ttctcatctc
3481  tgttttggac  gtttactaga  ctttgatttc  cttaatagcc  catttctgtt  aacctcttat
3541  cactaagaaa  gaaaggaaag  aaggagatga  atagaagaaa  gaaaatggaa  agaaggaaaa
3601  aaggaggata  gaaaaaggat  ggaagaaaga  agcattgaaa  acaaagacat  tcttcccact
3661  tcttggattt  ttaaaccaca  gtctggagtg  atagctactg  tagaaaggaa  atagactttg
3721  tatgaactct  ttaagttgaa  aagtaaaaaa  tatatgtggt  ttggatgtgt  gctttaattc
3781  agctttagaa  attaatacca  ctaccgtga   attatatggc  ctgacaatat  gaattaggtg
3841  tactgtactg  aagaacagta  ctccacaaac  atgggtggta  acaagagttc  catcccagga
3901  ggccaaacgg  tgcaacagaa  gggtaggtta  gatgctatta  agaaggcact  taatagtaca
3961  tcatgtaaga  tggcaactgt  attaaagaaa  aatccggaaa  acaaaaa
```

MEVAVEKAVAAAAAASAAASGGPSAAPSGENEAESRQGPDSERGGEAARL
NLLDTCAVCHQNIQSRAPKLLPCLHSFCQRCLPAPQRYLMLPAPMLGSAE
TPPPVPAPGSPVSGSSPFATQVGVIRCPVCSQECAERHIIDNFFVKDTTE
VPSSTVEKSNQVCTSCEDNAEANGFCVECVEWLCKTCIRAHQRVKFTKDH
TVRQKEEVSPEAVGVTSQRPVFCPFHKKEQLKLYCETCDKLTCRDCQLLE
HKEHRYQFIEEAFQNQKVIIDTLITKLMEKTKYIKFTGNQIQNRIIEVNQ
NQKQVEQDIKVAIFTLMVEINKKGKALLHQLESLAKDHRMKLMQQQQEVA
GLSKQLEHVMHFSKWAVSGSSTALLYSKRLITYRLRHLLRARCDASPVT
NNTIQFHCDPSFWAQNIINLGSLVIEDKESQPQMPKQNPVVEQNSQPPSG
LSSNQLSKFPTQISLAQLRLQHMQQQVMAQRQQVQRRPAPVGLPNPRMQG
PIQQPSISHQQPPPRLINFQNHSPKPNGPVLPPHPQQLRYPPNQNIPRQA
IKPNPLQMAFLAQQAIKQWQISSGQGTPSTTNSTSSTPSSPTITSAAGYD
GKAFGSPMIDLSSPVGGSYNLPSLPDIDCSSTIMLDNIVRKDTNIDHGQP
RPPSNRTVQSPNSSVPSPGLAGPVTMTSVHPPIRSPSASSVGSRGSSGSS
SKPAGADSTHKVPVVMLEPIRIKQENSGPPENYDFPVVIVKQESDEESRP
QNANYPRSILTSLLLNSSQSSTSEETVLRSDAPDSTGDQPGLHQDNSSNG
KSEWLDPSQKSPLHVGETRKEDDPNEDWCAVCQNGGELLCCEKCPKVFHL
SCHVPTLTNFPSGEWICTFCRDLSKPEVEYDCDAPSHNSEKKKTEGLVKL
TPIDKRKCERLLLFLYCHEMSLAFQDVPLTVPDYYKIIKNPMDLSTIKK
RLQEDYSMYSKPEDFVADFRLIFQNCAEFNEPDSEVANAGIKLENYFEEL
LKNLYPEKRFPKPEFRNESEDNKFSDDSDDDFVQPRKKRLKSIEERQLLK

```
NM_015905    GACAGATACCCTCCTTCCGGCCGCGCCACTCGGGAGGCGGATCCCGTGGGCCTGAGGAGG  60
NM_003852    GACAGATACCCTCCTTCCGGCCGCGCCACTCGGGAGGCGGATCCCGTGGGCCTGAGGAGG  60
AF009353     ------------------------------------------------------------
BC028689     ------------------------------------------------------------
AF119042     ------------------------------------------------------------
AK127592     ------------------------------------------------------------

NM_015905    CTTCCCCCGCCCGGTTTGCTTTCCCTCCCTCGCTGGCGCTGCCGCGAGTCCACCGAGCGG  120
NM_003852    CTTCCCCCGCCCGGTTTGCTTTCCCTCCCTCGCTGGCGCTGCCGCGAGTCCACCGAGCGG  120
AF009353     ------------------------------------------------------------
BC028689     ------------------------------------------AGCGGGTCCACCGAGCGG  18
AF119042     -----------------------------------------CCGCGAGTCCACCGAGCGG  19
AK127592     ------------------------------------------------------------

NM_015905    CCTCTGAGGAGCAGCCGCAGGAGGAGGAGGAGGTCGTCGGGGGCGGCGGGCGGAGACCG-  179
NM_003852    CCTCTGAGGAGCAGCCGCAGGAGGAGGAGGAGGTCGTCGGGGGCGGCGGGCGGAGACCG-  179
AF009353     ------------------------------------------------------------
BC028689     CCTCTGAGGAGCAGCCGCAGGAGGAGGAGGAGGTCGTCGGGGGCGGCGGGCGGAGACCG-  77
AF119042     CCTCTGAGGAGCAGCCGCAGGAGGAGGAGGAGGTCGTCGGGGGCGGCGGGCGGAGACCGG  79
AK127592     ------------------------------------------------------------

NM_015905    -CGCTCTCGCTTCCCCGGCGGCGGCAAGGGCAGGACAATGGAGGTGGCGGTGGAGAAGGC  238
NM_003852    -CGCTCTCGCTTCCCCGGCGGCGGCAAGGGCAGGACAATGGAGGTGGCGGTGGAGAAGGC  238
AF009353     ---------------------------------ATGGAGGTGGCGGTGGAGAAGGC  23
BC028689     -CGCTCTCGCTTCCCCGGCGGCGGCAAGGGCAGGACAATGGAGGTGGCGGTGGAGAAGGC  136
AF119042     CTCTTCTCGCTTCCCCGGCGGCGGCAAGGGCAGGACAATGGAGGTGGCGGTGGAGAAGGC  139
AK127592     ------------------------------------------------------------

NM_015905    GGTGGCGGCGGCGGCAGCGGCCTCGGCTGCGGCCTCCGGGGGGCCCTCGGCGGCGCCGAG  298
NM_003852    GGTGGCGGCGGCGGCAGCGGCCTCGGCTGCGGCCTCCGGGGGGCCCTCGGCGGCGCCGAG  298
AF009353     GGTGGCGGCGGCGGCA-CGGC-TCGGCTGCG--CTCCGGGGGGCCCTCGG-GGCG----G  74
BC028689     GGTGGCGGCGGCGGCAGCGGCCTCGGCTGCGGCCTCCGGGGGGCCCTCGGCGGCGCCGAG  196
AF119042     GGTGGCGGCGGCGGCAGCGGCCTCGGCTGCGGCCTCCGGGGGGCCCTCGGCGGCGCCGAG  199
AK127592     ------------------------------------------------------------

NM_015905    CGGGGAGAACGAGGCCGAGAGTCGGCAGGGCCCGGACTCGGAGCGCGGCGGCGAGGCGGC  358
NM_003852    CGGGGAGAACGAGGCCGAGAGTCGGCAGGGCCCGGACTCGGAGCGCGGCGGCGAGGCGGC  358
AF009353     CGGGGAGAACGAGGCCGAGAGTCGGCAGGGCCCGGACTCGGAGCGCGGCGGCGAGGCGGC  134
BC028689     CGGGGAGAACGAGGCCGAGAGTCGGCAGGGCCCGGACTCGGAGCGCGGCGGCGAGGCGGC  256
AF119042     CGGGGAGAACGAGGCCGAGAGTCGGCAGGGCCCGGACTCGGAGCGCGGCGGCGAGGCGGC  259
AK127592     -----------------------------------ATGGAGGGCCCGCGCTCTGCGGC  23
                                                * ***  **  **    *****

NM_015905    CCGGCTCAACCTGTTGGACACTTGCGCCGTGTGCCACCAGAACATCCAGAGCCGGGCGCC  418
NM_003852    CCGGCTCAACCTGTTGGACACTTGCGCCGTGTGCCACCAGAACATCCAGAGCCGGGCGCC  418
AF009353     CCGGCTCAACCTGTTGGACACTTGCGCCGTGTGCCACCAGAACATCCAGAGCCGGGCGCC  194
BC028689     CCGGCTCAACCTGTTGGACACTTGCGCCGTGTGCCACCAGAACATCCAGAGCCGGGCGCC  316
AF119042     CCGGCTCAACCTGTTGGACACTTGCGCCGTGTGCCACCAGAACATCCAGAGCCGGGCGCC  319
AK127592     GTGTCGCGCTCGGCCAGCAACTTCC-CCGGGCGCTGTGGACTTGACC-GCGCCGC-CGCC  80
              *  *     *  *       ****  *  ***  *  **     **   *  ****  ****

NM_015905    CAAGCTGCTGCCCTGCCTGCACT-CTTTCTGCCAGCGCTGCCTGCCCGCGCCCCAGCGCT  477
NM_003852    CAAGCTGCTGCCCTGCCTGCACT-CTTTCTGCCAGCGCTGCCTGCCCGCGCCCCAGCGCT  477
AF009353     CAAGCTGCTGCCCTGCCTGCACT-CTTTCTGCCAGCGCTGCCTGCCCGCGCCCCAGCGCT  253
BC028689     CAAGCTGCTGCCCTGCCTGCACT-CTTTCTGCCAGCGCTGCCTGCCCGCGCCCCAGCGCT  375
AF119042     CAAGCTGCTGCCCTGCCTGCACT-CTTTCTGCCAGCGCTGCCTGCCCGCGCCCCAGCGCT  378
AK127592     GCCGCCGCTGCTCCGCATTCTCAACAGCCGGGCGGCCCCTGCCACTCGACTTTTGCAG-  139
              *  ***** **  *  *   *   *  *  ** *    *  **  *  *  *    **
```

FIG. 9A

```
NM_015905   ACCTCATGCTGCCCGCGCCCATGCTGGGCTCGGCCGAGACCCCGCCACCCGTC-CCTGCC  536
NM_003852   ACCTCATGCTGCCCGCGCCCATGCTGGGCTCGGCCGAGACCCCGCCACCCGTC-CCTGCC  536
AF009353    ACCTCATGCTGCCCGCGCCCATGCTGGGCTCGGCCGAGACCCCGCCACCCGTC-CCTGCC  312
BC028689    ACCTCATGCTGCCCGCGCCCATGCTGGGCTCGGCCGAGACCCCGCCACCCGTC-CCTGCC  434
AF119042    ACCTCATGCTGCCCGCGCCCATGCTGGGCTCGGCCGAGACCCCGCCACCCGTC-CCTGCC  437
AK127592    ACCTC-TGTCGGAGTCTCCTGCAGCCGGAATCTCGGGTTCTTTGCCGGCTGCAGCCAGTT  198
            *****  **   *   * **       **     *  *    ***  *  *    **  *
                                                        sirna_115465
NM_015905   CCCGGCTCGCCGGTCAGCGGCTCGTCGCCGTTCGCCACCCAAGTTGGAGTCATTCGTTGC  596
NM_003852   CCCGGCTCGCCGGTCAGCGGCTCGTCGCCGTTCGCCACCCAAGTTGGAGTCATTCGTTGC  596
AF009353    CC-GGCTCGCCGGTCAGC--CTCGTCGCCGTTCGCCACCCAAGTTGGAGTCATTCGTTGC  369
BC028689    CCCGGCTCGCCGGTCAGCGGCTCGTCGCCGTTCGCCACCCAAGTTGGAGTCATTCGTTGC  494
AF119042    CCCGGCTCGCCGGTCAGCGGCTCGTCGCCGTTCGCCACCCAAGTTGGAGTCATTCGTTGC  497
AK127592    AACTGCTACCCGCCCGCTGCCTC--CACAAAGCTTTGTCCA-GTTGGAGTCATTCGTTGC  255
              *     ***     ***       *  *     *     *** ******************

NM_015905   CCAGTTTGCAGCCAAGAATGTGCAGAGAGACACATCATAGATAACTTTTTTGTGAAGGAC  656
NM_003852   CCAGTTTGCAGCCAAGAATGTGCAGAGAGACACATCATAGATAACTTTTTTGTGAAGGAC  656
AF009353    CCAGTTTGCAGCCAAGAATGTGCAGAGAGACACATCATAGATAACTTTTTTGTGAAGGAC  429
BC028689    CCAGTTTGCAGCCAAGAATGTGCAGAGAGACACATCATAGATAACTTTTTTGTGAAGGAC  554
AF119042    CCAGTTTGCAGCCAAGAATGTGCAGAGAGACACATCATAGATAACTTTTTTGTGAAGGAC  557
AK127592    CCAGTTTGCAGCCAAGAATGTGCAGAGAGACACATCATAGATAACTTTTTTGTGAAGGAC  315
            ************************************************************
                                                        sirna_103317
NM_015905   ACTACTGAGGTTCCCAGCAGTACAGTAGAAAAGTCAAATCAGGTATGTACAAGCTGTGAG  716
NM_003852   ACTACTGAGGTTCCCAGCAGTACAGTAGAAAAGTCAAATCAGGTATGTACAAGCTGTGAG  716
AF009353    ACTACTGAGGTTCCCAGCAGTACAGTAGAAAAGTCAAATCAGGTATGTACAAGCTGTGAG  489
BC028689    ACTACTGAGGTTCCCAGCAGTACAGTAGAAAAGTCAAATCAGGTATGTACAAGCTGTGAG  614
AF119042    ACTACTGAGGTTCCCAGCAGTACAGTAGAAAAGTCAAATCAGGTATGTACAAGCTGTGAG  617
AK127592    ACTACTGAGGTTCCCAGCAGTACAGTAGAAAAGTCAAATCAGGTATGTACAAGCTGTGAG  375
            ************************************************************
                        sirna_103402
NM_015905   GACAACGCAGAAGCCAATGGGTTTTGTGTAGAGTGTGTTGAATGGCTCTGCAAGACGTGT  776
NM_003852   GACAACGCAGAAGCCAATGGGTTTTGTGTAGAGTGTGTTGAATGGCTCTGCAAGACGTGT  776
AF009353    GACAACGCAGAAGCCAATGGGTTTTGTGTAGAGTGTGTTGAATGGCTCTGCAAGACGTGT  549
BC028689    GACAACGCAGAAGCCAATGGGTTTTGTGTAGAGTGTGTTGAATGGCTCTGCAAGACGTGT  674
AF119042    GACAACGCAGAAGCCAATGGGTTTTGTGTAGAGTGTGTTGAATGGCTCTGCAAGACGTGT  677
AK127592    GACAACGCAGAAGCCAATGGGTTTTGTGTAGAGTGTGTTGAATGGCTCTGCAAGACGTGT  435
            ************************************************************

NM_015905   ATCAGAGCTCATCAGAGGGTAAAGTTCACAAAAGACCACACTGTCAGACAGAAAGAGGAA  836
NM_003852   ATCAGAGCTCATCAGAGGGTAAAGTTCACAAAAGACCACACTGTCAGACAGAAAGAGGAA  836
AF009353    ATCAGAGCTCATCAGAGGGTAAAGTTCACAAAAGACCACACTGTCAGACAGAAAGAGGAA  609
BC028689    ATCAGAGCTCATCAGAGGGTAAAGTTCACAAAAGACCACACTGTCAGACAGAAAGAGGAA  734
AF119042    ATCAGAGCTCATCAGAGGGTAAAGTTCACAAAAGACCACACTGTCAGACAGAAAGAGGAA  737
AK127592    ATCAGAGCTCATCAGAGGGTAAAGTTCACAAAAGACCACACTGTCAGACAGAAAGAGGAA  495
            ************************************************************
```

FIG. 9B

```
NM_015905   GTATCTCCAGAGGCAGTTGGTGTCACCAGCCAGCGACCAGTGTTTTGTCCTTTTCATAAA 896
NM_003852   GTATCTCCAGAGGCAGTTGGTGTCACCAGCCAGCGACCAGTGTTTTGTCCTTTTCATAAA 896
AF009353    GTATCTCCAGAGGCAGTTGGTGTCACCAGCCAGCGACCAGTGTTTTGTCCTTTTCATAAA 669
BC028689    GTATCTCCAGAGGCAGTTGGTGTCACCAGCCAGCGACCAGTGTTTTGTCCTTTTCATAAA 794
AF119042    GTATCTCCAGAGGCAGTTGGTGTCACCAGCCAGCGACCAGTGTTTTGTCCTTTTCATAAA 797
AK127592    GTATCTCCAGAGGCAGTTGGTGTCACCAGCCAGCGACCAGTGTTTTGTCCTTTTCATAAA 555
            ************************************************************

NM_015905   AAGGAGCAGCTGAAGCTGTACTGTGAGACATGTGACAAACTGACATGTCGAGACTGTCAG 956
NM_003852   AAGGAGCAGCTGAAGCTGTACTGTGAGACATGTGACAAACTGACATGTCGAGACTGTCAG 956
AF009353    AAGGAGCAGCTGAAGCTGTACTGTGAGACATGTGACAAACTGACATGTCGAGACTGTCAG 729
BC028689    AAGGAGCAGCTGAAGCTGTACTGTGAGACATGTGACAAACTGACATGTCGAGACTGTCAG 854
AF119042    AAGGAGCAGCTGAAGCTGTACTGTGAGACATGTGACAAACTGACATGTCGAGACTGTCAG 857
AK127592    AAGGAGCAGCTGAAGCTGTACTGTGAGACATGTGACAAACTGACATGTCGAGACTGTCAG 615
            ************************************************************ sirna_10246671
NM_015905   TTGTTAGAACATAAAGAGCATAGATACCAATTTATAGAAGAAGCTTTTCAGAATCAGAAA 1016
NM_003852   TTGTTAGAACATAAAGAGCATAGATACCAATTTATAGAAGAAGCTTTTCAGAATCAGAAA 1016
AF009353    TTGTTAGAACATAAAGAGCATAGATACCAATTTATAGAAGAAGCTTTTCAGAATCAGAAA 789
BC028689    TTGTTAGAACATAAAGAGCATAGATACCAATTTATAGAAGAAGCTTTTCAGAATCAGAAA 914
AF119042    TTGTTAGAACATAAAGAGCATAGATACCAATTTATAGAAGAAGCTTTTCAGAATCAGAAA 917
AK127592    TTGTTAGAACATAAAGAGCATAGATACCAATTTATAGAAGAAGCTTTTCAGAATCAGAAA 675
            ************************************************************

NM_015905   GTGATCATAGATACACTAATCACCAAACTGATGGAAAAAACAAAATACATAAAATTCACA 1076
NM_003852   GTGATCATAGATACACTAATCACCAAACTGATGGAAAAAACAAAATACATAAAATTCACA 1076
AF009353    GTGATCATAGATACACTAATCACCAAACTGATGGAAAAAACAAAATACATAAAATTCACA 849
BC028689    GTGATCATAGATACACTAATCACCAAACTGATGGAAAAAACAAAATACATAAAATTCACA 974
AF119042    GTGATCATAGATACACTAATCACCAAACTGATGGAAAAAACAAAATACATAAAATTCACA 977
AK127592    GTGATCATAGATACACTAATCACCAAACTGATGGAAAAAACAAAATACATAAAATTCACA 735
            ************************************************************ sirna_107252                            sirna_107253
NM_015905   CGAAATCAGATCCAAAACAGAATTATTGAACTAAATCAAAATCAAAAGCAGGTGGAACAG 1136
NM_003852   GGAAATCAGATCCAAAACAGAATTATTGAAGTAAATCAAAATCAAAAGCAGGTGGAACAG 1136
AF009353    GGAAATCAGATCCAAAACAGAATTATTGAAGTAAATCAAAATCAAAAGCAGGTGGAACAG 909
BC028689    GGAAATCAGATCCAAAACAGAATTATTGAAGTAAATCAAAATCAAAAGCAGGTGGAACAG 1034
AF119042    GGAAATCAGATCCAAAACAGAATTATTGAAGTAAATCAAAATCAAAAGCAGGTGGAACAG 1037
AK127592    GGAAATCAGATCCAAAACAGAATTATTGAAGTAAATCAAAATCAAAAGCAGGTGGAACAG 795
            ************************************************************

NM_015905   GATATTAAAGTTGCTATATTTACACTGATGGTAGAAATAAATAAAAAAGGAAAAGCTCTA 1196
NM_003852   GATATTAAAGTTGCTATATTTACACTGATGGTAGAAATAAATAAAAAAGGAAAAGCTCTA 1196
AF009353    GATATTAAAGTTGCTATATTTACACTGATGGTAGAAATAAATAAAAAAGGAAAAGCTCTA 969
BC028689    GATATTAAAGTTGCTATATTTACACTGATGGTAGAAATAAATAAAAAAGGAAAAGCTCTA 1094
AF119042    GATATTAAAGTTGCTATATTTACACTGATGGTAGAAATAAATAAAAAAGGAAAAGCTCTA 1097
AK127592    GATATTAAAGTTGCTATATTTACACTGATGGTAGAAATAAATAAAAAAGGAAAAGCTCTA 855
            ************************************************************

NM_015905   CTGCATCAGTTAGAGAGCCTTGCAAAGGACCATCGCATGAAACTTATGCAACAACAACAG 1256
NM_003852   CTGCATCAGTTAGAGAGCCTTGCAAAGGACCATCGCATGAAACTTATGCAACAACAACAG 1256
AF009353    CTGCATCAGTTAGAGAGCCTTGCAAAGGACCATCGCATGAAACTTATGCAACAACAACAG 1029
BC028689    CTGCATCAGTTAGAGAGCCTTGCAAAGGACCATCGCATGAAACTTATGCAACAACAACAG 1154
AF119042    CTGCATCAGTTAGAGAGCCTTGCAAAGGACCATCGCATGAAACTTATGCAACAACAACAG 1157
AK127592    CTGCATCAGTTAGAGAGCCTTGCAGAGGACCATCGCATGAAACTTATGCAACAACAACAG 915
            ************************ ***********************************
```

FIG. 9C

```
NM_015905   GAAGTGGCTGGACTCTCTAAACAATTGGAGCATGTCATGCATTTTTCTAAATGGGCAGTT 1316
NM_003852   GAAGTGGCTGGACTCTCTAAACAATTGGAGCATGTCATGCATTTTTCTAAATGGGCAGTT 1316
AF009353    GAAGTGACTGGACTCTCTAAACAATTGGAGCATGTCATGCATTTTTCTAAATGGGCAGTT 1089
BC028689    GAAGTGGCTGGACTCTCTAAACAATTGGAGCATGTCATGCATTTTTCTAAATGGGCAGTT 1214
AF119042    GAAGTGGCTGGACTCTCTAAACAATTGGAGCATGTCATGCATTTTTCTAAATGGGCAGTT 1217
AK127592    GAAGTGGCTGGACTCTCTAAACAATTGGAGCATGTCATGCATTTTTCTAAATGGGCAGTT 975
            ****** *****************************************************
                                                   sirna_10246675
NM_015905   TCCAGTGGCAGCAGTACAGCATTACTTTATAGCAAACGACTGATTACATACCGGTTACGG 1376
NM_003852   TCCAGTGGCAGCAGTACAGCATTACTTTATAGCAAACGACTGATTACATACCGGTTACGG 1376
AF009353    TCCAGTGGCAGCAGTACAGCATTACTTTATAGCAAACGACTGATTACATACCGGTTACGG 1149
BC028689    TCCAGTGGCAGCAGTACAGCATTACTTTATAGCAAACGACTGATTACATACCGGTTACGA 1274
AF119042    TCCAGTGGCAGCAGTACAGCATTACTTTATAGCAAACGACTGATTACATACCGGTTACGG 1277
AK127592    TCCAGTGGCAGCAGTACAGCATTACTTTATAGCAAACGACTGATTACATACCGGTTACGG 1035
            ************************************************************

NM_015905   CACCTCCTTCGTGCAAGGTGTGATGCATCCCCAGTGACCAACAACACCATCCAATTTCAC 1436
NM_003852   CACCTCCTTCGTGCAAGGTGTGATGCATCCCCAGTGACCAACAACACCATCCAATTTCAC 1436
AF009353    CACCTCCTTCGTGCAAGGTGTGATGCATCCCCAGTGACCAACAACACCATCCAATTTCAC 1209
BC028689    CACCTCCTTCGTGCAAGGTGTGATGCATCCCCAGTGACCAACAACACCATCCAATTTCAC 1334
AF119042    CACCTCCTTCGTGCAAGGTGTGATGCATCCCCAGTGACCAACAACACCATCCAATTTCAC 1337
AK127592    CACCTCCTTCGTGCAAGGTGTGATGCATCCCCAGTGACCAACAACACCATCCAATTTCAC 1095
            ************************************************************

NM_015905   TGTGATCCTAGTTTCTGGGCTCAAAATATCATCAACTTAGGTTCTTTAGTAATCGAGGAT 1496
NM_003852   TGTGATCCTAGTTTCTGGGCTCAAAATATCATCAACTTAGGTTCTTTAGTAATCGAGGAT 1496
AF009353    TGTGATCCTAGTTTCTGGGCTCAAAATATCATCAACTTAGGTTCTTTAGTAATCGAGGAT 1269
BC028689    TGTGATCCTAGTTTCTGGGCTCAAAATATCATCAACTTAGGTTCTTTAGTAATCGAGGAT 1394
AF119042    TGTGATCCTAGTTTCTGGGCTCAAAATATCATCAACTTAGGTTCTTTAGTAATCGAGGAT 1397
AK127592    TGTGATCCTAGTTTCTGGGCTCAAAATATCATCAACTTAGGTTCTTTAGTAATCGAGGAT 1155
            ************************************************************

NM_015905   AAAGAGAGCCAGCCACAAATGCCTAAGCAGAATCCTGTCGTGGAACAGAATTCACAGCCA 1556
NM_003852   AAAGAGAGCCAGCCACAAATGCCTAAGCAGAATCCTGTCGTGGAACAGAATTCACAGCCA 1556
AF009353    AAAGAGAGCCAGCCACAAATGCCTAAGCAGAATCCTGTCGTGGAACAGAATTCACAGCCA 1329
BC028689    AAAGAGAGCCAGCCACAAATGCCTAAGCAGAATCCTGTCGTGGAACAGAATTCACAGCCA 1454
AF119042    AAAGAGAGCCAGCCACAAATGCCTAAGCAGAATCCTGTCGTGGAACAGAATTCACAGCCA 1457
AK127592    AAAGAGAGCCAGCCACAAATGCCTAAGCAGAATCCTGTCGTGGAACAGAATTCACAGCCA 1215
            ************************************************************

NM_015905   CCAAGTGGTTTATCATCAAACCAGTTATCCAAGTTCCCAACACAGATCAGCCTAGCTCAA 1616
NM_003852   CCAAGTGGTTTATCATCAAACCAGTTATCCAAGTTCCCAACACAGATCAGCCTAGCTCAA 1616
AF009353    CCAAGTGGTTTATCATCAAACCAGTTATCCAAGTTCCCAACACAGATCAGCCTAGCTCAA 1389
BC028689    CCAAGTGGTTTATCATCAAACCACTTATCCAAGTTCCCAACACAGATCAGCCTAGCTCAA 1514
AF119042    CCAAGTGGTTTATCATCAAACCAGTTATCCAAGTTCCCAACACAGATCAGCCTAGCTCAA 1517
AK127592    CCAAGTGGTTTATCATCAAACCAGTTATCCAAGTTCCCAACACAGATCAGCCTAGCTCAA 1275
            *********************** ************************************

NM_015905   TTACGGCTCCAGCATATGCAGCAACAGGTAATGGCTCAGAGGCAACAGGTGCAACGGAGG 1676
NM_003852   TTACGGCTCCAGCATATGCAGCAACAG--------------------------------- 1643
AF009353    TTACGGCTCCAGCATATGCAGCAACAG--------------------------------- 1416
BC028689    TTACGGCTCCAGCATATGCAGCAACAGGTAATGGCTCAGAGGCAACAGGTGCAACGGAGG 1574
AF119042    TTACGGCTCCAGCATATGCAGCAACAG--------------------------------- 1544
AK127592    TTACGGCTCCAGCATATGCAGCAACAG--------------------------------- 1302
            ***************************
```

FIG. 9D

```
NM_015905    CCAGCACCTGTGGGTTTACCAAACCCTAGAATGCAGGGGCCCATCCAGCAACCTTCCATC 1736
NM_003852    ------------------------------------------------------------
AF009353     ------------------------------------------------------------
BC028689     CCAGCACCTGTGGGTTTACCAAACCCTAGAATGCAGGGGCCCATCCAGCAACCTTCCATC 1634
AF119042     ------------------------------------------------------------
AK127592     ------------------------------------------------------------

NM_015905    TCTCATCAGCAACCGCCTCCACGTTTGATAAACTTTCAGAATCACAGCCCCAAACCCAAT 1796
NM_003852    ---------CAACCGCCTCCACGTTTGATAAACTTTCAGAATCACAGCCCCAAACCCAAT 1694
AF009353     ---------CAACCGCCTCCACGTTTGATAAACTTTCAGAATCACAGCCCCAAACCCAAT 1467
BC028689     TCTCATCAGCAACCGCCTCCACGTTTGATAAACTTTCAGAATCACAGCCCCAAACCCAAT 1694
AF119042     ---------CAACCGCCTCCACGTTTGATAAACTTTCAGAATCACAGCCCCAAACCCAAT 1595
AK127592     ---------CAACCGCCTCCACGTTTGATAAACTTTCAGAATCACAGCCCCAAACCCAAT 1353
                      ***************************************************

NM_015905    GGACCAGTTCTTCCTCCTCATCCTCAACAACTGAGATATCCACCAAACCAGAACATACCA 1856
NM_003852    GGACCAGTTCTTCCTCCTCATCCTCAACAACTGAGATATCCACCAAACCAGAACATACCA 1754
AF009353     GGACCAGTTCTTCCTCCTCATCCTCAACAACTGAGATATCCACCAAACCAGAACATACCA 1527
BC028689     GGACCAGTTCTTCCTCCTCATCCTCAACAACTGAGATATCCACCAAACCAGAACATACCA 1754
AF119042     GGACCAGTTCTTCCTCCTCATCCTCAACAACTGAGATATCCACCAAACCAGAACATACCA 1655
AK127592     GGACCAGTTCTTCCTCCTCATCCTCAACAACTGAGATATCCACCAAACCAGAACATACCA 1413
             ************************************************************

NM_015905    CGACAAGCAATAAAGCCAAACCCCCTACAGATGGCTTTCTTGGCTCAACAAGCCATAAAA 1916
NM_003852    CGACAAGCAATAAAGCCAAACCCCCTACAGATGGCTTTCTTGGCTCAACAAGCCATAAAA 1814
AF009353     CGACAAGCAATAAAGCCAAACCCCCTACAGATGGCTTTCTTGGCTCAACAAGCCATAAAA 1587
BC028689     CGACAAGCAATAAAGCCAAACCCCCTACAGATGGCTTTCTTGGCTCAACAAGCCATAAAA 1814
AF119042     CGACAAGCAATAAAGCCAAACCCCCTACAGATGGCTTTCTTGGCTCAACAAGCCATAAAA 1715
AK127592     CGACAAGCAATAAAGCCAAACCCCCTACAGATGGCTTTCTTGGCTCAACAAGCCATAAAA 1473
             ************************************************************

NM_015905    CAGTGGCAGATCAGCAGTGGACAGGGAACCCCATCAACTACCAACAGCACATCCTCTACT 1976
NM_003852    CAGTGGCAGATCAGCAGTGGACAGGGAACCCCATCAACTACCAACAGCACATCCTCTACT 1874
AF009353     CAGTGGCAGATCAGCAGTGGACAGGGAACCCCATCAACTACCAACAGCACATCCTCTACT 1647
BC028689     CAGTGGCAGATCAGCAGTGGACAGGGAACCCCATCAACTACCAACAGCACATCCTCTACT 1874
AF119042     CAGTGGCAGATCAGCAGTGGACAGGGAACCCCATCAACTACCAACAGCACATCCTCTACT 1775
AK127592     CAGTGGCAGATCAGCAGTGGACAGGGAACCCCATCAACTACCCAAAATATA------AAT 1527
             ******************************************  *    *  *    * *

NM_015905    CCTTCCAGCCCCACGATTACTAGTGCAGCAGGATATGATGGAAAGGCTTTTGGTTCACCT 2036
NM_003852    CCTTCCAGCCCCACGATTACTAGTGCAGCAGGATATGATGGAAAGGCTTTTGGTTCACCT 1934
AF009353     CCTTCCAGCCCCACGATTACTAGTGCAGCAGGATATAATGGAAAGGCTTTTGGTTCACCT 1707
BC028689     CCTTCCAGCCCCACGATTACTAGTGCAGCAGGATATGATGGAAAGGCTTTTGGTTCACCT 1934
AF119042     CCTTCCAGCCCCACGATTACTAGTGCAGCAGGATATGATGGAAAGGCTTTTGGTTCACCT 1835
AK127592     ACAGCAGCGTGCACTGTATTTGATGTGAGGGTTCTTCATCATATACCCTACTGGGCATTA 1587
               *    ***  *    *  **    *   * **    *     *   *     *  **

NM_015905    ATGATCGATTTGAGCTCACCAGTGGGAGGGTCTTATAATCTTCCCTCTCTTCCGGATATT 2096
NM_003852    ATGATCGATTTGAGCTCACCAGTGGGAGGGTCTTATAATCTTCCCTCTCTTCCGGATATT 1994
AF009353     ATAATCGATTTGAGCTCACCAGTGGGAGGGTCTTATAATCTTCCCTCTCTTCCGGATATT 1767
BC028689     ATGATCGATTTGAGCTCACCAGTGGGAGGGTCTTATAATCTTCCCTCTCTTCCGGATATT 1994
AF119042     ATGATCGATTTGAGCTCACCAGTGGGAGGGTCTTATAATCTTCCCTCTCTTCCGGATATT 1895
AK127592     A------ATATAAGTTCCTC--TGAAAGGGACTCGTTTTGTGGTTTTCATCTGTCTATA  1639
             *       ** **  **     * **    *       *  * ** ** *     ***
```

FIG. 9E

```
NM_015905   GACTGTTCAAGTACTATTATGCTGGACAATATTGTGAGGAAAGATACTAATATAGATCAT 2156
NM_003852   GACTGTTCAAGTACTATTATGCTGGACAATATTGTGAGGAAAGATACTAATATAGATCAT 2054
AF009353    GACTGTTCAAGTACTATTATGCTGGACAATATTGTGAGGAAAGATACTAATATAGATCAT 1827
BC028689    GACTGTTCAAGTACTATTATGCTGGACAATATTGTGAGGAAAGATACTAATATAGATCAT 2054
AF119042    GACTGTTCAAGTACTATTATGCTGGACAATATTGTGAGGAAAGATACTAATATAGATCAT 1955
AK127592    ATTTG---GAATGAAAATGTGTTGTAGGATTTTGGGAGCAGGCA-----------GCTGG 1685
              **    *   *  *  *    *    *  ***  *      * sirna_10246670
NM_015905   GGCCAGCCAAGACCACCCTCAAACAGAACGGTCCAGTCACCAAATTCATCAGTGCCATCT 2216
NM_003852   GGCCAGCCAAGACCACCCTCAAACAGAACGGTCCAGTCACCAAATTCATCAGTGCCATCT 2114
AF009353    GGCCAGCCAAGACCACCCTCAAACAGAACGGTCCAGTCACCAAATTCATCAGTGCCATCT 1887
BC028689    GGCCAGCCAAGACCACCCTCAAACAGAACGGTCCAGTCACCAAATTCATCAGTGCCATCT 2114
AF119042    GGCCAGCCAAGACCACCCTCAAACAGAACGGTCCAGTCACCAAATTCATCAGTGCCATCT 2015
AK127592    GGCGAATTAATAGTGATTTTTTTTTTTTCCTGAAGCATCTATCTCAT--GTTTTTCTT   1743
            ***  *    **  *         *          *   **  *   ****  **   *

NM_015905   CCAGGCCTTGCAGGACCTGTTACTATGACTAGTGTACACCCCCCAATACGTTCACCTAGT 2276
NM_003852   CCAGGCCTTGCAGGACCTGTTACTATGACTAGTGTACACCCCCCAATACGTTCACCTAGT 2174
AF009353    CCAGGCCTTGCAGGACCTGTTACTATGACTAGTGTACACCCCCCAATACGTTCACCTAGT 1947
BC028689    CCAGGCCTTGCAGGACCTGTTACTATGACTAGTGTACACCCCCCAATACGTTCACCTAGT 2174
AF119042    CCAGGCCTTGCAGGACCTGTTACTATGACTAGTGTACACCCCCCAATACGTTCACCTAGT 2075
AK127592    TTGAGAGTCAGAACATCAAACTTAATCTTTGATCTG-ACTTCTGATTTTATTCTTCTGAT 1802
             *  *  *  *  **    *   *  *  *  **    *  *    ***  **  *

NM_015905   GCCTCCAGCGTTGGAAGCCGAGGAAGCTCTGGCTCTTCCAGCAAACCAGCAGGAGCTGAC 2336
NM_003852   GCCTCCAGCGTTGGAAGCCGAGGAAGCTCTGGCTCTTCCAGCAAACCAGCAGGAGCTGAC 2234
AF009353    GCCTCCAGCGTTGGAAGCCGAGGAAGCTCTGGCTCTTCCAGCAAACCAGCAGGAGCTGAC 2007
BC028689    GCCTCCAGCGTTGGAAGCCGAGGAAGCTCTGGCTCTTCCAGCAAACCAGCAGGAGCTGAC 2234
AF119042    GCCTCCAGCGTTGGAAGCCGAGGAAGCTCTGGCTCTTCCAGCAAACCAGCAGGAGCTGAC 2135
AK127592    ----TGATTGATAGAGGTACAAAAGACTT---ATCTTCT-GAGGACAAGCATATTCTTAA 1854
                *   *  **   *    *    **     *****    *   ** ****   ** *

NM_015905   TCTACACACAAAGTCCCAGTGGTCATGCTGGAGCCAATTCGAATAAAACAAGAAAACAG- 2395
NM_003852   TCTACACACAAAGTCCCAGTGGTCATGCTGGAGCCAATTCGAATAAAACAAGAAAACAG- 2293
AF009353    TCTACACACAAAGTCCCAGTGGTCATGCTGGAGCCAATTCGAATAAAACAAGAAAACAG- 2066
BC028689    TCTACACACAAAGTCCCAGTGGTCATGCTGGAGCCAATTCGAATAAAACAAGAAAACAG- 2293
AF119042    TCTACACACAAAGTCCCAGTGGTCATGCTGGAGCCAATTCGAATAAAACAAGAAAACAG- 2194
AK127592    TGTGC-CAGACCTACCCGGTTCAGCTGATATAGATAGATAGATAGAAGAAAATTGC     1913
            *  *  **  *    ***  **   **  *    *    **   *   ** ********  *

NM_015905   TGGACCACCGGAAAATTATGATTTCCCTGTTGTTATAGTGAAGCAAGAATCAGATGAAG- 2454
NM_003852   TGGACCACCGGAAAATTATGATTTCCCTGTTGTTATAGTGAAGCAAGAATCAGATGAAG- 2352
AF009353    TGGACCACCGGAAAATTATGATTTCCCAGTTGTTATAGTGAAGCAAGAATCAGATGAAG- 2125
BC028689    TGGACCACCGGAAAATTATGATTTCCCTGTTGTTATAGTGAAGCAAGAATCAGATGAAG- 2352
AF119042    TGGACCACCGGAAAATTATGATTTCCCTGTTGTTATAGTGAAGCAAGAATCAGATGAAG- 2253
AK127592    TGTGCCAT----ACATTA--ATCCAGCATTTGACACAATATCTAAATGGTTTGCCGAAGT 1967
            **  ***     *  ****  **    *   *** *  *         **   *   *  ****

NM_015905   -AATCTAGGCCT-CAAAATGCCAATTATCCAAGAAGCATACTCACCTCCCTGCTCTTAAA 2512
NM_003852   -AATCTAGGCCT-CAAAATGCCAATTATCCAAGAAGCATACTCACCTCCCTGCTCTTAAA 2410
AF009353    -AATCTAGGCCT-CAAAATGCCAATTATCCAAGAAGCATACTCACCTCCCTGCTCTTAAA 2183
BC028689    -AATCTAGGCCT-CAAAATGCCAATTATCCAAGAAGCATACTCACCTCCCTGCTCTTAAA 2410
AF119042    -AATCTAGGCCT-CAAAATGCCAATTATCCAAGAAGCATACTCACCTCCCTGCTCTTAAA 2311
AK127592    TAATCTGTATTTTATAAAACATTAACT------GGAGTAAATTTTTCTCCTTAGGATGATA 2021
             ****   *  **** ** *        *  **  *  *     **** *     *   *
```

FIG. 9F

```
NM_015905    TAGCAGTCAGAGCTCTACTTCTGAGGAGACTGT-----GC-TAAGATCAGATGCCCCTGA  2566
NM_003852    TAGCAGTCAGAGCTCTACTTCTGAGGAGACTGT-----GC-TAAGATCAGATGCCCCTGA  2464
AF009353     TAGCAGTCAGAGCTCTACTTCTGAGGAGACTGT-----GC-TAAGATCAGATGCCCCTGA  2237
BC028689     TAGCAGTCAGAGCTCTACTTCTGAGGAGACTGT-----GC-TAAGATCAGATGCCCCTGA  2464
AF119042     TAGCAGTCAGAGCTCTACTTCTGAGGAGACTGT-----GC-TAAGATCAGATGCCCCTGA  2365
AK127592     GAATAAAAAGAGCTC-ACTTGAAAGAAGGCTATTATTTGCATTATATCACCTGCCATAAA  2080
              *  *  ******* ****   ** ** ** *       ** * * ****  ****   *

NM_015905    T--AGTACAGG--AGATCAACCTGGACTTCACCAGGACAATTCCTCAAATGGAAAGTCTG  2622
NM_003852    T--AGTACAGG--AGATCAACCTGGACTTCACCAGGACAATTCCTCAAATGGAAAGTCTG  2520
AF009353     T--AGTACAGG--AGATCAACCTGGACTTCACCAGGACAATTCCTCAAATGGAAAGTCTG  2293
BC028689     T--AGTACAGG--AGATCAACCTGGACTTCACCAGGACAATTCCTCAAATGGAAAGTCTG  2520
AF119042     T--AGTACAGG--AGATCAACCTGGACTTCACCAGGACAATTCCTCAAATGGAAAGTCTG  2421
AK127592     TTTAACACAGTCTGGAGTGATAGCTACTGTAGAAAGGAAATAGACTTTGTATGAACTCTT  2140
              *  * ****    **     *     ***  *  *  ***         ** ***

NM_015905    AATGGTTGGATCCTTCCCAGAAGTCACCTCTTCATGT-TGGAGAGACAAGGAAAGAGGAT  2681
NM_003852    AATGGTTGGATCCTTCCCAGAAGTCACCTCTTCATGT-TGGAGAGACAAGGAAAGAGGAT  2579
AF009353     AATGGTTGGATCCTTCCCAGAAGTCACCTCTTCATGT-TGGAGAGACAAGGAAAGAGGAT  2352
BC028689     AATGGTTGGATCCTTCCCAGAAGTCACCTCTTCATGT-TGGAGAGACAAGGAAAGAGGAT  2579
AF119042     AATGGTTGGATCCTTCCCAGAAGTCACCTCTTCATGT-TGGAGAGACAAGGAAAGAGGAT  2480
AK127592     TAAGTTGAAAAGTTAAATATATGTGGTTTGGATGTGTGCTTTAATTCAGCTTTAGAAATT  2200
              *  *    *    *    *  * **      *   ***   *  *   ***      *

NM_015905    GACCCCAATGAGGACTGGT-GTGCAGTTTGTCAAAACGGAGGGGAACTCCTCTGCTGTGA  2740
NM_003852    GACCCCAATGAGGACTGGT-GTGCAGTTTGTCAAAACGGAGGGGAACTCCTCTGCTGTGA  2638
AF009353     GACCCCAATGAGGACTGGT-GTGCAGTTTGTCAAAACGGAGGGGAACTCCTCTGCTGTGA  2411
BC028689     GACCCCAATGAGGACTGGT-GTGCAGTTTGTCAAAACGGAGGGGAACTCCTCTGCTGTGA  2638
AF119042     GACCCCAATGAGGACTGGT-GTGCAGTTTGTCAAAACGGAGGGGAACTCCTCTGCTGTGA  2539
AK127592     AATACCACTACCCGTGAATTATATGGCCTGACAATATGAATTAGGTGTACTGTACTGAAG  2260
              *  ***  *          *  *   *  ** *** * * *     *  ** * ***

NM_015905    AA-AGTGCCCCA-AAGTATTCCATCTTTCTTGTCATGTG-CCCACATTGACAAATTTTCC  2797
NM_003852    AA-AGTGCCCCA-AAGTATTCCATCTTTCTTGTCATGTG-CCCACATTGACAAATTTTCC  2695
AF009353     AA-AGTGCCCCA-AAGTATTCCATCTTTCTTGTCATGTG-CCCACATTGACAAATTTTCC  2468
BC028689     AA-AGTGCCCCA-AAGTATTCCATCTTTCTTGTCATGTG-CCCACATTGACAAATTTTCC  2695
AF119042     AA-AGTGCCCCA-AAGTATTCCATCTTTCTTGTCATGTG-CCCACATTGACAAATTTTCC  2596
AK127592     AACAGTACTCCACAAACATGGGTGGTAACAAGAGTTCCATCCCAGGAGGCCAAACGGTGC  2320
             ** *** * *** *  **  **    *  *     *  * ****  *  **** *  *

NM_015905    AAGTGGAGAGTGGATTTGCACTTTCTGCCGAGACTTATCTAAACCAGAAGTTGAATATGA  2857
NM_003852    AAGTGGAGAGTGGATTTGCACTTTCTGCCGAGACTTATCTAAACCAGAAGTTGAATATGA  2755
AF009353     AAGTGGAGAGTGGATTTGCACTTTCTGCCGAGACTTATCTAAACCAGAAGTTGAATATGA  2528
BC028689     AAGTGGAGAGTGGATTTGCACTTTCTGCCGAGACTTATCTAAACCAGAAGTTGAATATGA  2755
AF119042     AAGTGGAGAGTGGATTTGCACTTTCTGCCGAGACTTATCTAAACCAGAAGTTGAATATGA  2656
AK127592     AACAGAAGGGTAGGTTAGA---TGCTATTAAGAAGGCACTTAATAGTACATCATGTAAGA  2377
             **  *  ** **  ** **      ****    ** * *  ** **  **  **  * *
                                                          sirna_103484
NM_015905    TTGTGATGCTCCCAGTCACAACTCAGAAAAAAAGAAAACTGAAGGCCTTGTTAAGTTAAC  2917
NM_003852    TTGTGATGCTCCCAGTCACAACTCAGAAAAAAAGAAAACTGAAGGCCTTGTTAAGTTAAC  2815
AF009353     TTGTGATGCTCCCAGTCACAACTCAGAAAAAAAGAAAACTGAAGGCCTTGTTAAGTTAAC  2588
BC028689     TTCTGATGCTCCCAGTCACAACTCAGAAAAAAAGAAAACTGAAGGCCTTGTTAAGTTAAC  2815
AF119042     TTGTGATGCTCCCAGTCACAACTCAGAAAAAAAGAAAACTGAAGGCCTTGTTAAGTTAAC  2716
AK127592     TGGCAACTGTATTAAAGAAAAATCCGGAAAACAAATGTTTGATTTTTGTTTTTGTTTTTA  2437
             *  *  *      *  *        *    **  *     ***        ***    **
```

FIG. 9G

```
NM_015905    ACCTATAGATAAAAGGAAGTGTGAGCGCCTACTTTTATTTCTTTACTGCCATGAAATGAG 2977
NM_003852    ACCTATAGATAAAAGGAAGTGTGAGCGCCTACTTTTATTTCTTTACTGCCATGAAATGAG 2875
AF009353     ACCTATAGATAAAAGGAAGTGTGAGCGCCTACTTTTATTTCTTTACTGCCATGAAATGAG 2648
BC028689     ACCTATAGATAAAAGGAAGTGTGAGCGCCTACTTTTATTTCTTTACTGCCATGAAATGAG 2875
AF119042     ACCTATAGATAAAAGGAAGTGTGAGCGCCTACTTTTATTTCTTTACTGCCATGAAATGAG 2776
AK127592     TCTTGTCTGTAGAGGTATTTTGGTATAGCAGGTTTT-------CAAGGCCGTTTTTTATA 2490
              *  *   ** *  *    *      ****          *  ***  *        *

NM_015905    CCTGGCTTTTCAAGACCCTGTTCCTCTAACTGTGCCTGATTATTACAAAATAATTAAAAA 3037
NM_003852    CCTGGCTTTTCAAGACCCTGTTCCTCTAACTGTGCCTGATTATTACAAAATAATTAAAAA 2935
AF009353     CCTGGCTTTTCAAGACCCTGTTCCTCTAACTGTGCCTGATTATTACAAAATAATTAAAAA 2708
BC028689     CCTGGCTTTTCAAGACCCTGTTCCTCTAACTGTGCCTGATTATTACAAAATAATTAAAAA 2935
AF119042     CCTGGCTTTTCAAGACCCTGTTCCTCTAACTGTGCCTGATTATTACAAAATAATTAAAAA 2836
AK127592     CAT-----TTCTAGATCTAGATTTTCAACTTCTTCC-----ACTGAGGGAAGTATATACA 2540
             * *      ***  ***  *  *   *  ** *    *  **         **  *  *

NM_015905    TCCAATGGATTTGTCAACCATCAAGAAAAGACT--ACAAGAAGATTATTCCATGTACTCA 3095
NM_003852    TCCAATGGATTTGTCAACCATCAAGAAAAGACT--ACAAGAAGATTATTCCATGTACTCA 2993
AF009353     TCCAATGGATTTGTCAACCATCAAGAAAAGACT--ACAAGAAGATTATTCCATGTACTCA 2766
BC028689     TCCAATGGATTTGTCAACCATCAAGAAAAGACT--ACAAGAAGATTATTCCATGTACTCA 2993
AF119042     TCCAATGGATTTGTCAACCATCAAGAAAAGACT--ACAAGAAGATTATTCCATGTACTCA 2894
AK127592     TT---TGGGTTTGCTGTGTGTCTATGTGAGGTTTAATTGTACAGGTGATCCTTTTACAAC 2597
             *    *** ****      **  *      **   *          *  * *** * ***

NM_015905    AAACCTGAAGATTTTGTAGCTGATTTTAGATTGATCTTTCAAAACTGTGCTGAATTCAAT 3155
NM_003852    AAACCTGAAGATTTTGTAGCTGATTTTAGATTGATCTTTCAAAACTGTGCTGAATTCAAT 3053
AF009353     AAACCTGAAGATTTTGTACGTGATTTTAGATTGATCTTTCAAAACTGTGCTGAATTCAAT 2826
BC028689     AAACCTGAAGATTTTGTAGCTGATTTTAGATTGATCTTTCAAAACTGTGCTGAATTCAAT 3053
AF119042     AAACCTGAAGATTTTGTAGCTGATTTTAGATTGATCTTTCAAAACTGTGCTGAATTCAAT 2954
AK127592     AAGCCTCATTGTTTGCAGTATAGCTTTTAGTGGAACTACCCAAAATATAAAATACAGGGA 2657
             ** ***  *  ***    ***    * *** * ** **  ****** *  *       *

NM_015905    GAGCCTGATTCAGAAGTAGCCAATGCTGGT-ATAAAACTTGAAAATTATTTTGAAGAACT 3214
NM_003852    GAGCCTGATTCAGAAGTAGCCAATGCTGGT-ATAAAACTTGAAAATTATTTTGAAGAACT 3112
AF009353     GAGCCTGATTCAGAAGTAGCCAATGCTGGT-ATAAAACTTGAAAATTATTTTGAAGAACT 2885
BC028689     GAGCCTGATTCAGAAGTAGCCAATGCTGGT-ATAAAACTTGAAAATTATTTTGAAGAACT 3112
AF119042     GAGCCTGATTCAGAAGTAGCCAATGCTGGT-ATAAAACTTGAAAATTATTTTGAAGAACT 3013
AK127592     GAAAATAACTTGTTAGCAATAGATCCCCATTGTTTATATATATAGGTCTTGTTCATAATA 2717
             **    * *   **     * *  *  * *    *  *  *  *   * *  ** * **

NM_015905    TCTAAAGAACCTCTATCCAGAAAAAAGGTTTCCCAAACCAGAATTCAGGAATGAATCAGA 3274
NM_003852    TCTAAAGAACCTCTATCCAGAAAAAAGGTTTCCCAAACCAGAATTCAGGAATGAATCAGA 3172
AF009353     TCTAAAGAACCTCTATCCAGAAAAAAGGTTTCCCAAACCAGAATTCAGGAATGAATCAGA 2945
BC028689     TCTAAAGAACCTCTATCCAGAAAAAAGGTTTCCCAAACCAGAATTCAGGAATGAATCAGA 3172
AF119042     TCTAAAGAACCTCTATCCAGAAAAAAGGTTTCCCAAACCAGAATTCAGGAATGAATCAGA 3073
AK127592     TGTCAA----TTATGTATTGTTAAAAAGT---CCTACTCACTTTTCAAATATGTGTTACA 2770
             * * **     * *  *    *****      **     *  ****   ***   * *

NM_015905    AGATAATAAATTTAGTGATGATTCAGATGATGACTTTGTACA---GCCCCGGAAGAAACG 3331
NM_003852    AGATAATAAATTTAGTGATGATTCAGATGATGACTTTGTACA---GCCCCGGAAGAAACG 3229
AF009353     AGATAATAAATTTAGTGATGATTCAGATGATGACTTTGTACA---GCCCCGGAAGAAACG 3002
BC028689     AGATAATAAATTTAGTGATGATTCAGATGATGACTTTGTACA---GCCCCGGAAGAAACG 3229
AF119042     AGATAATAAATTTAGTGATGATTCAGATGATGACTTTGTACA---GCCCCGGAAGAAACG 3130
AK127592     TGGTAATGTTTGTCATTGTTGTTTTAAAGTTGCATTTG-ACATTTGTTCTCCAAAGAGTG 2829
              * ****  *  *   * *  *    *    * *** ** *    * *   * ** * *
```

FIG. 9H

```
NM_015905    CCTCAAAAGCATTGAAGAACGCCAGTTGCTTAAATAATATGCAGCACCACTAGCTTGTGC  3391
NM_003852    CCTCAAAAGCATTGAAGAACGCCAGTTGCTTAAATAATATGCAGCACCACTAGCTTGTGC  3289
AF009353     CCTCAAAAGCATTGAAGAACGCCAGTTGCTTAAATAA-----------------------  3039
BC028689     CCTCAAAAGCATTGAAGAACGCCAGTTGCTTAAATAATATGCAGCACCACTAGCTTGTGC  3289
AF119042     CCTCAAAAGCATTGAAGAACGCCAGTTGCTTAAATAATATGCAGCACCACTAGCTTGTGC  3190
AK127592     TTTGAACAGATTTTGATAACAGTGC-----------------------------------  2854
              * ** **   **    *  ***

NM_015905    TGGTTTTTAGATTTTTTTGTTTTCAAAAAAACATTTGTCAGTAATTTAACATCACTACAA  3451
NM_003852    TGGTTTTTAGATTTTTTTGTTTTCAAAAAAACATTTGTCAGTAATTTAACATCACTACAA  3349
AF009353     ------------------------------------------------------------
BC028689     TGGTTTTTAGATTTTTTTGTTTTCAAAAAAACATTTGTCAGTAATTTAACATCACTACAA  3349
AF119042     TGGTTTTTAGATTTTTTTGTTTTCAAAAAAACATTTGTCAGTAATTTAACATCACTACAA  3250
AK127592     ------------------------------------------------------------

NM_015905    AAAGAAG-AGTTTGTGACTATTCTCATCTCTGTTTTGGACGTTTAC----TAGACTTTGA  3506
NM_003852    AAAGAAG-AGTTTGTGACTATTCTCATCTCTGTTTTGGACGTTTAC----TAGACTTTGA  3404
AF009353     ------------------------------------------------------------
BC028689     AAAGAAG-AGTTTGTGACTATTCTCATCTCTGTTTTGGACGTTTAC----TAGACTTTGA  3404
AF119042     AAAGAAGGAGTTTGTGACTATTCTCATCTCTGTTTTGCAGGTTTACGCCGCACACTTTGA  3310
AK127592     ------------------------------------------------------------

NM_015905    TTTCCTTAATAGCCCATTTCTGTTAACCTCTTATCACTAAGAAAGAAAGGAAAGAAGGAG  3566
NM_003852    TTTCCTTAATAGCCCATTTCTGTTAACCTCTTATCACTAAGAAAGAAAGGAAAGAAGGAG  3464
AF009353     ------------------------------------------------------------
BC028689     TTTCCTTAATAGCCCATTTCTGTTAACCTCTTATCACTAAGAAAGAAAGGAAAGAAGGAG  3464
AF119042     TTTCCTTAATAGCCCATTTCTGTTAACCTATTATCACTAAGAAAGAAAGGAAAGAAGGAG  3370
AK127592     ------------------------------------------------------------

NM_015905    ATGAATAGAAGAAAGAAAATGGAAAGAAGGAAAAAAGGAGGATAGAAAAAGGATGGAAGA  3626
NM_003852    ATGAATAGAAGAAAGAAAATGGAAAGAAGGAAAAAAGGAGGATAGAAAAAGGATGGAAGA  3524
AF009353     ------------------------------------------------------------
BC028689     ATGAATAGAAGAAAGAAAATGGAAAGAAGGAAAAAAGGAGGATAGAAAAAGGATGGAAGA  3524
AF119042     ATGAATAGAAGAAAGAAAATGGAAAGAAGGAAAAAAGGAGGATTGAAAAAGGATGGAAGA  3430
AK127592     ------------------------------------------------------------

NM_015905    AAGAAGC-ATTGAAAACAAAGACATTCTTCCCACTTCTTGGATTTTTAAACCACAGTCTG  3685
NM_003852    AAGAAGC-ATTGAAAACAAAGACATTCTTCCCACTTCTTGGATTTTTAAACCACAGTCTG  3583
AF009353     ------------------------------------------------------------
BC028689     AAGAAGC-ATTGAAAACAAAGACATTCTTCCCACTTCTTGGATTTTTAAACCACAGTCTG  3583
AF119042     AAGAAGCCATTGAAAACAAAGACATTCTTCCCACTTCTTGGATTTTTAAACCACAGTCTG  3490
AK127592     ------------------------------------------------------------

NM_015905    GAGTGATAGCTACTGTAGAAAGGAAATAGACTTTGTATGAACTCTTTAAGTTGAAAAGTA  3745
NM_003852    GAGTGATAGCTACTGTAGAAAGGAAATAGACTTTGTATGAACTCTTTAAGTTGAAAAGTA  3643
AF009353     ------------------------------------------------------------
BC028689     GAGTGATAGCTACTGTAGAAAGGAAATAGACTTTGTATGAACTCTTTAAGTTGAAAAGTA  3643
AF119042     GAGTGATAGCTACTGTAGAAAGGAAATAGACTTT-TATGAACTCTTTAAGTTGAAAAGTA  3549
AK127592     ------------------------------------------------------------
```

FIG. 9I

```
NM_015905   AAAAATATATGTGGTTTGGATGTGTGCTTTAATTCAGCTTTAGAAATTAATACCACTACC 3805
NM_003852   AAAAATATATGTGGTTTGGATGTGTGCTTTAATTCAGCTTTAGAAATTAATACCACTACC 3703
AF009353    ------------------------------------------------------------
BC028689    AAAAATATATGTGGTTTGGATGTGTGCTTTAATTCAGCTTTAGAAATTAATACCACTACC 3703
AF119042    AAAAATATATGTGGTTTGGATGTGTGCTTTAATTCAGCTTTAGAAATTAATACCACTACC 3609
AK127592    ------------------------------------------------------------

NM_015905   CGTGAATTATATGGCCTGACAATATGAATTAGGTGTACTGTACTGAAGAACAGTACTCCA 3865
NM_003852   CGTGAATTATATGGCCTGACAATATGAATTAGGTGTACTGTACTGAAGAACAGTACTCCA 3763
AF009353    ------------------------------------------------------------
BC028689    CGTGAATTATATGGCCTGACAATATGAATTAGGTGTACTGTACTGAAGAACAGTACTCCA 3763
AF119042    CGTGAATTATATGGCCTGACAATATGAATTAGGTGTACTGTACTGAAGAACAGTACTCCA 3669
AK127592    ------------------------------------------------------------

NM_015905   CAAACATGGGTGGTAACAAGAGTTCCATCCCAGGAGGCCAAACGGTGCAACAGAAGGGTA 3925
NM_003852   CAAACATGGGTGGTAACAAGAGTTCCATCCCAGGAGGCCAAACGGTGCAACAGAAGGGTA 3823
AF009353    ------------------------------------------------------------
BC028689    CAAACATGGGTGGTAACAAGAGTTCCATCCCAGGAGGCCAAACGGTGCAACAGAAGGGTA 3823
AF119042    CAAACATGGGTGGTAACAAGAGTTCCATCCCAGGAGGCCAAACGGTGCAACAGAAGGGTA 3729
AK127592    ------------------------------------------------------------

NM_015905   GGTTAGATGCTATTAAGAAGGCACTTAATAGTACATCATGTAAGATGGCAACTGTATTAA 3985
NM_003852   GGTTAGATGCTATTAAGAAGGCACTTAATAGTACATCATGTAAGATGGCAACTGTATTAA 3883
AF009353    ------------------------------------------------------------
BC028689    GGTTAGATGCTATTAAGAAGGCACTTAATAGTACATCATGTAAGATGGCAACTGTATTAA 3883
AF119042    GGTTAGATGCTATTAAGAAGGCACTTAATAGTACATCATGTAAGATGGCAACTGTATTAA 3789
AK127592    ------------------------------------------------------------

NM_015905   AGAAAAATCCGGAAAACAAAAA---- 4007
NM_003852   AGAAAAATCCGGAAAACAAAAA---- 3905
AF009353    --------------------------
BC028689    AGAAAAATCCGAAAAAAAAAAAAAAA 3909
AF119042    AGAAAAATCCGGAAAACG-------- 3807
AK127592    --------------------------
```

| SEQ ID NOs: | Transcript accession nos: | Sense sequence | Antisense sequence |
|---|---|---|---|
| 27 & 36 | NM 003852, NM 015905 | GGAAAUCAGAUCCAAAACATT | UGUUUUGGAUCUGAUUUCCTG |
| 28 & 37 | NM 003852, NM 015905 | CCCAAGUUGGAGUCAUUCGTT | CGAAUGACUCCAACUUGGGTG |
| 29 & 38 | NM 003852, NM 015905 | GGUAUGUACAAGCUGUGAGTT | CUCACAGCUUGUACAUACCTG |
| 30 & 39 | NM 003852, NM 015905 | GGACAACGCAGAAGCCAAUTT | AUUGGCUUCUGCGUUGUCCTC |
| 31 & 40 | NM 003852, NM 015305 | GGCCUUGUUAAGUUAACACTT | GUGUUAACUUAACAAGGCCTT |
| 32 & 41 | NM 003852, NM 015905 | GGUGGAACAGGAUAUUAAATT | UUUAAUAUCCUGUUCCACCTG |
| 33 & 42 | NM 003S52, NM 015905 | GAACGGUCCAGUCACCAAATT | UUUGGUGACUGGACCGUUCTG |
| 34 & 43 | NM 003852, NM 015905 | GUCAGUUGUUAGAACAUAATT | UUAUGUUCUAACAACUGACAG |
| 35 & 44 | NM 003852, NM 015905 | CGACUGAUUACAUACCGGUTT | ACCGGUAUGUAAUCAGUCGTT |

SEQUENCE LISTING

<160> NUMBER OF SEQ ID NOS: 64

<210> SEQ ID NO 1
<211> LENGTH: 4007
<212> TYPE: DNA
<213> ORGANISM: Homo sapiens
<220> FEATURE:
<221> NAME/KEY: CDS
<222> LOCATION: (216)..(3368)

<400> SEQUENCE: 1

```
gacagatacc ctccttccgg ccgcgccact cgggaggcgg atcccgtggg cctgaggagg      60
cttcccccgc ccggtttgct ttccctccct cgctggcgct gccgcgagtc caccgagcgg     120
cctctgagga gcagccgcag gaggaggagg aggtcgtcgg gggcggcggg cggagaccgc     180
gctctcgctt ccccggcggc ggcaagggca ggaca atg gag gtg gcg gtg gag        233
                                      Met Glu Val Ala Val Glu
                                       1               5 aag gcg gtg gcg gcg gcg gca gcg gcc tcg gct gcg gcc tcc ggg ggg       281
Lys Ala Val Ala Ala Ala Ala Ala Ala Ser Ala Ala Ala Ser Gly Gly
             10                  15                  20 ccc tcg gcg gcg ccg agc ggg gag aac gag gcc gag agt cgg cag ggc       329
Pro Ser Ala Ala Pro Ser Gly Glu Asn Glu Ala Glu Ser Arg Gln Gly
         25                  30                  35 ccg gac tcg gag cgc ggc ggc gag gcg gcc cgg ctc aac ctg ttg gac       377
Pro Asp Ser Glu Arg Gly Gly Glu Ala Ala Arg Leu Asn Leu Leu Asp
     40                  45                  50 act tgc gcc gtg tgc cac cag aac atc cag agc cgg gcg ccc aag ctg       425
Thr Cys Ala Val Cys His Gln Asn Ile Gln Ser Arg Ala Pro Lys Leu
 55                  60                  65                  70 ctg ccc tgc ctg cac tct ttc tgc cag cgc tgc ctg ccc gcg ccc cag       473
Leu Pro Cys Leu His Ser Phe Cys Gln Arg Cys Leu Pro Ala Pro Gln
                 75                  80                  85 cgc tac ctc atg ctg ccc gcg ccc atg ctg ggc tcg gcc gag acc ccg       521
Arg Tyr Leu Met Leu Pro Ala Pro Met Leu Gly Ser Ala Glu Thr Pro
             90                  95                 100 cca ccc gtc cct gcc ccc ggc tcg ccg gtc agc ggc tcg tcg ccg ttc       569
Pro Pro Val Pro Ala Pro Gly Ser Pro Val Ser Gly Ser Ser Pro Phe
         105                 110                 115 gcc acc caa gtt gga gtc att cgt tgc cca gtt tgc agc caa gaa tgt       617
Ala Thr Gln Val Gly Val Ile Arg Cys Pro Val Cys Ser Gln Glu Cys
     120                 125                 130 gca gag aga cac atc ata gat aac ttt ttt gtg aag gac act act gag       665
Ala Glu Arg His Ile Ile Asp Asn Phe Phe Val Lys Asp Thr Thr Glu
135                 140                 145                 150 gtt ccc agc agt aca gta gaa aag tca aat cag gta tgt aca agc tgt       713
Val Pro Ser Ser Thr Val Glu Lys Ser Asn Gln Val Cys Thr Ser Cys
                 155                 160                 165 gag gac aac gca gaa gcc aat ggg ttt tgt gta gag tgt gtt gaa tgg       761
Glu Asp Asn Ala Glu Ala Asn Gly Phe Cys Val Glu Cys Val Glu Trp
             170                 175                 180 ctc tgc aag acg tgt atc aga gct cat cag agg gta aag ttc aca aaa       809
Leu Cys Lys Thr Cys Ile Arg Ala His Gln Arg Val Lys Phe Thr Lys
         185                 190                 195 gac cac act gtc aga cag aaa gag gaa gta tct cca gag gca gtt ggt       857
Asp His Thr Val Arg Gln Lys Glu Glu Val Ser Pro Glu Ala Val Gly
     200                 205                 210 gtc acc agc cag cga cca gtg ttt tgt cct ttt cat aaa aag gag cag       905
Val Thr Ser Gln Arg Pro Val Phe Cys Pro Phe His Lys Lys Glu Gln
215                 220                 225                 230
```

```
ctg aag ctg tac tgt gag aca tgt gac aaa ctg aca tgt cga gac tgt      953
Leu Lys Leu Tyr Cys Glu Thr Cys Asp Lys Leu Thr Cys Arg Asp Cys
            235                 240                 245 cag ttg tta gaa cat aaa gag cat aga tac caa ttt ata gaa gaa gct     1001
Gln Leu Leu Glu His Lys Glu His Arg Tyr Gln Phe Ile Glu Glu Ala
            250                 255                 260 ttt cag aat cag aaa gtg atc ata gat aca cta atc acc aaa ctg atg     1049
Phe Gln Asn Gln Lys Val Ile Ile Asp Thr Leu Ile Thr Lys Leu Met
            265                 270                 275 gaa aaa aca aaa tac ata aaa ttc aca gga aat cag atc caa aac aga     1097
Glu Lys Thr Lys Tyr Ile Lys Phe Thr Gly Asn Gln Ile Gln Asn Arg
            280                 285                 290 att att gaa gta aat caa aat caa aag cag gtg gaa cag gat att aaa     1145
Ile Ile Glu Val Asn Gln Asn Gln Lys Gln Val Glu Gln Asp Ile Lys
295                 300                 305                 310 gtt gct ata ttt aca ctg atg gta gaa ata aat aaa aaa gga aaa gct     1193
Val Ala Ile Phe Thr Leu Met Val Glu Ile Asn Lys Lys Gly Lys Ala
                315                 320                 325 cta ctg cat cag tta gag agc ctt gca aag gac cat cgc atg aaa ctt     1241
Leu Leu His Gln Leu Glu Ser Leu Ala Lys Asp His Arg Met Lys Leu
            330                 335                 340 atg caa caa caa cag gaa gtg gct gga ctc tct aaa caa ttg gag cat     1289
Met Gln Gln Gln Gln Glu Val Ala Gly Leu Ser Lys Gln Leu Glu His
            345                 350                 355 gtc atg cat ttt tct aaa tgg gca gtt tcc agt ggc agc agt aca gca     1337
Val Met His Phe Ser Lys Trp Ala Val Ser Ser Gly Ser Ser Thr Ala
            360                 365                 370 tta ctt tat agc aaa cga ctg att aca tac cgg tta cgg cac ctc ctt     1385
Leu Leu Tyr Ser Lys Arg Leu Ile Thr Tyr Arg Leu Arg His Leu Leu
375                 380                 385                 390 cgt gca agg tgt gat gca tcc cca gtg acc aac aac acc atc caa ttt     1433
Arg Ala Arg Cys Asp Ala Ser Pro Val Thr Asn Asn Thr Ile Gln Phe
                395                 400                 405 cac tgt gat cct agt ttc tgg gct caa aat atc atc aac tta ggt tct     1481
His Cys Asp Pro Ser Phe Trp Ala Gln Asn Ile Ile Asn Leu Gly Ser
            410                 415                 420 tta gta atc gag gat aaa gag agc cag cca caa atg cct aag cag aat     1529
Leu Val Ile Glu Asp Lys Glu Ser Gln Pro Gln Met Pro Lys Gln Asn
            425                 430                 435 cct gtc gtg gaa cag aat tca cag cca cca agt ggt tta tca tca aac     1577
Pro Val Val Glu Gln Asn Ser Gln Pro Pro Ser Gly Leu Ser Ser Asn
440                 445                 450 cag tta tcc aag ttc cca aca cag atc agc cta gct caa tta cgg ctc     1625
Gln Leu Ser Lys Phe Pro Thr Gln Ile Ser Leu Ala Gln Leu Arg Leu
455                 460                 465                 470 cag cat atg cag caa cag gta atg gct cag agg caa cag gtg caa cgg     1673
Gln His Met Gln Gln Gln Val Met Ala Gln Arg Gln Gln Val Gln Arg
                475                 480                 485 agg cca gca cct gtg ggt tta cca aac cct aga atg cag ggg ccc atc     1721
Arg Pro Ala Pro Val Gly Leu Pro Asn Pro Arg Met Gln Gly Pro Ile
            490                 495                 500 cag caa cct tcc atc tct cat cag caa ccg cct cca cgt ttg ata aac     1769
Gln Gln Pro Ser Ile Ser His Gln Gln Pro Pro Pro Arg Leu Ile Asn
            505                 510                 515 ttt cag aat cac agc ccc aaa ccc aat gga cca gtt ctt cct cct cat     1817
Phe Gln Asn His Ser Pro Lys Pro Asn Gly Pro Val Leu Pro Pro His
            520                 525                 530 cct caa caa ctg aga tat cca cca aac cag aac ata cca cga caa gca     1865
Pro Gln Gln Leu Arg Tyr Pro Pro Asn Gln Asn Ile Pro Arg Gln Ala
535                 540                 545                 550
```

| | | | | | | | | | | | | | | | |
|---|---|---|---|---|---|---|---|---|---|---|---|---|---|---|---|
|ata|aag|cca|aac|ccc|cta|cag|atg|gct|ttc|ttg|gct|caa|caa|gcc|ata|1913|
|Ile|Lys|Pro|Asn|Pro|Leu|Gln|Met|Ala|Phe|Leu|Ala|Gln|Gln|Ala|Ile| |
| | | |555| | | |560| | | | |565| | | | |

| | | | | | | | | | | | | | | | |
|---|---|---|---|---|---|---|---|---|---|---|---|---|---|---|---|
|aaa|cag|tgg|cag|atc|agc|agt|gga|cag|gga|acc|cca|tca|act|acc|aac|1961|
|Lys|Gln|Trp|Gln|Ile|Ser|Ser|Gly|Gln|Gly|Thr|Pro|Ser|Thr|Thr|Asn| |
| | | |570| | | |575| | | | |580| | | | | agc aca tcc tct act cct tcc agc ccc acg att act agt gca gca gga  2009
Ser Thr Ser Ser Thr Pro Ser Pro Thr Ile Thr Ser Ala Ala Gly
        585             590             595 tat gat gga aag gct ttt ggt tca cct atg atc gat ttg agc tca cca  2057
Tyr Asp Gly Lys Ala Phe Gly Ser Pro Met Ile Asp Leu Ser Ser Pro
    600             605             610 gtg gga ggg tct tat aat ctt ccc tct ctt ccg gat att gac tgt tca  2105
Val Gly Gly Ser Tyr Asn Leu Pro Ser Leu Pro Asp Ile Asp Cys Ser
615             620             625             630 agt act att atg ctg gac aat att gtg agg aaa gat act aat ata gat  2153
Ser Thr Ile Met Leu Asp Asn Ile Val Arg Lys Asp Thr Asn Ile Asp
            635             640             645 cat ggc cag cca aga cca ccc tca aac aga acg gtc cag tca cca aat  2201
His Gly Gln Pro Arg Pro Pro Ser Asn Arg Thr Val Gln Ser Pro Asn
        650             655             660 tca tca gtg cca tct cca ggc ctt gca gga cct gtt act atg act agt  2249
Ser Ser Val Pro Ser Pro Gly Leu Ala Gly Pro Val Thr Met Thr Ser
    665             670             675 gta cac ccc cca ata cgt tca cct agt gcc tcc agc gtt gga agc cga  2297
Val His Pro Pro Ile Arg Ser Pro Ser Ala Ser Ser Val Gly Ser Arg
680             685             690 gga agc tct ggc tct tcc agc aaa cca gca gga gct gac tct aca cac  2345
Gly Ser Ser Gly Ser Ser Ser Lys Pro Ala Gly Ala Asp Ser Thr His
695             700             705             710 aaa gtc cca gtg gtc atg ctg gag cca att cga ata aaa caa gaa aac  2393
Lys Val Pro Val Val Met Leu Glu Pro Ile Arg Ile Lys Gln Glu Asn
            715             720             725 agt gga cca ccg gaa aat tat gat ttc cct gtt gtt ata gtg aag caa  2441
Ser Gly Pro Pro Glu Asn Tyr Asp Phe Pro Val Val Ile Val Lys Gln
        730             735             740 gaa tca gat gaa gaa tct agg cct caa aat gcc aat tat cca aga agc  2489
Glu Ser Asp Glu Glu Ser Arg Pro Gln Asn Ala Asn Tyr Pro Arg Ser
    745             750             755 ata ctc acc tcc ctg ctc tta aat agc agt cag agc tct act tct gag  2537
Ile Leu Thr Ser Leu Leu Leu Asn Ser Ser Gln Ser Ser Thr Ser Glu
760             765             770 gag act gtg cta aga tca gat gcc cct gat agt aca gga gat caa cct  2585
Glu Thr Val Leu Arg Ser Asp Ala Pro Asp Ser Thr Gly Asp Gln Pro
775             780             785             790 gga ctt cac cag gac aat tcc tca aat gga aag tct gaa tgg ttg gat  2633
Gly Leu His Gln Asp Asn Ser Ser Asn Gly Lys Ser Glu Trp Leu Asp
            795             800             805 cct tcc cag aag tca cct ctt cat gtt gga gag aca agg aaa gag gat  2681
Pro Ser Gln Lys Ser Pro Leu His Val Gly Glu Thr Arg Lys Glu Asp
        810             815             820 gac ccc aat gag gac tgg tgt gca gtt tgt caa aac gga ggg gaa ctc  2729
Asp Pro Asn Glu Asp Trp Cys Ala Val Cys Gln Asn Gly Gly Glu Leu
    825             830             835 ctc tgc tgt gaa aag tgc ccc aaa gta ttc cat ctt tct tgt cat gtg  2777
Leu Cys Cys Glu Lys Cys Pro Lys Val Phe His Leu Ser Cys His Val
840             845             850 ccc aca ttg aca aat ttt cca agt gga gag tgg att tgc act ttc tgc  2825
Pro Thr Leu Thr Asn Phe Pro Ser Gly Glu Trp Ile Cys Thr Phe Cys
855             860             865             870

```
cga gac tta tct aaa cca gaa gtt gaa tat gat tgt gat gct ccc agt    2873
Arg Asp Leu Ser Lys Pro Glu Val Glu Tyr Asp Cys Asp Ala Pro Ser
            875                 880                 885 cac aac tca gaa aaa aag aaa act gaa ggc ctt gtt aag tta aca cct    2921
His Asn Ser Glu Lys Lys Lys Thr Glu Gly Leu Val Lys Leu Thr Pro
            890                 895                 900 ata gat aaa agg aag tgt gag cgc cta ctt tta ttt ctt tac tgc cat    2969
Ile Asp Lys Arg Lys Cys Glu Arg Leu Leu Leu Phe Leu Tyr Cys His
            905                 910                 915 gaa atg agc ctg gct ttt caa gac cct gtt cct cta act gtg cct gat    3017
Glu Met Ser Leu Ala Phe Gln Asp Pro Val Pro Leu Thr Val Pro Asp
            920                 925                 930 tat tac aaa ata att aaa aat cca atg gat ttg tca acc atc aag aaa    3065
Tyr Tyr Lys Ile Ile Lys Asn Pro Met Asp Leu Ser Thr Ile Lys Lys
935                 940                 945                 950 aga cta caa gaa gat tat tcc atg tac tca aaa cct gaa gat ttt gta    3113
Arg Leu Gln Glu Asp Tyr Ser Met Tyr Ser Lys Pro Glu Asp Phe Val
            955                 960                 965 gct gat ttt aga ttg atc ttt caa aac tgt gct gaa ttc aat gag cct    3161
Ala Asp Phe Arg Leu Ile Phe Gln Asn Cys Ala Glu Phe Asn Glu Pro
            970                 975                 980 gat tca gaa gta gcc aat gct ggt ata aaa ctt gaa aat tat ttt gaa    3209
Asp Ser Glu Val Ala Asn Ala Gly Ile Lys Leu Glu Asn Tyr Phe Glu
            985                 990                 995 gaa ctt cta aag aac ctc tat cca gaa aaa agg ttt ccc aaa cca        3254
Glu Leu Leu Lys Asn Leu Tyr Pro Glu Lys Arg Phe Pro Lys Pro
            1000                1005                1010 gaa ttc agg aat gaa tca gaa gat aat aaa ttt agt gat gat tca        3299
Glu Phe Arg Asn Glu Ser Glu Asp Asn Lys Phe Ser Asp Asp Ser
            1015                1020                1025 gat gat gac ttt gta cag ccc cgg aag aaa cgc ctc aaa agc att        3344
Asp Asp Asp Phe Val Gln Pro Arg Lys Lys Arg Leu Lys Ser Ile
1030                1035                1040 gaa gaa cgc cag ttg ctt aaa taa tatgcagcac cactagcttg              3388
Glu Glu Arg Gln Leu Leu Lys
            1045                1050 tgctggtttt tagattttt tgttttcaaa aaacatttg tcagtaattt aacatcacta    3448
caaaaagaag agtttgtgac tattctcatc tctgttttgg acgtttacta gactttgatt  3508
tccttaatag cccatttctg ttaacctctt atcactaaga agaaaggaa agaaggagat   3568 gaatagaaga aagaaaatgg aaagaaggaa aaaggagga tagaaaaagg atggaagaaa   3628
gaagcattga aaacaaagac attcttccca cttcttggat ttttaaacca cagtctggag  3688
tgatagctac tgtagaaagg aaatagactt tgtatgaact cttaagttg aaaagtaaaa   3748 aatatatgtg gtttggatgt gtgctttaat tcagctttag aaattaatac cactacccgt  3808
gaattatatg gcctgacaat atgaattagg tgtactgtac tgaagaacag tactccacaa  3868
acatgggtgg taacaagagt tccatcccag gaggccaaac ggtgcaacag aagggtaggt  3928
tagatgctat taagaaggca cttaatagta catcatgtaa gatggcaact gtattaaaga  3988
aaaatccgga aaacaaaaa                                               4007

<210> SEQ ID NO 2
<211> LENGTH: 1050
<212> TYPE: PRT
<213> ORGANISM: Homo sapiens

<400> SEQUENCE: 2

Met Glu Val Ala Val Glu Lys Ala Val Ala Ala Ala Ala Ala Ala Ser
```

-continued

```
1               5               10              15
Ala Ala Ala Ser Gly Gly Pro Ser Ala Pro Ser Gly Glu Asn Glu
                20              25              30
Ala Glu Ser Arg Gln Gly Pro Asp Ser Glu Arg Gly Gly Glu Ala Ala
            35              40              45
Arg Leu Asn Leu Leu Asp Thr Cys Ala Val Cys His Gln Asn Ile Gln
50              55              60
Ser Arg Ala Pro Lys Leu Leu Pro Cys Leu His Ser Phe Cys Gln Arg
65              70              75              80
Cys Leu Pro Ala Pro Gln Arg Tyr Leu Met Leu Pro Ala Pro Met Leu
            85              90              95
Gly Ser Ala Glu Thr Pro Pro Val Pro Ala Pro Gly Ser Pro Val
                100             105             110
Ser Gly Ser Ser Pro Phe Ala Thr Gln Val Gly Val Ile Arg Cys Pro
            115             120             125
Val Cys Ser Gln Glu Cys Ala Glu Arg His Ile Ile Asp Asn Phe Phe
            130             135             140
Val Lys Asp Thr Thr Glu Val Pro Ser Ser Thr Val Glu Lys Ser Asn
145             150             155             160
Gln Val Cys Thr Ser Cys Glu Asp Asn Ala Glu Ala Asn Gly Phe Cys
                165             170             175
Val Glu Cys Val Glu Trp Leu Cys Lys Thr Cys Ile Arg Ala His Gln
                180             185             190
Arg Val Lys Phe Thr Lys Asp His Thr Val Arg Gln Lys Glu Glu Val
            195             200             205
Ser Pro Glu Ala Val Gly Val Thr Ser Gln Arg Pro Val Phe Cys Pro
            210             215             220
Phe His Lys Lys Glu Gln Leu Lys Leu Tyr Cys Glu Thr Cys Asp Lys
225             230             235             240
Leu Thr Cys Arg Asp Cys Gln Leu Leu Glu His Lys Glu His Arg Tyr
                245             250             255
Gln Phe Ile Glu Glu Ala Phe Gln Asn Gln Lys Val Ile Ile Asp Thr
                260             265             270
Leu Ile Thr Lys Leu Met Glu Lys Thr Lys Tyr Ile Lys Phe Thr Gly
            275             280             285
Asn Gln Ile Gln Asn Arg Ile Ile Glu Val Asn Gln Asn Gln Lys Gln
            290             295             300
Val Glu Gln Asp Ile Lys Val Ala Ile Phe Thr Leu Met Val Glu Ile
305             310             315             320
Asn Lys Lys Gly Lys Ala Leu Leu His Gln Leu Glu Ser Leu Ala Lys
                325             330             335
Asp His Arg Met Lys Leu Met Gln Gln Gln Glu Val Ala Gly Leu
                340             345             350
Ser Lys Gln Leu Glu His Val Met His Phe Ser Lys Trp Ala Val Ser
            355             360             365
Ser Gly Ser Ser Thr Ala Leu Leu Tyr Ser Lys Arg Leu Ile Thr Tyr
            370             375             380
Arg Leu Arg His Leu Leu Arg Ala Arg Cys Asp Ala Ser Pro Val Thr
385             390             395             400
Asn Asn Thr Ile Gln Phe His Cys Asp Pro Ser Phe Trp Ala Gln Asn
                405             410             415
Ile Ile Asn Leu Gly Ser Leu Val Ile Glu Asp Lys Glu Ser Gln Pro
            420             425             430
```

```
Gln Met Pro Lys Gln Asn Pro Val Glu Gln Asn Ser Gln Pro Pro
        435                 440                 445

Ser Gly Leu Ser Ser Asn Gln Leu Ser Lys Phe Pro Thr Gln Ile Ser
    450                 455                 460

Leu Ala Gln Leu Arg Leu Gln His Met Gln Gln Gln Val Met Ala Gln
465                 470                 475                 480

Arg Gln Gln Val Gln Arg Pro Ala Pro Val Gly Leu Pro Asn Pro
            485                 490                 495

Arg Met Gln Gly Pro Ile Gln Pro Ser Ile Ser His Gln Gln Pro
            500                 505                 510

Pro Pro Arg Leu Ile Asn Phe Gln Asn His Ser Pro Lys Pro Asn Gly
            515                 520                 525

Pro Val Leu Pro Pro His Pro Gln Gln Leu Arg Tyr Pro Pro Asn Gln
            530                 535                 540

Asn Ile Pro Arg Gln Ala Ile Lys Pro Asn Pro Leu Gln Met Ala Phe
545                 550                 555                 560

Leu Ala Gln Gln Ala Ile Lys Gln Trp Gln Ile Ser Ser Gly Gln Gly
                565                 570                 575

Thr Pro Ser Thr Thr Asn Ser Thr Ser Ser Thr Pro Ser Ser Pro Thr
            580                 585                 590

Ile Thr Ser Ala Ala Gly Tyr Asp Gly Lys Ala Phe Gly Ser Pro Met
            595                 600                 605

Ile Asp Leu Ser Ser Pro Val Gly Gly Ser Tyr Asn Leu Pro Ser Leu
            610                 615                 620

Pro Asp Ile Asp Cys Ser Ser Thr Ile Met Leu Asp Asn Ile Val Arg
625                 630                 635                 640

Lys Asp Thr Asn Ile Asp His Gly Gln Pro Arg Pro Pro Ser Asn Arg
                645                 650                 655

Thr Val Gln Ser Pro Asn Ser Ser Val Pro Ser Pro Gly Leu Ala Gly
            660                 665                 670

Pro Val Thr Met Thr Ser Val His Pro Pro Ile Arg Ser Pro Ser Ala
            675                 680                 685

Ser Ser Val Gly Ser Arg Gly Ser Ser Gly Ser Ser Lys Pro Ala
    690                 695                 700

Gly Ala Asp Ser Thr His Lys Val Pro Val Val Met Leu Glu Pro Ile
705                 710                 715                 720

Arg Ile Lys Gln Glu Asn Ser Gly Pro Pro Glu Asn Tyr Asp Phe Pro
                725                 730                 735

Val Val Ile Val Lys Gln Glu Ser Asp Glu Glu Ser Arg Pro Gln Asn
            740                 745                 750

Ala Asn Tyr Pro Arg Ser Ile Leu Thr Ser Leu Leu Leu Asn Ser Ser
            755                 760                 765

Gln Ser Ser Thr Ser Glu Glu Thr Val Leu Arg Ser Asp Ala Pro Asp
    770                 775                 780

Ser Thr Gly Asp Gln Pro Gly Leu His Gln Asp Asn Ser Ser Asn Gly
785                 790                 795                 800

Lys Ser Glu Trp Leu Asp Pro Ser Gln Lys Ser Pro Leu His Val Gly
                805                 810                 815

Glu Thr Arg Lys Glu Asp Asp Pro Asn Glu Asp Trp Cys Ala Val Cys
            820                 825                 830

Gln Asn Gly Gly Glu Leu Leu Cys Cys Glu Lys Cys Pro Lys Val Phe
    835                 840                 845

His Leu Ser Cys His Val Pro Thr Leu Thr Asn Phe Pro Ser Gly Glu
850                 855                 860
```

```
Trp Ile Cys Thr Phe Cys Arg Asp Leu Ser Lys Pro Glu Val Glu Tyr
865                 870                 875                 880

Asp Cys Asp Ala Pro Ser His Asn Ser Glu Lys Lys Thr Glu Gly
            885                 890                 895

Leu Val Lys Leu Thr Pro Ile Asp Lys Arg Lys Cys Glu Arg Leu Leu
            900                 905                 910

Leu Phe Leu Tyr Cys His Glu Met Ser Leu Ala Phe Gln Asp Pro Val
            915                 920                 925

Pro Leu Thr Val Pro Asp Tyr Tyr Lys Ile Ile Lys Asn Pro Met Asp
            930                 935                 940

Leu Ser Thr Ile Lys Lys Arg Leu Gln Glu Asp Tyr Ser Met Tyr Ser
945                 950                 955                 960

Lys Pro Glu Asp Phe Val Ala Asp Phe Arg Leu Ile Phe Gln Asn Cys
                965                 970                 975

Ala Glu Phe Asn Glu Pro Asp Ser Glu Val Ala Asn Ala Gly Ile Lys
            980                 985                 990

Leu Glu Asn Tyr Phe Glu Glu Leu Leu Lys Asn Leu Tyr Pro Glu Lys
            995                 1000                1005

Arg Phe  Pro Lys Pro Glu  Phe  Arg Asn Glu Ser Glu  Asp Asn Lys
1010                 1015                 1020

Phe Ser  Asp Asp Ser Asp  Asp  Phe Val Gln Pro  Arg Lys Lys
1025                 1030                 1035

Arg Leu  Lys Ser Ile Glu Glu  Arg Gln Leu Leu Lys
1040                 1045                 1050

<210> SEQ ID NO 3
<211> LENGTH: 21
<212> TYPE: RNA
<213> ORGANISM: artificial
<220> FEATURE:
<223> OTHER INFORMATION: siRNA sequence

<400> SEQUENCE: 3
aaacugaccu gucgagacuu u                                             21

<210> SEQ ID NO 4
<211> LENGTH: 21
<212> TYPE: DNA
<213> ORGANISM: artificial
<220> FEATURE:
<223> OTHER INFORMATION: siRNA sequence

<400> SEQUENCE: 4
gcaagcggcu gauuacauau u                                             21

<210> SEQ ID NO 5
<211> LENGTH: 21
<212> TYPE: DNA
<213> ORGANISM: artificial
<220> FEATURE:
<223> OTHER INFORMATION: siRNA sequence

<400> SEQUENCE: 5
uaaguucagu gacgacucau u                                             21

<210> SEQ ID NO 6
<211> LENGTH: 21
<212> TYPE: DNA
<213> ORGANISM: artificial
<220> FEATURE:
<223> OTHER INFORMATION: siRNA sequence
```

```
<400> SEQUENCE: 6
uagagcacgu caugcauuuu u                                            21

<210> SEQ ID NO 7
<211> LENGTH: 22
<212> TYPE: DNA
<213> ORGANISM: artificial
<220> FEATURE:
<223> OTHER INFORMATION: siRNA sequence

<400> SEQUENCE: 7
cgcatgaaac ttatgcaaca ac                                           22

<210> SEQ ID NO 8
<211> LENGTH: 22
<212> TYPE: DNA
<213> ORGANISM: artificial
<220> FEATURE:
<223> OTHER INFORMATION: siRNA sequence

<400> SEQUENCE: 8
gccatgaaat gagcctggct tt                                           22

<210> SEQ ID NO 9
<211> LENGTH: 21
<212> TYPE: DNA
<213> ORGANISM: artificial
<220> FEATURE:
<223> OTHER INFORMATION: siRNA sequence

<400> SEQUENCE: 9
cctgttgtta tagtgaagca a                                            21

<210> SEQ ID NO 10
<211> LENGTH: 22
<212> TYPE: DNA
<213> ORGANISM: artificial
<220> FEATURE:
<223> OTHER INFORMATION: siRNA sequence

<400> SEQUENCE: 10
ggcagcagta cagcattact tt                                           22

<210> SEQ ID NO 11
<211> LENGTH: 21
<212> TYPE: DNA
<213> ORGANISM: Artificial
<220> FEATURE:
<223> OTHER INFORMATION: siRNA sequence

<400> SEQUENCE: 11
cgagacttat ctaaaccaga a                                            21

<210> SEQ ID NO 12
<211> LENGTH: 22
<212> TYPE: DNA
<213> ORGANISM: artificial
<220> FEATURE:
<223> OTHER INFORMATION: siRNA sequence

<400> SEQUENCE: 12
gttgttgcat aagtttcatg cg                                           22

<210> SEQ ID NO 13
<211> LENGTH: 22
```

<212> TYPE: DNA
<213> ORGANISM: artificial
<220> FEATURE:
<223> OTHER INFORMATION: siRNA sequence

<400> SEQUENCE: 13
aaagccaggc tcatttcatg gc                                           22

<210> SEQ ID NO 14
<211> LENGTH: 21
<212> TYPE: DNA
<213> ORGANISM: artificial
<220> FEATURE:
<223> OTHER INFORMATION: siRNA sequence

<400> SEQUENCE: 14
ttgcttcact ataacaacag g                                            21

<210> SEQ ID NO 15
<211> LENGTH: 22
<212> TYPE: DNA
<213> ORGANISM: artificial
<220> FEATURE:
<223> OTHER INFORMATION: siRNA sequence

<400> SEQUENCE: 15
aaagtaatgc tgtactgctg cc                                           22

<210> SEQ ID NO 16
<211> LENGTH: 20
<212> TYPE: DNA
<213> ORGANISM: artificial
<220> FEATURE:
<223> OTHER INFORMATION: siRNA sequence

<400> SEQUENCE: 16
ttctggttta gataagtctc                                              20

<210> SEQ ID NO 17
<211> LENGTH: 57
<212> TYPE: DNA
<213> ORGANISM: artificial
<220> FEATURE:
<223> OTHER INFORMATION: shRNA sequence

<400> SEQUENCE: 17
ccggcgcatg aaacttatgc aacaactcga gttgttgcat aagtttcatg cgttttt     57

<210> SEQ ID NO 18
<211> LENGTH: 57
<212> TYPE: DNA
<213> ORGANISM: artificial
<220> FEATURE:
<223> OTHER INFORMATION: shRNA sequence

<400> SEQUENCE: 18
ccggccatga atgagcctg gctttctcga gaaagccagg ctcatttcat ggttttt      57

<210> SEQ ID NO 19
<211> LENGTH: 57
<212> TYPE: DNA
<213> ORGANISM: artificial
<220> FEATURE:
<223> OTHER INFORMATION: shRNA sequence

<400> SEQUENCE: 19
ccggcctgtt gttatagtga agcaactcga gttgcttcac tataacaaca ggttttt     57

```
<210> SEQ ID NO 20
<211> LENGTH: 57
<212> TYPE: DNA
<213> ORGANISM: artificial
<220> FEATURE:
<223> OTHER INFORMATION: shRNA sequence

<400> SEQUENCE: 20
ccgggcagca gtacagcatt actttctcga gaaagtaatg ctgtactgct gcttttt         57

<210> SEQ ID NO 21
<211> LENGTH: 57
<212> TYPE: DNA
<213> ORGANISM: artificial
<220> FEATURE:
<223> OTHER INFORMATION: shRNA sequence

<400> SEQUENCE: 21
ccggcgagac ttatctaaac cagaactcga gttctggttt agataagtct cgttttt         57

<210> SEQ ID NO 22
<211> LENGTH: 21
<212> TYPE: DNA
<213> ORGANISM: artificial
<220> FEATURE:
<223> OTHER INFORMATION: siRNA sequence

<400> SEQUENCE: 22
agucucgaca ggucaguuuu u                                                21

<210> SEQ ID NO 23
<211> LENGTH: 21
<212> TYPE: DNA
<213> ORGANISM: artificial
<220> FEATURE:
<223> OTHER INFORMATION: siRNA sequence

<400> SEQUENCE: 23
uauguaauca gccgcuugcu u                                                21

<210> SEQ ID NO 24
<211> LENGTH: 21
<212> TYPE: DNA
<213> ORGANISM: artificial
<220> FEATURE:
<223> OTHER INFORMATION: siRNA sequence

<400> SEQUENCE: 24
ugagucguca cugaacuuau u                                                21

<210> SEQ ID NO 25
<211> LENGTH: 21
<212> TYPE: DNA
<213> ORGANISM: artificial
<220> FEATURE:
<223> OTHER INFORMATION: siRNA sequence

<400> SEQUENCE: 25
aaaugcauga cgugcucuau u                                                21

<210> SEQ ID NO 26
<211> LENGTH: 10
<212> TYPE: DNA
<213> ORGANISM: homo sapiens
<220> FEATURE:
<221> NAME/KEY: misc_feature
```

```
<222> LOCATION: (1)..(10)
<223> OTHER INFORMATION: p53 response element

<400> SEQUENCE: 26 rrrcwwgyyy                                                                10

<210> SEQ ID NO 27
<211> LENGTH: 21
<212> TYPE: DNA
<213> ORGANISM: artificial
<220> FEATURE:
<223> OTHER INFORMATION: siRNA sequence

<400> SEQUENCE: 27
ggaaaucaga uccaaaacat t                                                   21

<210> SEQ ID NO 28
<211> LENGTH: 21
<212> TYPE: DNA
<213> ORGANISM: artificial
<220> FEATURE:
<223> OTHER INFORMATION: siRNA sequence

<400> SEQUENCE: 28
cccaaguugg agucauucgt t                                                   21

<210> SEQ ID NO 29
<211> LENGTH: 21
<212> TYPE: DNA
<213> ORGANISM: artificial
<220> FEATURE:
<223> OTHER INFORMATION: siRNA sequence

<400> SEQUENCE: 29
gguauguaca agcugugagt t                                                   21

<210> SEQ ID NO 30
<211> LENGTH: 21
<212> TYPE: DNA
<213> ORGANISM: artificial
<220> FEATURE:
<223> OTHER INFORMATION: siRNA sequence

<400> SEQUENCE: 30
ggacaacgca gaagccaaut t                                                   21

<210> SEQ ID NO 31
<211> LENGTH: 21
<212> TYPE: DNA
<213> ORGANISM: artificial
<220> FEATURE:
<223> OTHER INFORMATION: siRNA sequence

<400> SEQUENCE: 31
ggccuuguua aguuaacact t                                                   21

<210> SEQ ID NO 32
<211> LENGTH: 21
<212> TYPE: DNA
<213> ORGANISM: artificial
<220> FEATURE:
<223> OTHER INFORMATION: siRNA sequence

<400> SEQUENCE: 32
ggaggaacag gauauuaaat t                                                   21
```

```
<210> SEQ ID NO 33
<211> LENGTH: 21
<212> TYPE: DNA
<213> ORGANISM: artificial
<220> FEATURE:
<223> OTHER INFORMATION: siRNA sequence

<400> SEQUENCE: 33
gaacggucca gucaccaaat t                                              21

<210> SEQ ID NO 34
<211> LENGTH: 21
<212> TYPE: DNA
<213> ORGANISM: artificial
<220> FEATURE:
<223> OTHER INFORMATION: siRNA sequence

<400> SEQUENCE: 34
gucaguuguu agaacauaat t                                              21

<210> SEQ ID NO 35
<211> LENGTH: 21
<212> TYPE: DNA
<213> ORGANISM: artificial
<220> FEATURE:
<223> OTHER INFORMATION: siRNA

<400> SEQUENCE: 35
cgacugauua cauaccggut t                                              21

<210> SEQ ID NO 36
<211> LENGTH: 21
<212> TYPE: DNA
<213> ORGANISM: artificial
<220> FEATURE:
<223> OTHER INFORMATION: siRNA sequence

<400> SEQUENCE: 36
uguuuuggau cugauuucct g                                              21

<210> SEQ ID NO 37
<211> LENGTH: 21
<212> TYPE: DNA
<213> ORGANISM: artificial
<220> FEATURE:
<223> OTHER INFORMATION: siRNA sequence

<400> SEQUENCE: 37
cgaaugacuc caacuugggt g                                              21

<210> SEQ ID NO 38
<211> LENGTH: 21
<212> TYPE: DNA
<213> ORGANISM: artificial
<220> FEATURE:
<223> OTHER INFORMATION: siRNA sequence

<400> SEQUENCE: 38
cucacagcuu guacauacct g                                              21

<210> SEQ ID NO 39
<211> LENGTH: 21
<212> TYPE: DNA
<213> ORGANISM: artificial
<220> FEATURE:
<223> OTHER INFORMATION: siRNA sequence

<400> SEQUENCE: 39
```
auuggcuucu gcguugucct c                                              21

<210> SEQ ID NO 40
<211> LENGTH: 21
<212> TYPE: DNA
<213> ORGANISM: artificial
<220> FEATURE:
<223> OTHER INFORMATION: siRNA sequence

<400> SEQUENCE: 40
guguuaacuu aacaaggcct t                                              21

<210> SEQ ID NO 41
<211> LENGTH: 21
<212> TYPE: DNA
<213> ORGANISM: artificial
<220> FEATURE:
<223> OTHER INFORMATION: siRNA sequence

<400> SEQUENCE: 41
uuuaauaucc uguuccacct g                                              21

<210> SEQ ID NO 42
<211> LENGTH: 21
<212> TYPE: DNA
<213> ORGANISM: artificial
<220> FEATURE:
<223> OTHER INFORMATION: siRNA sequence

<400> SEQUENCE: 42
uuuggugacu ggaccguuct g                                              21

<210> SEQ ID NO 43
<211> LENGTH: 21
<212> TYPE: DNA
<213> ORGANISM: artificial
<220> FEATURE:
<223> OTHER INFORMATION: siRNA sequence

<400> SEQUENCE: 43
uuauguucua acaacugaca g                                              21

<210> SEQ ID NO 44
<211> LENGTH: 21
<212> TYPE: DNA
<213> ORGANISM: artificial
<220> FEATURE:
<223> OTHER INFORMATION: siRNA sequence

<400> SEQUENCE: 44
accgguaugu aaucagucgt t                                              21

<210> SEQ ID NO 45
<211> LENGTH: 21
<212> TYPE: DNA
<213> ORGANISM: artificial
<220> FEATURE:
<223> OTHER INFORMATION: PCR primer

<400> SEQUENCE: 45
gcaagcggct gattacatac a                                              21

<210> SEQ ID NO 46
<211> LENGTH: 21
<212> TYPE: DNA
<213> ORGANISM: artificial

```
<220> FEATURE:
<223> OTHER INFORMATION: PCR primer

<400> SEQUENCE: 46
tggtcacagg agaagcatca c                                              21

<210> SEQ ID NO 47
<211> LENGTH: 20
<212> TYPE: DNA
<213> ORGANISM: artificial
<220> FEATURE:
<223> OTHER INFORMATION: PCR primer

<400> SEQUENCE: 47
acatgacgga ggtcgtgaga                                                20

<210> SEQ ID NO 48
<211> LENGTH: 20
<212> TYPE: DNA
<213> ORGANISM: Artificial
<220> FEATURE:
<223> OTHER INFORMATION: PCR primer

<400> SEQUENCE: 48
tttccttcca cccggataag                                                20

<210> SEQ ID NO 49
<211> LENGTH: 17
<212> TYPE: DNA
<213> ORGANISM: artificial
<220> FEATURE:
<223> OTHER INFORMATION: PCR primer

<400> SEQUENCE: 49
tctcagggcc gaaaacg                                                   17

<210> SEQ ID NO 50
<211> LENGTH: 22
<212> TYPE: DNA
<213> ORGANISM: artificial
<220> FEATURE:
<223> OTHER INFORMATION: PCR primer

<400> SEQUENCE: 50
cgcttggagt gatagaaatc tg                                             22

<210> SEQ ID NO 51
<211> LENGTH: 23
<212> TYPE: DNA
<213> ORGANISM: artificial
<220> FEATURE:
<223> OTHER INFORMATION: PCR primer

<400> SEQUENCE: 51
attgcctgga tcaggattca gtt                                            23

<210> SEQ ID NO 52
<211> LENGTH: 22
<212> TYPE: DNA
<213> ORGANISM: artificial
<220> FEATURE:
<223> OTHER INFORMATION: PCR primer

<400> SEQUENCE: 52
acctcatcat cctcatctga ga                                             22
```

```
<210> SEQ ID NO 53
<211> LENGTH: 20
<212> TYPE: DNA
<213> ORGANISM: artificial
<220> FEATURE:
<223> OTHER INFORMATION: PCR primer

<400> SEQUENCE: 53
tcatcctgtg catctgcttc                                                     20

<210> SEQ ID NO 54
<211> LENGTH: 20
<212> TYPE: DNA
<213> ORGANISM: artificial
<220> FEATURE:
<223> OTHER INFORMATION: PCR primer

<400> SEQUENCE: 54
gggttatcgt gaagcctgaa                                                     20

<210> SEQ ID NO 55
<211> LENGTH: 20
<212> TYPE: DNA
<213> ORGANISM: artificial
<220> FEATURE:
<223> OTHER INFORMATION: PCR primer

<400> SEQUENCE: 55
tccagcagat gcaagaactc                                                     20

<210> SEQ ID NO 56
<211> LENGTH: 20
<212> TYPE: DNA
<213> ORGANISM: artificial
<220> FEATURE:
<223> OTHER INFORMATION: PCR primer

<400> SEQUENCE: 56
gtgctgagcc cttctgaatc                                                     20

<210> SEQ ID NO 57
<211> LENGTH: 22
<212> TYPE: DNA
<213> ORGANISM: artificial
<220> FEATURE:
<223> OTHER INFORMATION: PCR primer

<400> SEQUENCE: 57
tcaagaacga aagtcggagg tt                                                  22

<210> SEQ ID NO 58
<211> LENGTH: 21
<212> TYPE: DNA
<213> ORGANISM: artificial
<220> FEATURE:
<223> OTHER INFORMATION: PCR primer

<400> SEQUENCE: 58
ggacatctaa gggcatcaca g                                                   21

<210> SEQ ID NO 59
<211> LENGTH: 4007
<212> TYPE: DNA
<213> ORGANISM: homo sapiens

<400> SEQUENCE: 59
gacagatacc ctccttccgg ccgcgccact cgggaggcgg atcccgtggg cctgaggagg         60
```

```
cttccccgc ccggtttgct ttccctccct cgctggcgct gccgcgagtc caccgagcgg    120
cctctgagga gcagccgcag gaggaggagg aggtcgtcgg gggcggcggg cggagaccgc    180
gctctcgctt ccccggcggc ggcaagggca ggacaatgga ggtggcggtg gagaaggcgg    240
tggcggcggc ggcagcggcc tcggctgcgg cctccggggg gccctcggcg gcgccgagcg    300
gggagaacga ggccgagagt cggcagggcc cggactcgga gcgcggcggc gaggcggccc    360
ggctcaacct gttggacact gccgccgtgt gccaccagaa catccagagc cgggcgccca    420
agctgctgcc ctgcctgcac tctttctgcc agcgctgcct gcccgcgccc cagcgctacc    480
tcatgctgcc cgcgcccatg ctgggctcgg ccagaccccc gccacccgtc cctgccccg    540 gctcgccggt cagcggctcg tcgccgttcg ccacccaagt tggagtcatt cgttgcccag    600
tttgcagcca agaatgtgca gagagacaca tcatagataa cttttttgtg aaggacacta    660
ctgaggttcc cagcagtaca gtagaaaagt caaatcaggt atgtacaagc tgtgaggaca    720
acgcagaagc caatgggttt tgtgtagagt gtgttgaatg gctctgcaag acgtgtatca    780
gagctcatca gagggtaaag ttcacaaaag accacactgt cagacagaaa gaggaagtat    840
ctccagaggc agttggtgtc accagccagc gaccagtgtt ttgtcctttt cataaaaagg    900
agcagctgaa gctgtactgt gagacatgtg acaaactgac atgtcgagac tgtcagttgt    960
tagaacataa agagcataga taccaattta tagaagaagc ttttcagaat cagaaagtga    1020
tcatagatac actaatcacc aaactgatgg aaaaacaaa atacataaaa ttcacaggaa    1080
atcagatcca aaacagaatt attgaagtaa atcaaaatca aaagcaggtg gaacaggata    1140
ttaaagttgc tatatttaca ctgatggtag aaataaataa aaaaggaaaa gctctactgc    1200
atcagttaga gagccttgca aaggaccatc gcatgaaact tatgcaacaa caacaggaag    1260
tggctggact ctctaaacaa ttggagcatg tcatgcattt ttctaaatgg gcagtttcca    1320
gtggcagcag tacagcatta cttttatagca aacgactgat tacataccgg ttacggcacc    1380
tccttcgtgc aaggtgtgat gcatccccag tgaccaacaa caccatccaa tttcactgtg    1440
atcctagttt ctgggctcaa aatatcatca acttaggttc tttagtaatc gaggataaag    1500
agagccagcc acaaatgcct aagcagaatc ctgtcgtgga acagaattca cagccaccaa    1560
gtggtttatc atcaaaccag ttatccaagt tcccaacaca gatcagccta gctcaattac    1620
ggctccagca tatgcagcaa caggtaatgg ctcagaggca acaggtgcaa cggaggccag    1680
cacctgtggg tttaccaaac cctagaatgc aggggcccat ccagcaacct tccatctctc    1740
atcagcaacc gcctccacgt tgataaact ttcagaatca cagccccaaa cccaatggac    1800
cagttcttcc tcctcatcct caacaactga gatatccacc aaaccagaac ataccacgac    1860
aagcaataaa gccaaacccc ctacagatgg ctttcttggc tcaacaagcc ataaaacagt    1920
ggcagatcag cagtggacag ggaaccccat caactaccaa cagcacatcc tctactcctt    1980
ccagccccac gattactagt gcagcaggat atgatggaaa ggcttttggt tcacctatga    2040
tcgatttgag ctcaccagtg ggagggtctt ataatcttcc ctctcttccg gatattgact    2100
gttcaagtac tattatgctg gacaaatattg tgaggaaaga tactaatata gatcatggcc    2160
agccaagacc accctcaaac agaacggtcc agtcaccaaa ttcatcagtg ccatctccag    2220
gccttgcagg acctgttact atgactagtg tacacccccc aatacgttca cctagtgcct    2280
ccagcgttgg aagccgagga agctctggcc cttccagcaa accagcagga gctgactcta    2340
cacacaaagt cccagtggtc atgctggagc caattcgaat aaaacaagaa acagtggac    2400 caccggaaaa ttatgatttc cctgttgtta tagtgaagca agaatcagat gaagaatcta    2460
```

```
ggcctcaaaa tgccaattat ccaagaagca tactcacctc cctgctctta aatagcagtc    2520
agagctctac ttctgaggag actgtgctaa gatcagatgc ccctgatagt acaggagatc    2580
aacctggact tcaccaggac aattcctcaa atggaaagtc tgaatggttg gatccttccc    2640
agaagtcacc tcttcatgtt ggagagacaa ggaaagagga tgaccccaat gaggactggt    2700
gtgcagtttg tcaaaacgga ggggaactcc tctgctgtga aaagtgcccc aaagtattcc    2760
atctttcttg tcatgtgccc acattgacaa attttccaag tggagagtgg atttgcactt    2820
tctgccgaga cttatctaaa ccagaagtta aatatgattg tgatgctccc agtcacaact    2880
cagaaaaaaa gaaaactgaa ggccttgtta agttaacacc tatagataaa aggaagtgtg    2940
agcgcctact tttatttctt tactgccatg aaatgagcct ggcttttcaa gaccctgttc    3000
ctctaactgt gcctgattat tacaaaataa ttaaaaatcc aatggatttg tcaaccatca    3060
agaaaagact acaagaagat tattccatgt actcaaaacc tgaagatttt gtagctgatt    3120
ttagattgat ctttcaaaac tgtgctgaat tcaatgagcc tgattcagaa gtagccaatg    3180
ctggtataaa acttgaaaat tattttgaag aacttctaaa gaacctctat ccagaaaaaa    3240
ggtttcccaa accagaattc aggaatgaat cagaagataa taaatttagt gatgattcag    3300
atgatgactt tgtacagccc cggaagaaac gcctcaaaag cattgaagaa cgccagttgc    3360
ttaaataata tgcagcacca ctagcttgtg ctggttttta gattttttg ttttcaaaaa    3420 aacatttgtc agtaatttaa catcactaca aaagaagag tttgtgacta ttctcatctc    3480
tgttttggac gttactaga ctttgatttc cttaatagcc catttctgtt aacctcttat    3540
cactaagaaa gaaaggaaag aaggagatga atagaagaaa gaaatggaa agaaggaaaa    3600 aaggaggata gaaaaggat ggaagaaga agcattgaaa acaaagacat tcttcccact    3660
tcttggattt ttaaaccaca gtctggagtg atagctactg tagaaaggaa atagactttg    3720
tatgaactct ttaagttgaa aagtaaaaaa tatatgtggt ttggatgtgt gctttaattc    3780
agctttagaa attaatacca ctacccgtga attatatggc ctgacaatat gaattaggtg    3840
tactgtactg aagaacagta ctccacaaac atgggtggta acaagagttc catcccagga    3900
ggccaaacgg tgcaacagaa gggtaggtta gatgctatta agaaggcact taatagtaca    3960
tcatgtaaga tggcaactgt attaaagaaa aatccggaaa acaaaaa              4007

<210> SEQ ID NO 60
<211> LENGTH: 3905
<212> TYPE: DNA
<213> ORGANISM: homo sapiens

<400> SEQUENCE: 60
gacagatacc ctccttccgg ccgcgccact cgggaggcgg atcccgtggg cctgaggagg      60
cttcccccgc ccggttgct ttccctccct cgctggcgct gccgcgagtc caccgagcgg     120
cctctgagga gcagccgcag gaggaggagg aggtcgtcgg gggcggcggg cggagaccgc     180
gctctcgctt ccccggcggc ggcaagggca ggacaatgga ggtggcggtg gagaaggcgg     240
tggcggcggc ggcagcggcc tcggctgcgg cctccggggg gccctcggcg cgccgagcg     300 gggagaacga ggccgagagt cggcagggcc cggactcgga gcgcggcggc gaggcggccc     360
ggctcaacct gttggacact gcgccgtgt gccaccagaa catccagagc cgggcgccca     420
agctgctgcc ctgcctgcac tctttctgcc agcgctgcct gccgcgcccc cagcgctacc     480
tcatgctgcc cgcgcccatg ctgggctcgg ccgagacccc gccacccgtc cctgcccccg     540
gctcgccggt cagcggctcg tcgccgttcg ccacccaagt tggagtcatt cgttgcccag     600
```

```
tttgcagcca agaatgtgca gagagacaca tcatagataa cttttttgtg aaggacacta    660
ctgaggttcc cagcagtaca gtagaaaagt caaatcaggt atgtacaagc tgtgaggaca    720
acgcagaagc caatgggttt tgtgtagagt gtgttgaatg gctctgcaag acgtgtatca    780
gagctcatca gagggtaaag ttcacaaaag accacactgt cagacagaaa gaggaagtat    840
ctccagaggc agttggtgtc accagccagc gaccagtgtt ttgtccttttt cataaaaagg    900
agcagctgaa gctgtactgt gagacatgtg acaaactgac atgtcgagac tgtcagttgt    960
tagaacataa agagcataga taccaattta tagaagaagc ttttcagaat cagaaagtga   1020
tcatagatac actaatcacc aaactgatgg aaaaaacaaa atacataaaa ttcacaggaa   1080
atcagatcca aaacagaatt attgaagtaa atcaaaatca aaagcaggtg aacaggata    1140
ttaaagttgc tatatttaca ctgatggtag aaataaataa aaaaggaaaa gctctactgc   1200
atcagttaga gagccttgca aaggaccatc gcatgaaact tatgcaacaa caacaggaag   1260
tggctggact ctctaaacaa ttggagcatg tcatgcattt ttctaaatgg gcagtttcca   1320
gtggcagcag tacagcatta ctttatagca acgactgat tacataccgg ttacggcacc   1380
tccttcgtgc aaggtgtgat gcatccccag tgaccaacaa caccatccaa tttcactgtg   1440
atcctagttt ctgggctcaa aatatcatca acttaggttc tttagtaatc gaggataaag   1500
agagccagcc acaaatgcct aagcagaatc ctgtcgtgga acagaattca cagccaccaa   1560
gtggtttatc atcaaaccag ttatccaagt tcccaacaca gatcagccta gctcaattac   1620
ggctccagca tatgcagcaa cagcaaccgc ctccacgttt gataaacttt cagaatcaca   1680
gccccaaacc caatggacca gttcttcctc ctcatcctca acaactgaga tatccaccaa   1740
accagaacat accacgacaa gcaataaagc caaaccccct acagatggct ttcttggctc   1800
aacaagccat aaaacagtgg cagatcagca gtggacaggg aaccccatca actaccaaca   1860
gcacatcctc tactccttcc agccccacga ttactagtgc agcaggatat gatggaaagg   1920
cttttggttc acctatgatc gatttgagct caccagtggg agggtcttat aatcttccct   1980
ctcttccgga tattgactgt tcaagtacta ttatgctgga caatattgtg aggaaagata   2040
ctaatataga tcatggccag ccaagaccac cctcaaacag aacggtccag tcaccaaatt   2100
catcagtgcc atctccaggc cttgcaggac ctgttactat gactagtgta cacccccaa    2160
tacgttcacc tagtgcctcc agcgttggaa gccgaggaag ctctggctct tccagcaaac   2220
cagcaggagc tgactctaca cacaaagtcc cagtggtcat gctggagcca attcgaataa   2280
aacaagaaaa cagtggacca ccggaaaatt atgatttccc tgttgttata gtgaagcaag   2340
aatcagatga agaatctagg cctcaaaatg ccaattatcc aagaagcata ctcacctccc   2400
tgctcttaaa tagcagtcag agctctactt ctgaggagac tgtgctaaga tcagatgccc   2460
ctgatagtac aggagatcaa cctggacttc accaggacaa ttcctcaaat ggaaagtctg   2520
aatggttgga tccttcccag aagtcacctc ttcatgttgg agagacaagg aaagaggatg   2580
accccaatga ggactggtgt gcagtttgtc aaaacggagg ggaactcctc tgctgtgaaa   2640
agtgcccaa agtattccat cttcttgtc atgtgcccac attgacaaat tttccaagtg    2700
gagagtggat ttgcactttc tgccgagact tatctaaacc agaagttgaa tatgattgtg   2760
atgctcccag tcacaactca gaaaaaaga aaactgaagg ccttgttaag ttaacaccta   2820
tagataaaag gaagtgtgag cgcctacttt tatttcttta ctgccatgaa atgagcctgg   2880
cttttcaaga ccctgttcct ctaactgtgc ctgattatta caaataatt aaaaatccaa    2940
tggatttgtc aaccatcaag aaaagactac aagaagatta ttccatgtac tcaaaacctg   3000
```

```
aagattttgt agctgatttt agattgatct ttcaaaactg tgctgaattc aatgagcctg    3060
attcagaagt agccaatgct ggtataaaac ttgaaaatta ttttgaagaa cttctaaaga    3120
acctctatcc agaaaaaagg tttcccaaac cagaattcag gaatgaatca gaagataata    3180
aatttagtga tgattcagat gatgactttg tacagccccg gaagaaacgc ctcaaaagca    3240
ttgaagaacg ccagttgctt aaataatatg cagcaccact agcttgtgct ggttttttaga   3300 tttttttgtt ttcaaaaaaa catttgtcag taatttaaca tcactacaaa aagaagagtt    3360
tgtgactatt ctcatctctg ttttggacgt ttactagact ttgatttcct taatagccca    3420
tttctgttaa cctcttatca ctaagaaaga aggaaagaa ggagatgaat agaagaaga     3480 aaatggaaag aaggaaaaaa ggaggataga aaaggatgg aagaaagaag cattgaaaac    3540
aaagacattc ttcccacttc ttggattttt aaaccacagt ctggagtgat agctactgta    3600
gaaaggaaat agactttgta tgaactcttt aagttgaaaa gtaaaaaata tatgtggttt    3660
ggatgtgtgc tttaattcag ctttagaaat taataccact acccgtgaat tatatggcct    3720
gacaatatga attaggtgta ctgtactgaa aacagtact ccacaaacat gggtggtaac     3780
aagagttcca tcccaggagg ccaaacggtg caacagaagg gtaggttaga tgctattaag    3840
aaggcactta atagtacatc atgtaagatg gcaactgtat taaagaaaaa tccggaaaac    3900
aaaaa                                                              3905

<210> SEQ ID NO 61
<211> LENGTH: 3039
<212> TYPE: DNA
<213> ORGANISM: homo sapiens

<400> SEQUENCE: 61
atggaggtgg cggtggagaa ggcggtggcg gcggcggcac ggctcggctg cgctccgggg     60
ggccctcggg gcggcgggga gaacgaggcc gagagtcggc agggcccgga ctcggagcgc    120
ggcggcgagg cggcccggct caacctgttg gacacttgcg ccgtgtgcca ccagaacatc    180
cagagccggg cgcccaagct gctgccctgc ctgcactctt tctgccagcg ctgcctgccc    240
gcgccccagc gctacctcat gctgcccgcg cccatgctgg gctcggccga gccccgccca    300
cccgtccctg cccggctccg ccggtcagcc tcgtcgccgt tcgccaccca agttggagtc    360
attcgttgcc cagtttgcag ccaagaatgt gcagagagac acatcataga taacttttttt  420 gtgaaggaca ctactgaggt tcccagcagt acagtagaaa agtcaaatca ggtatgtaca    480
agctgtgagg acaacgcaga agccaatggg ttttgtgtag agtgtgttga atggctctgc    540
aagacgtgta tcagagctca tcagagggta aagttcacaa aagaccacac tgtcagacag    600
aaagaggaag tatctccaga ggcagttggt gtcaccagcc agcgaccagt gttttgtcct    660
tttcataaaa aggagcagct gaagctgtac tgtgagacat gtgacaaact gacatgtcga    720
gactgtcagt tgttagaaca taagagcat agataccaat ttatagaaga agcttttcag     780
aatcagaaag tgatcataga tacactaatc accaaactga tggaaaaaac aaaatacata    840
aaattcacag gaaatcagat ccaaaacaga attattgaag taaatcaaaa tcaaaagcag    900
gtggaacagg atattaaagt tgctatattt acactgatgg tagaaataaa taaaaaagga    960
aaagctctac tgcatcagtt agagagcctt gcaaaggacc atcgcatgaa acttatgcaa   1020
caacaacagg aagtgactgg actctctaaa caattggagc atgtcatgca ttttctaaa    1080 tgggcagttt ccagtggcag cagtacagca ttacttttata gcaaacgact gattacatac   1140
cggttacggc acctccttcg tgcaaggtgt gatgcatccc cagtgaccaa caacaccatc   1200
```

```
caatttcact gtgatcctag tttctgggct caaaatatca tcaacttagg ttctttagta    1260
atcgaggata aagagagcca gccacaaatg cctaagcaga atcctgtcgt ggaacagaat    1320
tcacagccac caagtggttt atcatcaaac cagttatcca agttcccaac acagatcagc    1380
ctagctcaat tacggctcca gcatatgcag caacagcaac cgcctccacg tttgataaac    1440
tttcagaatc acagcccaa acccaatgga ccagttcttc ctcctcatcc tcaacaactg     1500
agatatccac caaaccagaa cataccacga caagcaataa agccaaaccc cctacagatg    1560
gctttcttgg ctcaacaagc cataaaacag tggcagatca gcagtggaca gggaacccca    1620
tcaactacca acagcacatc ctctactcct tccagcccca cgattactag tgcagcagga    1680
tataatggaa aggcttttgg ttcacctata atcgatttga gctcaccagt gggagggtct    1740
tataatcttc cctctcttcc ggatattgac tgttcaagta ctattatgct ggacaatatt    1800
gtgaggaaag atactaatat agatcatggc cagccaagac caccctcaaa cagaacggtc    1860
cagtcaccaa attcatcagt gccatctcca ggccttgcag gacctgttac tatgactagt    1920
gtacaccccc caatacgttc acctagtgcc tccagcgttg gaagccgagg aagctctggc    1980
tcttccagca accagcagg agctgactct acacacaaag tcccagtggt catgctggag     2040
ccaattcgaa taaaacaaga aaacagtgga ccaccggaaa attatgattt cccagttgtt    2100
atagtgaagc aagaatcaga tgaagaatct aggcctcaaa atgccaatta ccaagaagc     2160 atactcacct ccctgctctt aaatagcagt cagagctcta cttctgagga gactgtgcta    2220
agatcagatg cccctgatag tacaggagat caacctggac ttcaccagga caattcctca    2280
aatggaaagt ctgaatggtt ggatccttcc cagaagtcac ctcttcatgt tggagagaca    2340
aggaaagagg atgaccccaa tgaggactgg tgtgcagttt gtcaaaacgg aggggaactc    2400
ctctgctgtg aaaagtgccc caaagtattc catctttctt gtcatgtgcc cacattgaca    2460
aattttccaa gtggagagtg gatttgcact ttctgccgag acttatctaa accagaagtt    2520
gaatatgatt gtgatgctcc cagtcacaac tcagaaaaaa agaaaactga aggccttgtt    2580
aagttaacac ctatagataa aaggaagtgt gagcgcctac tttatttct ttactgccat      2640 gaaatgagcc tggcttttca agaccctgtt cctctaactg tgcctgatta ttacaaaata    2700
attaaaaatc caatggattt gtcaaccatc aagaaaagac tacaagaaga ttattccatg    2760
tactcaaaac ctgaagattt tgtacgtgat tttagattga tctttcaaaa ctgtgctgaa    2820
ttcaatgagc ctgattcaga agtagccaat gctggtataa aacttgaaaa ttattttgaa    2880
gaacttctaa agaacctcta tccagaaaaa aggtttccca aaccagaatt caggaatgaa    2940
tcagaagata ataaatttag tgatgattca gatgatgact ttgtacagcc ccggaagaaa    3000
cgcctcaaaa gcattgaaga acgccagttg cttaaataa                           3039
```

<210> SEQ ID NO 62
<211> LENGTH: 3909
<212> TYPE: DNA
<213> ORGANISM: homo sapiens

<400> SEQUENCE: 62

```
agcgggtcca ccgagcggcc tctgaggagc agccgcagga ggaggaggag gtcgtcgggg      60
gcggcgggcg gagaccgcgc tctcgcttcc ccggcggcgg caaggcagg acaatggagg      120 tgcggtgga gaaggcggtg gcggcggcgg cagcggcctc ggctgcggcc tccgggggc       180 cctcggcggc gccgagcggg gagaacgagg ccgagtcg gcagggcccg gactcggagc       240
gcggcggcga ggcggcccgg ctcaacctgt tggacacttg cgccgtgtgc caccagaaca     300
```

```
tccagagccg ggcgcccaag ctgctgccct gcctgcactc tttctgccag cgctgcctgc    360
ccgcgcccca gcgctacctc atgctgcccg cgcccatgct gggctcggcc gagacccccgc   420 cacccgtccc tgcccccggc tcgccggtca gcggctcgtc gccgttcgcc acccaagttg    480
gagtcattcg ttgcccagtt tgcagccaag aatgtgcaga gagacacatc atagataact    540
tttttgtgaa ggacactact gaggttccca gcagtacagt agaaaagtca atcaggtat     600 gtacaagctg tgaggacaac gcagaagcca atgggttttg tgtagagtgt gttgaatggc    660
tctgcaagac gtgtatcaga gctcatcaga gggtaaagtt cacaaaagac cacactgtca    720
gacagaaaga ggaagtatct ccagaggcag ttggtgtcac cagccagcga ccagtgtttt    780
gtccttttca taaaaaggag cagctgaagc tgtactgtga cactgtgac aaactgacat     840 gtcgagactg tcagttgtta aacataaag agcatagata ccaatttata gaagaagctt     900
ttcagaatca gaaagtgatc atagatacac taatcaccaa actgatggaa aaacaaaat    960 acataaaatt cacaggaaat cagatccaaa acagaattat tgaagtaaat caaaatcaaa   1020
agcaggtgga acaggatatt aaagttgcta tatttacact gatggtagaa ataaataaaa   1080
aaggaaaagc tctactgcat cagttagaga gccttgcaaa ggaccatcgc atgaaactta   1140
tgcaacaaca acaggaagtg gctggactct ctaaacaatt ggagcatgtc atgcattttt   1200
ctaaatgggc agtttccagt ggcagcagta cagcattact ttatagcaaa cgactgatta   1260
cataccggtt acgacacctc cttcgtgcaa ggtgtgatgc atccccagtg accaacaaca   1320
ccatccaatt tcactgtgat cctagtttct gggctcaaaa tatcatcaac ttaggttctt   1380
tagtaatcga ggataaagag agccagccac aaatgcctaa gcagaatcct gtcgtggaac   1440
agaattcaca gccaccaagt ggtttatcat caaaccagtt atccaagttc caaacacaga   1500
tcagcctagc tcaattacgg ctccagcata tgcagcaaca ggtaatggct cagaggcaac   1560
aggtgcaacg gaggccagca cctgtgggtt taccaaaccc tagaatgcag ggcccatcc    1620 agcaaccttc catctctcat cagcaaccgc ctccacgttt gataaacttt cagaatcaca   1680
gccccaaacc caatggacca gttcttcctc ctcatcctca acaactgaga tatccaccaa   1740
accagaacat accacgacaa gcaataaagc caaaccccct acagatggct ttcttggctc   1800
aacaagccat aaaacagtgg cagatcagca gtggacaggg aaccccatca actaccaaca   1860
gcacatcctc tactccttcc agccccacga ttactagtgc agcaggatat gatggaaagg   1920
cttttggttc acctatgatc gatttgagct caccagtggg agggtcttat aatcttccct   1980
ctcttccgga tattgactgt tcaagtacta ttatgctgga caatattgtg aggaaagata   2040
ctaatataga tcatggccag ccaagaccac cctcaaacag aacggtccag tcaccaaatt   2100
catcagtgcc atctccaggc cttgcaggac ctgttactat gactagtgta cacccccaa    2160 tacgttcacc tagtgcctcc agcgttggaa gccgaggaag ctctggctct tccagcaaac   2220
cagcaggagc tgactctaca cacaaagtcc cagtggtcat gctggagcca attcgaataa   2280
aacaagaaaa cagtggacca ccggaaaatt atgatttccc tgttgttata gtgaagcaag   2340
aatcagatga agaatctagg cctcaaaatg ccaattatcc aagaagcata ctcacctccc   2400
tgctcttaaa tagcagtcag agctctactt ctgaggagac tgtgctaaga tcagatgccc   2460
ctgatagtac aggagatcaa cctggacttc accaggacaa ttcctcaaat ggaaagtctg   2520
aatggttgga tccttcccag aagtcacctc ttcatgttgg agagacaagg aaagaggatg   2580
accccaatga ggactggtgt gcagtttgtc aaaacgagg ggaactcctc tgctgtgaaa     2640
agtgccccaa agtattccat cttcttgtc atgtgcccac attgacaaat tttccaagtg    2700
```

```
gagagtggat tgcactttc tgccgagact tatctaaacc agaagttgaa tatgattgtg    2760
atgctcccag tcacaactca gaaaaaaga aaactgaagg ccttgttaag ttaacaccta    2820
tagataaaag gaagtgtgag cgcctacttt tatttcttta ctgccatgaa atgagcctgg    2880
cttttcaaga ccctgttcct ctaactgtgc ctgattatta caaaataatt aaaaatccaa    2940
tggatttgtc aaccatcaag aaaagactac aagaagatta ttccatgtac tcaaaacctg    3000
aagattttgt agctgatttt agattgatct ttcaaaactg tgctgaattc aatgagcctg    3060
attcagaagt agccaatgct ggtataaaac ttgaaaatta ttttgaagaa cttctaaaga    3120
acctctatcc agaaaaaagg tttcccaaac cagaattcag gaatgaatca gagataata    3180 aatttagtga tgattcagat gatgactttg tacagccccg gaagaaacgc tcaaaagca    3240 ttgaagaacg ccagttgctt aaataatatg cagcaccact agcttgtgct ggttttaga    3300 tttttttgtt tcaaaaaaaa catttgtcag taatttaaca tcactacaaa agaagagtt    3360 tgtgactatt ctcatctctg ttttggacgt ttactagact ttgatttcct taatagccca    3420
tttctgttaa cctcttatca ctaagaaaga aaggaaagaa ggagatgaat agaagaaaga    3480
aaatggaaag aaggaaaaaa ggaggataga aaaaggatgg aagaagaag cattgaaaac    3540 aaagacattc ttcccacttc ttggattttt aaaccacagt ctggagtgat agctactgta    3600
gaaaggaaat agactttgta tgaactcttt aagttgaaaa gtaaaaaata tatgtggttt    3660
ggatgtgtgc tttaattcag ctttagaaat taataccact acccgtgaat tatatggcct    3720
gacaatatga attaggtgta ctgtactgaa aacagtact ccacaaacat gggtggtaac    3780
aagagttcca tcccaggagg ccaaacggtg caacagaagg gtaggttaga tgctattaag    3840
aaggcactta atagtacatc atgtaagatg gcaactgtat taaagaaaaa tccgaaaaaa    3900
aaaaaaaaa                                                           3909
```

<210> SEQ ID NO 63
<211> LENGTH: 3807
<212> TYPE: DNA
<213> ORGANISM: homo sapiens

<400> SEQUENCE: 63

```
ccgcgagtcc accgagcggc ctctgaggag cagccgcagg aggaggagga ggtcgtcggg     60
ggcggcgggc ggagaccggc tcttctcgct tccccggcgg cggcaagggc aggacaatgg    120
aggtggcggt ggagaaggcg gtggcggcgg cggcagcggc ctcggctgcg gcctccgggg    180
ggccctcggc ggcgccgagc ggggagaacg aggccgagag tcggcagggc ccggactcgg    240
agcgcggcgg cgaggcggcc cggctcaacc tgttggacac ttgcgccgtg tgccaccaga    300
acatccagag ccgggcgccc aagctgctgc cctgcctgca ctctttctgc cagcgctgcc    360
tgcccgcgcc ccagcgctac ctcatgctgc ccgcgcccat gctgggctcg gccgagaccc    420
cgccacccgt ccctgccccc ggctcgccgg tcagcggctc gtcgccgttc gccacccaag    480
ttggagtcat tcgttgccca gtttgcagcc aagaatgtgc agagagacac atcatagata    540 actttttgt gaaggacact actgaggttc ccagcagtac agtagaaaag tcaaatcagg    600
tatgtacaag ctgtgaggac aacgcagaag ccaatgggtt ttgtgtagag tgtgttgaat    660
ggctctgcaa gacgtgtatc agagctcatc agagggtaaa gttcacaaaa gaccacactg    720
tcagacagaa agaggaagta tctccagagg cagttggtgt caccagccag cgaccagtgt    780
tttgtccttt tcataaaaag gagcagctga agctgtactg tgagacatgt gacaaactga    840
catgtcgaga ctgtcagttg ttagaacata aagagcatag ataccaattt atagaagaag    900
```

```
cttttcagaa tcagaaagtg atcatagata cactaatcac caaactgatg gaaaaaacaa    960
aatacataaa attcacagga aatcagatcc aaaacagaat tattgaagta aatcaaaatc   1020
aaaagcaggt ggaacaggat attaaagttg ctatatttac actgatggta gaaataaata   1080
aaaaaggaaa agctctactg catcagttag agagccttgc aaaggaccat cgcatgaaac   1140
ttatgcaaca acaacaggaa gtggctggac tctctaaaca attggagcat gtcatgcatt   1200
tttctaaatg ggcagtttcc agtggcagca gtacagcatt actttatagc aaacgactga   1260
ttacataccg gttacggcac ctccttcgtg caaggtgtga tgcatcccca gtgaccaaca   1320
acaccatcca atttcactgt gatcctagtt tctgggctca aaatatcatc aacttaggtt   1380
ctttagtaat cgaggataaa gagagccagc cacaaatgcc taagcagaat cctgtcgtgg   1440
aacagaattc acagccacca gtggtttat catcaaacca gttatccaag ttcccaacac   1500
agatcagcct agctcaatta cggctccagc atatgcagca acagcaaccg cctccacgtt   1560
tgataaactt tcagaatcac agccccaaac ccaatgacc agttcttcct cctcatcctc   1620
aacaactgag atatccacca aaccagaaca taccacgaca agcaataaag ccaaccccc   1680
tacagatggc tttcttggct caacaagcca taaaacagtg gcagatcagc agtggacagg   1740
gaacccatc aactaccaac agcacatcct ctactccttc cagccccacg attactagtg   1800
cagcaggata tgatgaaag gcttttggtt cacctatgat cgatttgagc tcaccagtgg   1860
gagggtctta taatcttccc tctcttccgg atattgactg ttcaagtact attatgctgg   1920
acaatattgt gaggaaagat actaatatag atcatggcca gccaagacca ccctcaaaca   1980
gaacggtcca gtcaccaaat tcatcagtgc catctccagg ccttgcagga cctgttacta   2040
tgactagtgt acaccccca atacgttcac ctagtgcctc cagcgttgga agccgaggaa   2100
gctctggctc ttccagcaaa ccagcaggag ctgactctac acacaaagtc ccagtggtca   2160
tgctggagcc aattcgaata aaacaagaaa acagtggacc accggaaaat tatgatttcc   2220
ctgttgttat agtgaagcaa gaatcagatg aagaatctag gcctcaaaat gccaattatc   2280
caagaagcat actcacctcc ctgctcttaa atagcagtca gagctctact tctgaggaga   2340
ctgtgctaag atcagatgcc cctgatagta caggagatca acctggactt caccaggaca   2400
attcctcaaa tggaaagtct gaatggttgg atccttccca gaagtcacct cttcatgttg   2460
gagagacaag gaaagaggat gaccccaatg aggactggtg tgcagtttgt caaaacggag   2520
gggaactcct ctgctgtgaa aagtgcccca agtattccca tcttcttgt catgtgccca   2580
cattgacaaa ttttccaagt ggagagtgga tttgcacttt ctgccgagac ttatctaaac   2640
cagaagttga atatgattgt gatgctccca gtcacaactc agaaaaaaag aaaactgaag   2700
gccttgttaa gttaacacct atagataaaa ggaagtgtga gcgcctactt ttatttcttt   2760
actgccatga aatgagcctg gcttttcaag accctgttcc tctaactgtg cctgattatt   2820
acaaaataat taaaaatcca atggatttgt caaccatcaa gaaaagacta caagaagatt   2880
attccatgta ctcaaaacct gaagattttg tagctgattt tagattgatc tttcaaaact   2940
gtgctgaatt caatgagcct gattcagaag tagccaatgc tggtataaaa cttgaaaatt   3000
attttgaaga acttctaaag aacctctatc cagaaaaaag gtttcccaaa ccagaattca   3060
ggaatgaatc agaagataat aaatttagtg atgattcaga tgatgacttt gtacagcccc   3120
ggaagaaacg cctcaaaagc attgaagaac gccagttgct taaataatat gcagcaccac   3180
tagcttgtgc tggttttag atttttttgt tttcaaaaaa acatttgtca gtaatttaac   3240
atcactacaa aaagaaggag tttgtgacta ttctcatctc tgttttgcag gtttacgccg   3300
```

-continued

| | |
|---|---|
| cacactttga tttccttaat agcccatttc tgttaaccta ttatcactaa gaaagaaagg | 3360 |
| aaagaaggag atgaatagaa gaaagaaaat ggaaagaagg aaaaaaggag gattgaaaaa | 3420 |
| ggatggaaga aagaagccat tgaaaacaaa gacattcttc ccacttcttg gattttaaaa | 3480 |
| ccacagtctg gagtgatagc tactgtagaa aggaaataga cttttatgaa ctctttaagt | 3540 |
| tgaaaagtaa aaatatatg tggtttggat gtgtgcttta attcagcttt agaaattaat | 3600 |
| accactaccc gtgaattata tggcctgaca atatgaatta ggtgtactgt actgaagaac | 3660 |
| agtactccac aaacatgggt ggtaacaaga gttccatccc aggaggccaa acggtgcaac | 3720 |
| agaagggtag gttagatgct attaagaagg cacttaatag tacatcatgt aagatggcaa | 3780 |
| ctgtattaaa gaaaaatccg gaaaacg | 3807 |

<210> SEQ ID NO 64
<211> LENGTH: 2854
<212> TYPE: DNA
<213> ORGANISM: homo sapiens

<400> SEQUENCE: 64

| | |
|---|---|
| atggagggcc cgcgctctgc ggcgtgtcgc gctcggccag caacttcccc gggcgctgtg | 60 |
| gacttgaccg cgccgccgcc gccgccgctg ctccgcattc tcaacagccg ggcggcccct | 120 |
| gccactcgca cttttgcaga cctctgtcgg agtctcctgc agccggaatc tcgggttctt | 180 |
| tgccggctgc agccagttaa ctgctacccg cccgctgcct ccacaaagct ttgtccagtt | 240 |
| ggagtcattc gttgcccagt ttgcagccaa gaatgtgcag agacacat catagataac | 300 |
| tttttttgtga aggacactac tgaggttccc agcagtacag tagaaaagtc aaatcaggta | 360 |
| tgtacaagct gtgaggacaa cgcagaagcc aatgggtttt gtgtagagtg tgttgaatgg | 420 |
| ctctgcaaga cgtgtatcag agctcatcag agggtaaagt tcacaaaaga ccacactgtc | 480 |
| agacagaaag aggaagtatc tccagaggca gttggtgtca ccagccagcg accagtgttt | 540 |
| tgtcctttc ataaaaagga gcagctgaag ctgtactgtg agacatgtga caactgaca | 600 |
| tgtcgagact gtcagttgtt agaacataaa gagcatagat accaatttat agaagaagct | 660 |
| tttcagaatc agaaagtgat catagataca ctaatcacca aactgatgga aaaaacaaaa | 720 |
| tacataaaat tcacaggaaa tcagatccaa aacagaatta ttgaagtaaa tcaaaatcaa | 780 |
| aagcaggtgg aacaggatat taagttgct atatttacac tgatggtaga aataaataaa | 840 |
| aaaggaaaag ctctactgca tcagttagag agccttgcag aggaccatcg catgaaactt | 900 |
| atgcaacaac aacaggaagt ggctggactc tctaaacaat tggagcatgt catgcatttt | 960 |
| tctaaatggg cagtttccag tggcagcagt acagcattac tttatagcaa acgactgatt | 1020 |
| acataccggt tacggcacct ccttcgtgca aggtgtgatg catccccagt gaccaacaac | 1080 |
| accatccaat ttcactgtga tcctagtttc tgggctcaaa atatcatcaa cttaggttct | 1140 |
| ttagtaatcg aggataaaga gagccagcca caaatgccta agcagaatcc tgtcgtggaa | 1200 |
| cagaattcac agccaccaag tggtttatca tcaaaccagt tatccaagtt cccaacacag | 1260 |
| atcagcctag ctcaattacg gctccagcat atgcagcaac agcaaccgcc tccacgtttg | 1320 |
| ataaactttc agaatcacag ccccaaaccc aatggaccag ttcttcctcc tcatcctcaa | 1380 |
| caactgagat atccaccaaa ccagaacata ccacgcaaag caataaagcc aaacccccta | 1440 |
| cagatggctt tcttggctca acaagccata aacagtggc agatcagcag tggacaggga | 1500 |
| accccatcaa ctacccaaaa tataaataca gcagcgtgca ctgtatttga tgtgagggtt | 1560 |
| cttcatcata taccctactg ggcattaaat ataagttcct ctgaaaggga ctcgttttg | 1620 |

```
tggttttcat ctgtctataa tttggaatga aaatgtgttg taggattttg ggagcaggca    1680
gctggggcga attaatagtg atttttttt tttttcctga agcatctatc tcatgttttt    1740
cttttgagag tcagaacatc aaacttaatc tttgatctga cttctgattt tattcttctg    1800
attgattgat agaggtacaa aagacttatc ttctgaggac aagcatattc ttaatgtgcc    1860
agacctaccc ggttcagctg atatagatag atagatagat agaagaaaat tgctgtgcca    1920
tacattaatc cagcatttga cacaatatct aaatggtttg ccgaagttaa tctgtattta    1980
taaaacatta actggagtaa attttctcc ttaggatgat agaataaaaa gagctcactt    2040
gaaagaaggc tattatttgc attatatcac ctgccataaa tttaacacag tctggagtga    2100
tagctactgt agaaaggaaa tagactttgt atgaactctt taagttgaaa agttaaatat    2160
atgtggtttg gatgtgtgct ttaattcagc tttagaaatt aataccacta cccgtgaatt    2220
atatggcctg acaatatgaa ttaggtgtac tgtactgaag aacagtactc cacaaacatg    2280
ggtggtaaca agagttccat cccaggaggc caaacggtgc aacagaaggg taggttagat    2340
gctattaaga aggcacttaa tagtacatca tgtaagatgg caactgtatt aaagaaaaat    2400
ccggaaaaca aatgtttgat ttttgttttt gtttttatct tgtctgtaga ggtattttgg    2460
tatagcaggt tttcaaggcc gttttttata catttctaga tctagatttt caacttcttc    2520
cactgaggga agtatataca tttgggtttg ctgtgtgtct atgtgaggtt taattgtaca    2580
ggtgatcctt ttacaacaag cctcattgtt tgcagtatag cttttagtgg aactacccaa    2640
aatataaaat acagggagaa aataacttgt tagcaataga tccccattgt ttatatatat    2700
aggtcttgtt cataatatgt caattatgta ttgttaaaaa gtcctactca cttttcaaat    2760
atgtgttaca tggtaatgtt tgtcattgtt gttttaaagt tgcatttgac atttgttctc    2820
caaagagtgt ttgaacagat tttgataaca gtgc                                 2854
```

P53 MODULATOR AND CANCER TARGET

STATEMENT REGARDING FEDERALLY SPONSORED RESEARCH

This invention was made with government support under GM081627 awarded by the National Institutes of Health. The government has certain rights in the invention.

CROSS-REFERENCE TO RELATED APPLICATIONS

This patent application is a national stage filing under 35 U.S.C. 371 of International Application No. PCT/IB2008/002504, filed Jul. 3, 2008, which claims priority benefits to U.S. Provisional Application No. 60/947,863, filed Jul. 3, 2007, and to Great Britain Patent Application No. 0723246.5, filed Nov. 27, 2007. These applications are incorporated herein by reference in their entireties.

FIG. 1 shows the full-length cDNA sequence (SEQ ID NO: 1) of human TRIM24. The start (ATG) and stop (TAA) codons of the coding sequence are boxed. The DNA sequence regions recognised by RNAi molecules according to the invention are indicated in bold. The 102 base region coding for the 34 amino acid insertion in the long TRIM24 isoform is underlined.

FIG. 2 shows the full-length protein sequence (SEQ ID NO: 2) of the TRIM24 long isoform. The 34 amino acid peptide sequence that is unique to the long isoform of TRIM24 is underlined.

FIELD OF THE INVENTION

The invention relates to the detection and treatment of cancers. In particular, the invention relates to the identification of a novel binding partner of p53, which shows modified expression patterns in certain cancer types; to methods for identifying modulators of the interaction between p53 and the novel binding partner; and the use of such modulators for the treatment of cancer.

BACKGROUND OF THE INVENTION

Cancer is the second leading cause of death in the United States. An estimated 10.1 million Americans are living with a previous diagnosis of cancer. In 2002, over one million people were newly diagnosed with cancer in the United States (information from Centres for Disease Control and Prevention, 2004 and 2005, and National Cancer Institute, 2005). According to Cancer Research UK, in 2005 over 150,000 people died in the UK as a result of cancer. It has been reported that almost 44,100 cases of breast cancer are diagnosed in the UK each year (i.e. 16% of all new cancer cases), and over 12,400 UK breast cancer patients die annually from this disease (approx. 8% of all deaths caused by cancer). One of the most common cancers is colon cancer, with approximately 21,600 new cases diagnosed in the UK during 2003. Colon cancer is also one of the most common causes of death from cancer, and it accounted for approximately 10% of all cancer-related deaths in 2005.

There is clearly a need to develop improved methods for diagnosis and treatment of cancers in the UK, the US and throughout the world.

Cancer is caused by the mutation of genes or the (change of) expression of genes that trigger uncontrolled cell division. There are two types of genes which when mutated may lead to cancer: (i) proto-oncogenes, which promote cell growth and mitosis, i.e. cell division (for example, mdm2 or the human homologue, hdm2); and (ii) tumour suppressor genes, which inhibit cell growth or halt cell division (for example, p53 and p21).

Proto-oncogenes often produce mitogens, which encourage cell division; or they may be transcription factors, transcription co-repressors or transcription co-activators, which can increase or change the expression of other genes. In particular, proto-oncogenes may encode proteins that regulate the expression or activity of tumour suppressor proteins. Viruses are another source of (proto-)oncogenes in humans, and it is thought that approximately 15% of human cancers worldwide originate from viral infections. The main viruses associated with human cancers are human papillomavirus, hepatitis B virus, Epstein-Barr virus, human T-lymphotropic virus and Kaposi's sarcoma herpesvirus.

Tumour suppressor genes typically encode anti-proliferation molecules that suppress mitosis and cell growth. Often, tumour suppressor proteins are also transcription factors, but their expression tends to be activated by cellular stress or DNA damage. Tumour suppressors generally function to arrest cell cycle progression, thereby giving the endogenous cellular processes time to repair any damaged DNA (resulting from the cellular stress) and prevent the multiplication of DNA mutations. Alternatively, for example, where a cell has been exposed to extreme levels of stress with little chance of recovery, a tumour suppressor may trigger apoptosis of the affected cell. Hence, where the expression of a tumour suppressor gene has been inhibited, DNA mutations are able to accumulate unchecked and, almost inevitably, will lead to cancer. The most common tumour suppressor gene associated with cancer is p53, which has been reported to display an altered expression profile and/or mutations in almost half of all cancers.

Detecting cancer at an early stage in the development of the disease is a key factor in enabling the disease to be effectively treated and prolonging the life of the affected individual. Cancer screening is an attempt to detect (undiagnosed) cancers in the population, so as to enable early therapeutic intervention. Screens for detecting and/or predicting cancer are advantageously suitable for testing large numbers of subjects; are affordable; safe; non-invasive; and accurate (i.e. exhibiting a low rate of false positives).

A number of different screening tests have been developed, many of which involve visual/tactile examination, e.g. for breast or testicular cancer. However, many cancers cannot be detected by such crude examinations and, in these cases, other forms of physical and/or biochemical examinations may be required. For instance, screening by mammogram can detect a breast tumour earlier than self-examination; colorectal cancer can be detected, for example, through faecal occult blood testing and colonoscopy; and cervical cytology testing (smear test) can lead to the identification of precancerous lesions. Meanwhile, a screen for prostate cancer uses a digital rectal exam along with a blood test to detect prostate specific antigen (PSA).

There remains, however, a large number of different types of human cancer, which are not readily detectable, or reliably detectable, by present screening methods, prior to the onset of disease symptoms (by which time it may be too late for an effective intervention). Accordingly, there is a need for further cancer detection/screening methods, particularly biochemical methods, which will allow the detection of cancer before the onset of disease symptoms. There is also a need for additional screens to supplement and/or confirm the diagnoses from cancer screens already known in the art.

The p53 tumour suppressor is a key component of the cellular processes that maintain genomic integrity in response to cellular stress and/or DNA damage (Levine, 1997, *Cell*, 88(3): 323-331) and, as already noted, aberrations in p53 are associated with over half of all human cancers. Under normal conditions, p53 and its cellular activity are maintained at low levels by a combination of rapid degradation and inhibition, both of which activity regulation processes are thought to be largely controlled by the product of the mdm2 (or hdm2 in humans) proto-oncogene. The hdm2 protein has been shown to bind to the transactivation domain of p53 and inhibit its transactivation activity (Momand et al., 1992, *Cell*, 69(7): 1237-1245). In addition, it has been reported that hdm2 functions as an E3 ubiquitin ligase (Honda at al., 1997, *FEBS Lett.*, 420), which acts on p53 to target it for proteasomal degradation via a ubiquitin-dependent pathway (Haupt at al., 1997, *Nature (London)*, 387: 296-299; Kubbutat at al., 1997, *Nature (London)*, 387: 299-303). Significantly, the expression of the hdm2 gene is itself controlled by p53 and, therefore, both the cellular concentration and the activity of p53 are under the control of an auto-regulatory feedback loop involving hdm2.

As a result of cellular stress, for example, DNA damage induced by UV radiation or mutagens, p53 is transiently stabilised (by phosphorylation in its N-terminal domain), which prevents the binding of hdm2 and stabilises its active conformation. Once activated, p53 induces the transcription of a number of genes, including p21, bax and hdm2 (as previously described). Both p21 and bax proteins mediate the anti-proliferative function of p53 by blocking cell cycle progression and/or provoking cell apoptosis (El-Deiry at al., 1995, *Cancer Res.*, 55: 2910-2919; Miyashita & Reed, *Cell*, 80(2): 293-299). The tumour suppressor protein p21 (also known as "cyclin-dependent kinase inhibitor 1A" or "CDKN1A" because of its mode of action), plays an important role in mediating cell cycle arrest in the $G_1$-, $G_2$- or S-phase when cellular DNA is damaged. It has been demonstrated that both p21 and p53 are essential for stabilising the $G_2$ checkpoint after DNA damage in human cells (Bunz at al., 1998, *Science*, 282: 1497-1501).

That p53 is associated with the onset and/or progression of so many cancers, makes it a prime target for regulation or modification for cancer therapy. In addition, the genes and/or proteins that are activated or repressed by p53, and conversely, those that are responsible for controlling the activation or repression of p53 may also be useful targets for anti-cancer drugs and treatments.

One p53-interacting protein is hdm2 (as previously discussed); another is TRIM28 (tripartite motif-containing 28, also known as KAP1, Krip1, RNF96, TF1B, TIF1B, TIF1 beta, TIF1β, UniProtKB/Swiss-Prot entry Q13263), which is a member of the family of proteins that contains a TIF1 domain structure. The TIF1 domain comprises an N-terminal region having an RBCC (RING finger-B boxes-coiled coil) motif; a poorly conserved central region; and a C-terminal region containing a PHD finger and a bromodomain or "BROMO" (see for example, Le Douarin et al., 1996, *EMBO J.*, 15: 6701-6715). TRIM28 has been identified almost exclusively as a non-enzymatic component of transcriptional regulatory complexes (Friedman et al., 1996, *Genes Dev.*, 10: 2067-2078; Moosmann et al., 1996, *Nucleic Acids Res.*, 24: 4859-4867). Although not believed to bind DNA itself, TRIM28 is known to interact with a wide variety of nuclear factors including KRAB repressors (Kim et at., 1996, *Proc. Natl. Acad. Sci. USA*, 93: 15299-15304); the histone-binding protein HP1; SETDB1 (ESET); and hdm2 (Wang et al., 2005, *EMBO J.*, 24: 3279-3290). In fact, TRIM28 is thought to be a member of several larger multi-factor complexes that typically function in the repression of gene expression and the stabilisation of heterochromatin (Sripathy et al., 2006, *Mol. Cell. Biol.*, 26: 8623-8638).

Other members of the TRIM family include: TRIM25 (also known as EFP, RNF147, Z147 and ZNF147), in which the RING domain has been shown to possess E3 ubiquitin ligase activity that is important in mediating anti-viral activity (Gack, et al., 2007, Nature, 446: 916-920); and TRIM33 (also known as PTC7, RFG7, TF1G, TIF1G, FLJ32925, TIF-gamma, TIF1gamma and TIF1γ), which also has been shown to exhibit E3 ubiquitin ligase activity via its RING domain (Dupont et al., 2005, *Cell*, 121: 87-99).

Another member of the TRIM family, that is also a member of the TIF1 protein sub-family, is TRIM24 (also known as PTC6, TF1A, TIF1, RNF82, TIF1A, hTIF1, TIF1ALPHA and TIF1α), which is known to interact with certain nuclear receptors and to possess a kinase activity (Fraser et al., 1998, *J. Biol. Chem.*, 273: 16199-16204). More specifically, TRIM24 has been shown to mediate transcriptional control by interacting with the AF2 (activation function 2) activating domain of selected nuclear receptors (NRs) including the oestrogen, retinoic acid and vitamin D receptors (Thenot et al., 1997, *J. Biol. Chem.*, 272(18): 12062-12068). In this study it was suggested that TRIM24 may regulate transcription by a mechanism of chromatin remodelling, rather than through the transcriptional machinery. TRIM24 has also been shown to interact with heterochromatin-associated proteins (Le Douarin of at., 1996, *EMBO J.*, 15: 6701-6715). Another recent publication has indicated that TRIM24 is involved in the modulation of gene expression during the first transcriptional wave at the zygote (1-cell) stage (Torres-Padilla & Zernicka-Goetz, 2007, *J. Cell Biol.*, 174: 329-338), which further suggests a possible epigenetic role for TRIM24.

There have been no previous reports of an interaction between TRIM24 and p53, or evidence for the direct involvement of TRIM24 in p53-associated cancers. Similarly, there is no reported evidence for an E3 ligase activity for TRIM24 (c.f. TRIM25 and TRIM33).

The present invention seeks to overcome or at least alleviate some of the aforementioned problems in the art, for example, first by identifying factors that may be involved in disease states such as cancer, and particularly, cancers that are associated with p53 alterations; and then by identifying modulators of p53 activity for treating cancer.

SUMMARY OF THE INVENTION

The present invention is based in part on the identification of TRIM24 (tripartite motif-containing 24, PTC6, TF1A, TIF1, RNF82, TIF1A, hTIF1, TIF1ALPHA and TIF1α) as a p53-binding protein, and also on the observation that TRIM24 is differently expressed (typically above "normal" levels) in certain cancer cell types. The present invention is also based on the identification of molecules that modulate the activity of p53, particularly via the regulation of TRIM24 expression and/or activity, and the use of such molecules for the treatment of cancer.

Thus, in a first aspect of the invention, there is provided a method of identifying a modulator of TRIM24 activity comprising: (i) exposing a TRIM24 polypeptide to a plurality of candidate compounds; (ii) determining whether one or more of the candidate compounds interacts with TRIM24 in such as way as to modulate the activity of TRIM24; and (iii) identifying a compound that interacts with TRIM24 in such as way as to modulate the activity of TRIM24 as a modulator of TRIM24. The activity may be any functional activity of TRIM24, such as the ability to bind/interact with p53, or it may be a catalytic activity. Suitably, the catalytic activity of TRIM24 is an E3 ligase and/or a kinase activity. Advantageously, the activity is an E3 ligase (ubiquitylation/sumoylation) activity.

Where the activity of TRIM24 is an E3 ligase activity, the method may suitably comprise: assessing the E3 ligase activity of a TRIM24 polypeptide or a fragment thereof in an E3 ligase assay to determine a base-level ubiquitylation/sumoylation activity for the TRIM24 polypeptide or fragment thereof; contacting the TRIM24 polypeptide or fragment thereof with the one or more candidate compounds; assessing the E3 ligase activity of the TRIM24 polypeptide or fragment thereof in an E3 ligase assay in the presence of the one or more candidate compounds to determine a test activity for the TRIM24 polypeptide or fragment thereof in the presence of the one or more candidate compounds; and determining whether the base-level E3 ligase activity for the TRIM24 polypeptide or fragment thereof is different to the test activity; and where the base-level E3 ligase activity is different to the test ubiquitylation activity for the TRIM24 polypeptide or fragment thereof in the presence of the one or more candidate compounds, identifying that compound as a modulator of TRIM24.

Accordingly, in a second aspect of the invention there is provided a method of identifying a modulator of p53 activity, comprising: (a) expressing p53 and TRIM24 in the presence of a p53-responsive nucleic acid reporter construct; (b) detecting a level of expression of the reporter construct in the presence of p53 and TRIM24; (c) introducing a candidate modulator molecule; and (d) determining whether the molecule alters the level of expression of the p53-responsive reporter in the presence of p53 and TRIM24; and thereby identifying the candidate molecule that alters the level expression of the p53-responsive reporter in the presence of p53 and TRIM24 as a modulator of p53 activity. The method is carried out in vitro in the sense that the p53 and TRIM24 proteins are not expressed inside a living cell, for example, a cell extract or lysate may conveniently be used; or the method may be carried out within a cell. Suitably, the cell is a eukaryotic cell. Any suitable reporter construct/gene may be used, advantageous examples are the gene coding for luciferase, GFP or CAT. Luciferase is a particularly convenient reporter gene. The molecule may increase or decrease the expression of the reporter gene. Beneficially, the molecule decreases the expression of the reporter in comparison to the level of reporter expression in the presence of both p53 and TRIM24.

In some embodiments the method may further comprise the steps of: detecting a first level of expression of the reporter in the presence of p53 and TRIM24; detecting a second level of expression of the reporter in the presence of p53, TRIM24 and the candidate molecule; and wherein the first level of expression is different to the second level of expression, identifying the candidate molecule as a modulator of p53.

The candidate molecule may be any chemical entity, such as a nucleic acid (single-stranded or double-stranded DNA or RNA); a polypeptide; a small molecule, or other chemical compound, for example, a chemically synthesised drug. Beneficially, the candidate molecule is a "small molecule", for example, a molecule that can be obtained from a small molecule drug-screening library. Suitably, when the candidate molecule is an RNA molecule, it is selected from an shRNA or siRNA molecule.

In a second aspect there is provided a modulator of p53 activity identified by the methods of the invention. The modulator is a molecule (compound or chemical entity) that is identified as having a modulatory effect on p53. Suitably, the modulator of p53 activity is an siRNA molecule that down-regulates the expression of TRIM24. In one embodiment the modulator of p53 activity is a chemical compound that inhibits the binding of TRIM24 to p53. The modulator of p53 activity may, for example, be a polypeptide, such as an antibody or antigen-binding portion thereof that inhibits the binding of TRIM24 to p53. In some embodiments the modulator of p53 activity is a chemical entity that inhibits an enzymatic activity of TRIM24. Suitably, the enzymatic activity that is inhibited is an E3 ubiquitin ligase activity. The invention encompasses such molecules for use in medicine, and suitably, their use for modulating p53 activity by targeting TRIM24.

The invention also encompasses pharmaceutical compositions comprising a modulator of p53 activity identified by the methods of the invention; and the use of such a modulator of p53 activity in the manufacture of a medicament for treating cancer in an individual. Suitably, the cancer is associated with an up-regulation of TRIM24 expression and/or activity in the cancer cells. Also encompassed within the scope of the invention is a method of treating cancer in an individual, comprising administering a modulator of p53 activity identified by the methods of the invention; and similarly, a method of treating cancer in an individual, comprising administering a modulator of TRIM24 activity identified by the methods of the invention.

In another aspect of the invention, there is provided an antibody or antigen binding portion thereof that specifically binds to a TRIM24 polypeptide. Suitably, the antibody specifically binds to an antigenic region of TRIM24.

In any of the aspects of the invention, the antibody or antigen binding portion thereof is selected from the group consisting of: a polyclonal antibody, a monoclonal antibody, a humanised monoclonal antibody derived from a murine monoclonal antibody, a human monoclonal antibody. The antigen binding portion of an antibody may for example, comprise Fab fragments, F(ab')2 fragments and Fv fragments.

In a fifth aspect of the invention, there is provided an siRNA or shRNA molecule that targets TRIM24 mRNA. In another aspect, the siRNA or shRNA molecule of the invention is for use in medicine. In these aspects of the invention the siRNA or shRNA molecule suitably targets at least 19 contiguous bases of a sequence of TRIM24 mRNA. The target sequence is advantageously selected from SEQ ID NO: 1 (FIG. 1A) or the RNA equivalent thereof. Beneficially, the siRNA of shRNA molecule targets between 19 and 22 contiguous bases of SEQ ID NO: 1, and advantageously targets between 19 and 21 contiguous bases of SEQ ID NO: 1. Suitably, the siRNA or shRNA molecule of the invention is for use in down-regulating the expression of TRIM24 for the treatment of cancer; and particularly, for the treatment of cancer associated with p53. In some advantageous embodiments, the siRNA or shRNA molecule of the invention targets at least 19 consecutive bases of the sequence: CGCATGAAACTTATGCAACAAC (SEQ ID NO: 7), GCCATGAAATGAGCCTGGCTTT (SEQ ID NO: 8), CCTGTTGTTATAGTGAAGCAA (SEQ ID NO: 9), GGCAGCAGTACAGCATTACTTT (SEQ ID NO: 10), or CGAGACTTATCTAAACCAGAA (SEQ ID NO: 11); or a sequence complementary thereto.

In certain embodiments, the siRNA molecule is selected from the oligonucleotide pairs:
(a) 5'-CGCATGAAACTTATGCAACAAC-3' (sense strand, SEQ ID NO: 7) and
5'-GTTGTTGCATAAGTTTCATGCG-3' (antisense strand, SEQ ID NO: 12);

(b) 5'-GCCATGAAATGAGCCTGGCTTT-3' (sense strand, SEQ ID NO: 8) and
5'-AAAGCCAGGCTCATTTCATGGC-3' (antisense strand, SEQ ID NO: 13);
(c) 5'-CCTGTTGTTATAGTGAAGCAA-3' (sense strand, SEQ ID NO: 9) and
5'-TTGCTTCACTATAACAACAGG-3' (antisense strand, SEQ ID NO: 14);
(d) 5'-GGCAGCAGTACAGCATTACTTT-3' (sense strand, SEQ ID NO: 10) and
5'-AAAGTAATGCTGTACTGCTGCC-3' (antisense strand, SEQ ID NO: 15);
(e) 5'-CGAGACTTATCTAAACCAGAA-3' (sense strand, SEQ ID NO: 11) and
5'-TTCTGGTTTAGATAAGTCTCG-3' (antisense strand, SEQ ID NO: 16).

In other embodiments, the shRNA molecule is suitably selected from:

```
                                             (SEQ ID NO: 17)
5'CCGGCGCATGAAACTTATGCAACAACTCGAGTTGTTGCATAAGTTTCA
TGCGTTTTT-3';

(SEQ ID NO: 18)
5'CCGGCCATGAAATGAGCCTGGCTTTCTCGAGAAAGCCAGGCTCATTTC
ATGGTTTTT-3';

(SEQ ID NO: 19)
5'CCGGCCTGTTGTTATAGTGAAGCAACTCGAGTTGCTTCACTATAACAA
CAGGTTTTT-3';

(SEQ ID NO: 20)
5'CCGGGCAGCAGTACAGCATTACTTTCTCGAGAAAGTAATGCTGTACTG
CTGCTTTTT-3';
and (SEQ ID NO: 21)
5'CCGGCGAGACTTATCTAAACCAGAACTCGAGTTCTGGTTTAGATAAGT
CTCGTTTTT-3'.
```

Optionally, siRNA molecules and shRNA molecules according to the invention further comprise dTdT or UU 3'-overhangs, and/or nucleotide and/or polynucleotide backbone modifications as described elsewhere herein.

In yet another aspect of the invention, there is provided the use of an inhibitor of TRIM24 expression and/or biological activity in the manufacture of a medicament for the treatment of cancer. Suitably, the inhibitor of TRIM24 comprises a moiety selected from: a polynucleotide that is substantially complementary to a TRIM24 polynucleotide sequence; an oligonucleotide that is substantially complementary to at least 12 contiguous bases of a TRIM24 polynucleotide sequence; an oligonucleotide RNAi molecule that is substantially complementary to at least 19 contiguous bases of a TRIM24 polynucleotide sequence; an antibody; a small molecule; an artificial transcription factor; a glycoprotein; and a polysaccharide. In some embodiments, the inhibitor of TRIM24 biological activity antagonises the binding interaction between TRIM24 and p53; and more suitably, the inhibitor of TRIM24 biological activity antagonises an enzymatic activity of TRIM24, such as E3 ligase activity (e.g. ubiquitylation/sumoylation activity). Suitably, the inhibitor of TRIM24 expression is an siRNA or shRNA molecule that targets at least 19 contiguous bases of human TRIM24 and its isoforms (see SEQ ID NOs: 1 and 59-64). More suitably, the inhibitor of TRIM24 expression is an shRNA molecule or an siRNA molecules are described herein.

In another aspect of the invention there is provided a pharmaceutical composition for the prevention and/or treatment of cancer in a patient in need thereof, comprising an inhibitor of TRIM24 expression and/or biological activity and a pharmaceutically acceptable carrier. In yet another aspect the invention provides a composition comprising an inhibitor of TRIM24 expression and/or biological activity for use as a modulator of p53 signalling pathways. In such aspects and embodiments, the inhibitor of TRIM24 suitably comprises a moiety selected from: a polynucleotide that is substantially complementary to a TRIM24 polynucleotide sequence; an oligonucleotide that is substantially complementary to at least 12 contiguous bases of a TRIM24 polynucleotide sequence; an oligonucleotide RNAi molecule that is substantially complementary to at least 19 contiguous bases of a TRIM24 polynucleotide sequence; an antibody; a small molecule; an artificial transcription factor; a glycoprotein; and a polysaccharide. Preferably, at the polynucleotide level, the inhibitor of TRIM24 is an antisense RNA, siRNA or shRNA molecule; and at the polypeptide level, the inhibitor of TRIM24 is an antibody or an antigen-binding site thereof, or alternatively a small molecule inhibitor. Advantageously, the inhibitor of TRIM24 biological activity antagonises the binding interaction between TRIM24 and p53. In another embodiment the inhibitor of TRIM24 biological activity antagonises an enzymatic activity of TRIM24, such as its E3 ligase activity (e.g. ubiquitylation activity). Suitably in compositions comprising siRNA and/or shRNA molecules, the shRNA molecule or siRNA molecule is as described herein before (for example, in accordance with the fifth aspect of the invention).

In a further aspect of the invention, there is provided a method of treating cancer in a patient in need thereof, comprising administering to a patient in need thereof an effective amount of an inhibitor of TRIM24, which inhibitor comprises a moiety selected from: a polynucleotide that is substantially complementary to a TRIM24 polynucleotide sequence; an oligonucleotide that is substantially complementary to at least 12 contiguous bases of a TRIM24 polynucleotide sequence; an oligonucleotide RNAi molecule that is substantially complementary to at least 19 contiguous bases of a TRIM24 sequence; an antibody; a small molecule; an artificial transcription factor; a glycoprotein; and a polysaccharide. Suitably, the inhibitor of TRIM24 comprises an siRNA or shRNA molecule that targets at least 19 contiguous bases of human TRIM24 and its isoforms (see SEQ ID NOs: 1 and 59-64). More suitably, the siRNA or shRNA molecule targets 19 to 21 contiguous bases of human TRIM24 and its isoforms (see SEQ ID NOs: 1 and 59-64). Advantageously, in embodiments of this aspect of the invention, the siRNA or shRNA molecule is as described elsewhere herein.

Other aspects of the invention also provide a method of treating cancer in a patient in need thereof, comprising administering effective amounts of the pharmaceutical composition described herein to the patient. Also provided is the use of an inhibitor of TRIM24 expression and/or biological activity in the manufacture of a medicament for the treatment of cancer, wherein the inhibitor is as described herein.

BRIEF DESCRIPTION OF THE DRAWINGS

FIGS. 1A-B show the full-length cDNA sequence (SEQ ID NO: 1) of human TRIM24. The start (ATG) and stop (TAA) codons of the coding sequence are boxed. The DNA sequence regions recognized by RNAi molecules according to the invention are indicated in bold. The 102 base region coding for the 34 amino acid insertion in the long TRIM24 isoform is underlined.

FIG. 2 shows the full-length protein sequence of the TRIM24 long isoform. The 34 amino acid peptide sequence that is unique to the long isoform of TRIM24 is underlined.

FIGS. 9A-J show multiple sequence alignments of the human TRIM24 protein coding transcripts available in the public domain, with the respective accession numbers shown on the left (SEQ ID NOs: 59 to 64). The positions of siRNA sequences utilized in the invention which were expected to be in common to all isoforms/variants of TRIM24 are marked on the figures. Underlined sequences represent siRNA target. A * refers to sequence which is the same for all transcripts. A − refers to a gap inserted by CLUSTAL during the alignment process. Numbers at the end of the sequence refer to base pairs.

FIG. 10 shows the siRNA target sequences described in FIG. 9. The sense sequences represent SEQ ID NOs: 28 to 36 respectively; whilst the antisense sequences represent SEQ ID NOs: 37 to 45 respectively.

DETAILED DESCRIPTION

Figure 3:
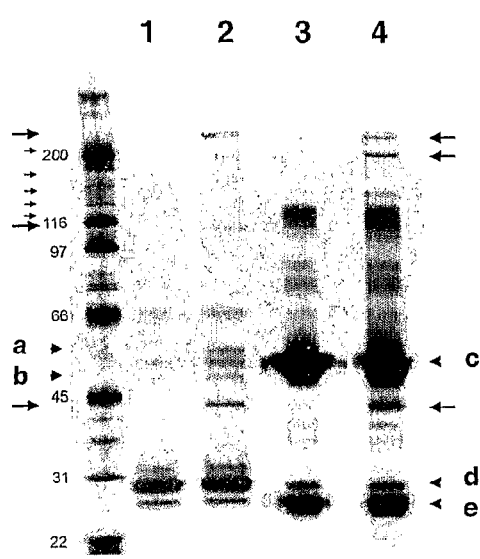
FIG. 3 shows the results of TAP-purification of p53-protein complexes analysed by silver-stained SDS-PAGE. Mouse embryonic stem (mES) cells expressing either TAP-p53 (p53 tagged with TAP, a short peptide consisting of Protein A and Calmodulin-Binding Protein motifs, separated by a tobacco etch virus (TEV) protease cleavage site) or wild-type (wt) p53 were exposed to doxorubicin, prior to extract preparation and TAP purification using microbeads coated with antibody to the Protein A epitope of the TAP tag. Beads with bound proteins were then treated with TEV protease, which releases proteins bound only via the TAP-p53 protein. Proteins were separated by SDS-PAGE and silver stained. Polypeptides eluted from the beads following TEV treatment are shown in lane 1 for wt p53-expressing mES cells, and in lane 2 for the TAP-p53-expressing mES cells. Proteins bound to beads and not released by TEV treatment (i.e. proteins not bound directly via TAP-p53) are also shown in lane 3 for wt p53-expressing mES cells, and in lane 4 for the TAP-p53-expressing mES cells. Proteins from lanes 3 and 4 were not analysed by mass spectrophotometry. Arrows indicate protein bands analysed by mass spectrophotometry, as well as identified TAP-p53 (a), p53 (b), IgG heavy chain (c) and light chain (e) and TEV protease (d).

Prior to setting forth the detailed description of the invention, a number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

The term 'cancer' is used herein to denote a tissue or a cell located within a neoplasm or with properties associated with a neoplasm. Neoplasms typically possess characteristics that differentiate them from normal tissue and normal cells. Among such characteristics are included, but not limited to: a degree of anaplasia, changes in cell morphology, irregularity of shape, reduced cell adhesiveness, the ability to metastasise, increased levels of angiogenesis, increased cell invasiveness, reduced levels of cellular apoptosis and generally increased cell malignancy. Terms pertaining to and often synonymous with 'cancer' include sarcoma, carcinoma, tumour, epithelioma, leukaemia, lymphoma, polyp, transformation, neoplasm and the like. As used herein, the term p53-associated cancer (or similar) refers to a cancer in which the expression or function of p53 is altered in relation to a normal cell. The alteration in expression or function may be caused by mutations in the p53 gene itself, or by mutations in or altered expression of genes that directly or indirectly affect the expression or function of p53.

By the term "normal", for example, in the context of a "normal cell", it is meant a cell that is not known to be diseased, and particularly a cell that is not a cancer cell. Typically, such a cell would be obtained from a healthy subject, i.e. a subject that does not have a cancer. However, within an individual there may be cells of a particular type (e.g. B-cells) that are cancerous, and cells of the same or other type e.g. spleen, that are not cancerous and so are "normal". Therefore, it some circumstances it may be possible to obtain normal cells from a subject who has cancer.

Normal cells can be used as "control" cells (or "controls") to detect and/or quantify the expression of a particular gene, such as TRIM24 in a non-diseased or at least a non-cancer cell. The level of expression of the gene in a normal cell is considered to be the "normal", "control" or "baseline" level of expression. Thus, in accordance with the present invention, the expression of TRIM24 in a cancer cell is typically compared to the baseline level of TRIM24 expression in a normal, healthy control cell, advantageously of the same cell type.

By the term "modulator" it is meant a molecule (e.g. a chemical substance/entity) that effects a change in the activity of a target molecule (e.g. a gene, enzyme etc.). The change in activity is relative to the normal or baseline level of activity in the absence of the modulator, but otherwise under similar conditions, and it may represent an increase or a decrease in the normal/baseline activity. The modulator may be any molecule as described herein, for example a small molecule drug, an antibody or a nucleic acid. In the context of the present invention, the target molecule is the p53 gene, RNA or protein; such that a modulator is categorised by its ability to modulate the activity of p53 and/or TRIM24 (typically within a target cell, but it includes modulation demonstrated in vitro). The modulation of p53 and/or TRIM24 may be assessed by any means known to the person skilled in the art; for example, by identifying a change in the expression of genes regulated by p53 and/or TRIM24. Advantageously, in accordance with the invention, the modulator exerts its effect on p53 activity via the TRIM24 gene, RNA or protein. Therefore, by way of example, the modulator may act by changing the expression of the TRIM24 gene; by changing the expression of TRIM24 RNA (e.g. catalysing its degradation); by inhibiting an enzymatic activity of the TRIM24 protein; or by causing a change in TRIM24 protein structure or function. Thus, by "modulate activity", it is meant that the activity of the target (e.g. p53 or TRIM24) is caused to change from its normal/baseline activity.

The term "epigenetic modification" refers to the chemical marking of the genome. Epigenetic marks can include covalent modifications of DNA (e.g. methylation, "imprints") as well as proteins associated with DNA, such as by (but limited to) methylation or acetylation of histones. Parent-of-origin-specific gene expression (either from the maternal or paternal chromosome) is often observed in mammals and is due to epigenetic modifications. In the parental germlines, epigenetic modification can lead to stable gene silencing or activation.

The terms "derivative" or "homologues" of TRIM24 as used herein refer to polynucleotides (e.g. mRNA) and/or polypeptides that have substantially similar sequence identity to that of TRIM24. Advantageously, the TRIM24 to which the sequence identity is compared is human TRIM24. Derivatives and homologues are considered to include orthologues of the sequences from other species, and mutants that nonetheless exhibit a high level of functional equivalence. By substantially similar sequence identity, it is meant that the level of sequence identity is from about 50%, 60%, 70%, 80% or 90% identical to the respective TRIM24 (e.g. to human TRIM24). Advantageously, the substantially similar sequence identity is at least about 92%, 95% or about 98% identical to human TRIM24. In some particularly advantageous embodiments, a polypeptide having substantially similar sequence identity to TRIM24 is about 99% or 100% identical to human TRIM24. Percent sequence identity can be determined using conventional methods (e.g. Henikoff & Henikoff, 1992, *Proc. Natl. Acad. Sci. USA*, 89: 10915; and Altschul et al., 1997, *Nucleic Acids Res.*, 25: 3389-3402). It will be appreciated that the level of sequence identity described herein refers to both polypeptide sequences and polynucleotide sequences (DNA or RNA).

The term "isolated", when applied to a nucleic acid or polypeptide sequence is a sequence that has been removed from its natural organism of origin. Typically, an isolated polypeptide or polynucleotide/nucleic acid molecule has been removed from the environment in which it was produced; although, it is not necessarily in a pure form. That is, an isolated polypeptide or polynucleotide is not necessarily 100% pure, but may be about 10%, 20%, 30%, 40%, 50%, 60%, 70%, 80% or 90% pure. A purified, isolated polypeptide or polynucleotide is advantageously at least 80% pure, and may be at least 90%, at least 95% or at least 98% pure (e.g. 99% pure). In the present context, the term "isolated" when applied to a polypeptide is intended to include the same polypeptide in alternative physical forms whether it is in the native form, denatured form, dimeric/multimeric, glycosylated, crystallised, or in derivatised forms. Advantageously, the nucleic acid molecules/polynucleotides/oligonucleotides (e.g. nucleic acid probes, RNAi molecules etc.), and polypeptides/peptides (e.g. antibodies or fragments thereof) of the invention are isolated; and more beneficially, purified.

The present invention relates in part to the identification of TRIM24 as a p53-interacting (e.g. binding) protein, and in part to the fact that TRIM24 is differentially expressed in certain cancer cell types. Accordingly, methods and compositions based upon TRIM24 are provided for the detection and/or diagnosis of cancer; and for the modulation of signalling pathways involving p53. In particular, the data set out herein indicates that TRIM24 is differentially expressed in several cancer cell types, in comparison to the respective normal cells. In certain cancer cell types it has been shown that TRIM24 expression is up-regulated in comparison to the respective normal cells (e.g. breast cancer, retinal cancer, colon cancer and prostate cancer); and in one cancer cell type it has been shown that TRIM24 expression is down-regulated in comparison to the respective normal cell type (renal cancer). Significantly, the present invention also shows that inhibition of TRIM24 activity or expression in the sub-set of cancer cells that express p53 has a marked effect on their ability to proliferate.

TRIM24 is also developmentally regulated, for example, during embryonic development (Torres-Padilla & Zernicka-Goetz, 2006, *J. Cell Biol.*, 174(3): 329-338).

The data provided herein further indicates that TRIM24 expression has an effect on the expression of a number of key genes involved in cancer and in development, and identifies TRIM24 as a target for anti-cancer therapy.

Tripartite Motif-Containing 24 Protein (TRIM24)

TRIM24 is a member of the tripartite motif-containing (TRIM) family of proteins, which each possess an N-terminal region having an RBCC (RING finger-B boxes-coiled coil) motif; a poorly conserved central region; and a C-terminal region containing a PHD finger and a bromodomain (Le Douarin et al., 1996, *EMBO J.*, 15: 6701-6715). Other members of the TRIM family of proteins, which include TRIM28 and TRIM33, are also known as transcription intermediary factors (TIF) because of their known cellular activities. To date TRIM proteins have been shown to exhibit quite different cellular activities and functions.

Two isoforms of TRIM24 have been reported in both mice and humans (Le Douarin et al., 1995, *EMBO J.*, 14: 2020-2033). Both isoforms contain the recognised functional domains: RING, BBOX, BBC, PHD and BROMO. However, the longer isoform also contains a 34 amino acid insertion (shown underlined in FIG. 2), which is encoded by a 102 base pair (bp) sequence also indicated by underlining in the human TRIM24 cDNA and RNA sequences shown in FIG. 1. There have been no reported differences in the functions of these two isoforms and, therefore, the significance of the different isoforms is unclear. Hence, as used herein, the term TRIM24 refers to both of the known isoforms of TRIM24; i.e. the long and short isoforms of human TRIM24.

TRIM24 (a TIF protein) is considered to mediate transcriptional control by interacting in a ligand-dependent manner with the activation function 2 (AF2) activating domain of several nuclear receptors (NRs), including oestrogen, retinoic acid and vitamin D (Thenot at al., 1997, *J. Biol. Chem.*, 272(18): 12062-12068; Le Douarin at al., 1995, *EMBO. J.*, 14(9): 2020-2033). Upon binding to a suitable NR, it appears that TRIM24 localises to nuclear bodies (Le Douarin et al., 1997, *Biochem Soc Trans.*, 25: 605-612). In Fraser at al. (1998, *J. Biol. Chem.*, 273: 16199-16204) it was reported that TRIM24 also possesses a kinase activity, and is itself hyperphosphorylated on interacting with an appropriate NR. Such post-translational modifications likely play a very important role in the function(s) of TRIM24. For instance, post-translational modifications are known to affect enzymatic activity, stability and protein-protein (or protein-nucleic acid) interactions. Other TRIM-family members have been shown to associate with each other and with other TRIM proteins, e.g. PML. It may be that TRIM24 also interacts with itself and/or other TRIM proteins to form homo- or hetero-dimers and possibly also multimers.

It has also been suggested that TRIM24 may regulate transcription by a mechanism of chromatin remodelling, rather than through the transcriptional machinery. In this regard, Le Douarin et al. (1996, *EMBO J.*, 15: 6701-6715) demonstrated that TRIM24 can interact with heterochromatin-associated proteins. This observation, together with data that indicate the involvement of TRIM24 in the modulation of gene expression during the first transcriptional wave at the zygote (1-cell) stage (Torres-Padilla & Zernicka-Goetz, 2007, *J. Cell Biol.*, 174: 329-338), provides good evidence of a possible epigenetic (e.g. chromatin remodelling) role for TRIM24.

However, despite the research that has already been directed at TRIM24, its precise cellular functions are yet to be elucidated. In particular, the potential enzymatic activities of TRIM24 and its possible effects within a cell have not been fully identified.

Parallels between embryonic development and cancer have often been drawn, because in both cases the ability to proliferate and differentiate are key factors. In embryonic development, epigenetic controls, which are typically established via chemical modification of the DNA or chromatin structure, are thought to be an important factor, because they enable the transmission of information from a cell or multicellular organism to its descendants, without that information being encoded in the nucleotide sequence of genes. For example, gene expression can be moderated via the methylation and acetylation of histones that are associated with genomic DNA. Epigenetic modifications can occur at different times in the normal development of an organism and, significantly, also during transformation of normal cells into cancerous cells (Feinberg & Vogelstein, 1983, *Nature,* 301: 89-92). That said, any previous suggestion of the involvement of TRIM24 in cancer is merely speculative.

The present invention identifies a previously unknown cellular role for TRIM24, i.e. in its ability to interact with p53 and in doing so to regulate p53 stability in vivo. The invention further provides evidence of the involvement of TRIM24 in cancer; in particular, in cancers associated with the p53 tumour suppressor protein.

Interaction of TRIM24 with p53

In the present invention, tandem affinity purification (TAP) was used to identify new binding partners of p53—one of the best-established tumour suppressor genes in oncology.

First, a "knock-in" mouse expressing an epitope-tagged, endogenous p53 protein: the Tandem Affinity Purification (TAP)-tagged p53 (TAP-p53) mouse, was generated by gene targeting methodology. The wild-type mouse p53 locus contains eleven exons.

In brief, mES cells were collected and transformed with a targeting vector designed to insert a loxP-flanked PGK-neo cassette for positive selection (i.e. a construct in which expression of the neomycin gene is driven by the pgk-1 gene promoter), into the last intron of p53, and at the same time insert the TAP tag in frame into the terminal exon. As previously mentioned, the TAP-tag comprises a short peptide consisting of the Protein A and Calmodulin-Binding Protein motifs, separated by a tobacco etch virus (TEV) protease cleavage site. The neo cassette was then removed using transient cre expression in mES cells to generate the p53-TAP allele. This allele differs from the wild-type allele by the presence of a single loxP site in the terminal intron and fusion of the TAP-tag to the C-terminus of p53. mES cells containing one wild-type and the p53-TAP allele are injected into blastocysts (using standard methodology in the art) for the creation of p53-TAP knock-in mice.

In this mouse, p53 is expressed under the control of endogenous p53 promoters to advantageously yield endogenously regulated levels of p53.

In addition, the mES cells (p53TAP/+) can be used inter alia for p53 protein studies. If required, the TAP-p53 can be purified, via the TAP-tag, to isolate native, functional p53-protein complexes from effectively normal cells.

To purify p53, TAP-p53 cells were treated with doxorubicin, which acts as a stress factor and, therefore, increases the activity of p53. In this regard, induction of p53 through stress is typically achieved at the protein level, for example, by affecting the stability and/or activity of p53 (such as, through post-translational modifications), rather than at the mRNA level. Thus, following doxorubicin induction of p53, p53 mRNA levels may not be altered. Following ES cell extract preparation, tandem affinity purification was used to pull-down p53-interacting (i.e. co-purifying) proteins via the TAP-tag. Protein extracts collected were separated by SDS-PAGE and silver stained (see FIG. 3). Bands specifically present in TAP-p53 eluted fractions (lane 2) are indicated by black triangles: these protein bands were processed for mass spectrometric peptide analysis in order to identify p53 co-purifying proteins. Samples identically prepared from untreated mES cells were processed as a control (data not shown). Proteins bound to beads, which were not released by TEV treatment (Tobacco Etch Virus protease) are indicated in lane 3 (for wt p53) and lane 4 (for TAP-p53). These bands represent the proteins that are pulled down in the experiment, but which are not co-purified solely through an interaction with the TAP-p53 protein. Also indicated in FIG. 3 are the protein bands corresponding to TAP-p53 (a), p53 (b), IgG heavy and light chains (c and e, respectively) and TEV protease (d).

From this study, four proteins were isolated and identified by mass spectroscopy. Two of the identified proteins were mdm2 and p53-binding protein 1, which are known p53 interacting proteins, thus validating the system. Surprisingly, TRIM24 was identified as one of the other two p53-interacting proteins. Interestingly, no p53-interacting proteins were identified in the absence of doxorubicin, which confirmed that the effect was p53-dependent.

Hence, from this study, TRIM24 has been identified as a protein showing a close association and strong interaction with p53. This was an entirely unexpected finding as there have been no previous reports of TRIM24/p53 protein-protein interactions. In fact, as reported in Torres-Padilla & Zernicka-Goetz (2007, *J. Cell Biol.*, 174: 329-338), previous studies intended to identify cellular factors that are influenced by TRIM24 (i.e. using antisense to knock-down TRIM24 expression) have not identified or suggested the association or involvement of p53. Furthermore, it is notable that the result of the present study significantly contrasts with the previously recognised indirect interaction between TRIM28 (another TRIM family member) and p53, which occurs only via the binding of mdm2 (or in humans, hdm2) to p53.

There are a number of regions of TRIM24 that could be responsible for the binding of TRIM24 to p53. For example, TRIM24 possesses both the BROMO and PHD protein-protein interaction domains that are suitable for interacting with acetylated and methylated lysine residues, respectively, of histone proteins. It is known that p53 is a target for both acetylation and methylation and, therefore, it is likely that TRIM24 interacts with p53 at least in part through these recognised interaction motifs. Additionally, the RBCC motifs of TRIM family members are known to dictate substrate binding and specificity during function as protein modifiers (e.g. E3 ubiquitin ligases).

Moreover, in comparison with prior art studies of p53 tumour suppressor function, it is considered that the results of this study are physiologically relevant. The prior art studies have typically relied on the over-expression of p53 and/or analysis of tumour-derived cell lines under continuous culture. Such prior art systems may introduce artefacts and promote non-physiological interactions that are of little genuine significance. By contrast, the cell lines from TAP-p53 mice show normal expression levels of p53. It is thus far more likely that purification experiments will detect physiologically relevant p53-interacting proteins.

Thus, the identification of this interaction indicates a role for TRIM24 in both developmental and disease processes, especially in oncology, and provides a new target for cancer therapy, particularly, for cancers associated with p53.

It is well known that p53 is highly regulated by numerous post-translational processes including phosphorylation, acetylation, and ubiquitination-mediated degradation (Yang et al., 2004, *Oncogene*, 23: 2096-2106). In this regard, mdm2, a protein known to interact with and regulate p53, contains a RING domain that has been shown to be capable of modifying p53 by ubiquitylation and neddylation (Xirodimas et al., 2004, *Cell*, 118: 83-97). The RING motif is characteristic of E3 ligase activity. Certain E3 ligases are capable of ubiquitylation activity whilst others catalyse sumoylation. Sumoylation is similar to ubiquitylation but results in addition of a SUMO (Small Ubiquitin-related Modifier) protein to the target rather than addition of the related ubiquitin protein. E3 ligase catalytic activity is typically exhibited in the presence of associated E1 and E2 ligases, which together function as a complex to catalyse the addition of one or more ubiquitin/SUMO moieties to a specific amino acid residue in a target protein.

Notably, TRIM24 also contains a RING domain and, therefore, it is proposed that once bound to p53, TRIM24 regulates p53 activity or stability through any of a number of different chemical modifications. For example, TRIM24 may catalyse the ubiquitylation, sumoylation and/or neddylation of p53.

Accordingly, the invention also relates to methods for identifying any enzymatic activities of TRIM24 that catalyse post-translational modifications of p53. Furthermore, the invention provides methods for identifying molecules that modulate any of the enzymatic activities of TRIM24 and, thereby, molecules capable of effecting a change in activity of p53.

Involvement of TRIM24 in Cancer

Following the above-discussed experiments, the expression levels of TRIM24 were investigated in known cancer cell types.

Bioinformatics searches were used to interrogate the Gene Expression Omnibus (GEO) and the Cancer Genome Anatomy Project (CGAP). The data obtained indicates that TRIM24 is up-regulated in: (i) breast cancer cell lines compared with mammary epithelium; (ii) cell lines derived from metastatic colon cancer, compared with lines from primary colon cancer; (iii) retinal cancers compared with normal retinal cells; and (iv) androgen-sensitive prostate cancer cell lines, compared with androgen-insensitive prostate cancer cell lines. Interestingly, the opposite effect was found in renal tumours in which the expression of TRIM24 was lower than in normal kidney cells.

Accordingly, a cancer in a subject may be detected and/or diagnosed by detecting and/or quantifying expression levels of TRIM24 in a biological sample obtained from the subject. Thus, the invention relates to a method of detecting and/or diagnosing the presence of cancer in a subject, the method comprising: (i) providing a biological sample from a patient; (ii) detecting and/or quantifying the expression level of TRIM24 in the biological sample; and (iii) comparing the level of TRIM24 in the biological sample with that in a control sample; wherein an different expression level of TRIM24 in the biological sample compared to that in the control sample indicates the presence of cancer in the patient. Typically, expression of TRIM24 at a level in excess of the level in the control sample is indicative of the presence of cancer. A cancer may, for example, be detected and/or diagnosed when the expression of TRIM24 in the biological sample is at least 1.5-fold higher than in a control sample;

suitably the expression is at least 2-fold higher than in the control sample; more suitably at least 3-fold higher than in the control sample; and still more suitably the expression of TRIM24 is at least 4-fold or at least 5-fold higher than the expression levels of TRIM24 in the control sample. The control sample typically comprises corresponding non-transformed (i.e. non-cancerous) cells from a healthy individual. Suitably, the biological sample comprises cells obtained from a biological source selected from: tissues; whole blood; serum; plasma; saliva; cerebrospinal fluid; ascites fluid; pleural fluid and urine. More suitably the sample is a tissue or blood sample. The biological sample may advantageously comprise cells obtained from a biopsy of a suspected tumour. Typically, the control sample has been obtained from a healthy individual. It will be appreciated that the biological sample may be processed or treated in some way prior to detecting and/or quantifying TRIM24 expression, such that an extract of the original sample obtained from the subject is used in the method of the invention. Suitably, the method is carried out in vitro.

The expression of TRIM24 may be detected and/or quantified using any appropriate system for identifying, detecting, measuring or quantifying the expression of TRIM24. Suitably, the method is selected from one or more of detecting and/or quantifying the level of: TRIM24 polynucleotide or a portion, fragment, variant or complementary strand thereof; TRIM24 mRNA or a portion of fragment thereof; TRIM24 cDNA; TRIM24 polypeptide or a portion or fragment thereof; and TRIM24 biological activity. Suitably the method comprises detecting and/or quantifying the level of TRIM24 mRNA, TRIM24 polypeptide or TRIM24 biological activity. In some embodiments, the method involves detecting and/or quantifying the level of TRIM24 mRNA or TRIM24 polypeptide; and more suitably, the method involves detecting and/or quantifying the level of TRIM24 mRNA.

In some embodiments of the invention the expression of TRIM24 is detected and/or quantified by a method comprising contacting the biological sample, or an extract thereof, with a polynucleotide probe that is capable of hybridising under stringent hybridisation conditions to TRIM24 mRNA or a portion or fragment thereof. In further embodiments, said TRIM24 mRNA or a portion or fragment thereof comprises at least 18 contiguous bases from SEQ ID NO: 1, or the sequences shown in FIG. 1. One suitable method by which the expression of TRIM24 may be detected and/or quantified is by gene expression microarray analysis. Another suitable method of detecting and particularly for quantifying TRIM24 expression is by RT-PCR (e.g. real-time quantitative PCR).

The sequence of the TRIM24 DNA or mRNA to which a polynucleotide probe for use in accordance with the invention hybridises can conveniently be called a "target" sequence. In order to hybridise under stringent conditions, it will be appreciated that the polynucleotide probe must be substantially complementary to the target TRIM24 DNA or mRNA sequence. Most preferably, the polynucleotide probe is entirely complementary to the target sequence.

In an alternative embodiment, the expression of TRIM24 is detected and/or quantified by a method comprising contacting the biological sample or an extract thereof with an antibody or antigen binding portion thereof, that specifically recognises the TRIM24 polypeptide or a portion or fragment thereof. In a preferred embodiment, the TRIM24 polypeptide or a portion thereof comprises at least 8 consecutive amino acids from SEQ ID NO: 2.

In embodiments of the invention, the difference in expression of TRIM24 between the biological test sample and a control sample is correlated with a likelihood of cancer selected from: breast cancer, retinal cancer, prostate cancer, androgen-sensitive prostate cancer, colon cancer, acute lymphoblastic leukaemia, and renal cancer. In certain embodiments, detection of raised levels of TRIM24 expression in breast tissue is correlated with breast cancer; detection of raised levels of TRIM24 expression in retinal tissue is correlated with retinal cancer; detection of raised levels of TRIM24 expression in colon tissue is correlated with colon cancer; and detection of raised levels of TRIM24 expression in prostate tissue is correlated with prostate cancer. In another embodiment, detection of lowered levels of TRIM24 expression in kidney tissue is correlated with renal cancer.

Suitably, the detection and/or diagnosis of cancer is extended to include an in vitro diagnostic determination of cancer progression, i.e. prognosis. In such embodiments, the variation of TRIM24 expression in samples obtained from a subject (typically in neoplastic tissue taken from a patient) over a time course is monitored and any variations in expression are correlated with cancer progression. Such a method of the invention may further comprise the steps of: (i) providing a plurality of biological samples from a patient over a set time course; (ii) detecting and/or quantifying the level of TRIM24 in the plurality of biological samples; and (iii) comparing the level of TRIM24 in the plurality of biological samples with the level in one or more control samples; wherein the level of TRIM24 in the plurality of biological samples over the time course is compared to that in the one or more control samples, and is correlated to the progression of cancer in the patient. Beneficially, the subject is a mammal and suitably, a human.

The invention also relates to a method for the diagnostic determination of cancer progression in a cancer patient, the method comprising: (i) providing a plurality of biological samples from a patient over a set time course; (ii) detecting and/or quantifying the level of TRIM24 in the plurality of biological samples; and (iii) comparing the level of TRIM24 in the plurality of biological samples with the level in one or more control samples; wherein the level of TRIM24 in the plurality of biological samples over the set time course is compared to that in the one or more control samples, and is correlated to the progression of cancer in the patient. In some embodiments, an increasing difference between the levels of TRIM24 in the plurality of biological samples compared to that in the one or more control samples over the set time course is indicative of the progression of cancer in the patient. That is, where the level of TRIM24 expression increases over the time course of the test (in comparison to the control sample), there is an indication of cancer progression in the patient.

Cellular Effects of TRIM24 Expression and Activity

TRIM24 is known to be a transcriptional co-repressor or co-activator protein and, therefore, it has key cellular activities: as evidenced by its role in NR signalling pathways. Accordingly, the up- or down-regulation of TRIM24 may cause one or more significant downstream effects. To investigate possible new mechanisms of cancer initiation and progression, to aid in the discovery of new targets for cancer therapeutics, and/or to provide potential new detection or diagnostic methods, the cellular interactions and effects of TRIM24 were investigated.

Specifically, to determine whether the physical interaction between TRIM24 with p53 could have a physiologically relevant effect, and to determine the potential role of TRIM24 in p53-mediated responses to cellular stress, siRNA molecules that specifically recognise mouse TRIM24 mRNA were used to catalyse the degradation of TRIM24 mRNA and thereby effect a TRIM24 knockdown in mouse ES cells.

Four siRNA molecules having the sequences: siRNA1: 5'-AAACUGACCUGUCGAGACUUU-3' (sense strand, SEQ ID NO: 3) and 5'p-AGUCUCGACAGGUCAGU-UUUU-3' (antisense strand, SEQ ID NO: 22); siRNA2: 5'-GCAAGCGGCUGAUUACAUAUU-3' (sense strand, SEQ ID NO: 4) and 5'p-UAUGUAAUCAGCCGCU-UGCUU-3' (antisense strand, SEQ ID NO: 23); siRNA3: 5'-UAAGUUCAGUGACGACUCAUU-3' (sense strand, SEQ ID NO: 5) and 5'p-UGAGUCGUCACUGAACU-UAUU-3' (antisense strand, SEQ ID NO: 24); siRNA4: 5'-UAGAGCACGUCAUGCAUUUUU-3' (sense strand, SEQ ID NO: 6) and 5'p-AAAUGCAUGACGUGCUC-UAUU-3' (antisense strand, SEQ ID NO: 25)) were designed to specifically target the mouse TRIM24 mRNA sequence. The sense strands of the above siRNA molecules target the mouse TRIM24 mRNA sequence (LOCUS: S78221) at nucleotides; 1018-1036, 1433-1451, 3369-3387, and 1368-1387, respectively. The equivalent regions of the human TRIM24 mRNA sequence can be readily identified and these equivalent regions provide suitable sequences against which to target siRNA molecules for knock-down of human TRIM 24. As a control, an siRNA molecule pool having no known homology to eukaryotic sequences was used (Dharmacon). In particular, the control siRNA molecules are not able to target mouse TRIM24 was used.

The pool of four siRNA molecules was introduced into mES cells using standard procedures known in the art, for example, using the Lipofectamine™ 2000 system (Invitrogen) as described in the Examples. Parallel experiments were conducted for populations of mES cells in the presence or absence of doxorubicin, which is used to induce cellular stress and, hence, the expression of p53. Cell populations transformed with the pool of TRIM24-specific siRNA molecules or a control siRNA were incubated for 48 hours before doxorubicin treatment. Cell samples were then taken for analysis of gene expression at 5 hours and 12 hours after treatment with doxorubicin (or with a vehicle control), and the RNA extracted. Extracts of RNA were tested for expression levels of TRIM24, p53, p21, perp, mdm2, nanog and 18S rRNA by real-time, RT-PCR according to standard protocols known to the person skilled in the art. p21, perp, mdm2 and nanog were selected for expression measurements because the corresponding genes and protein products are thought to be influenced by p53 activity and, thus, indirectly by TRIM24. Measurements of 18S rRNA was used in each case as a control for cell count and efficiency of RNA extraction, and the expression level of each gene of interest was normalised relative to the level of 18S rRNA expression.

Figure 4:
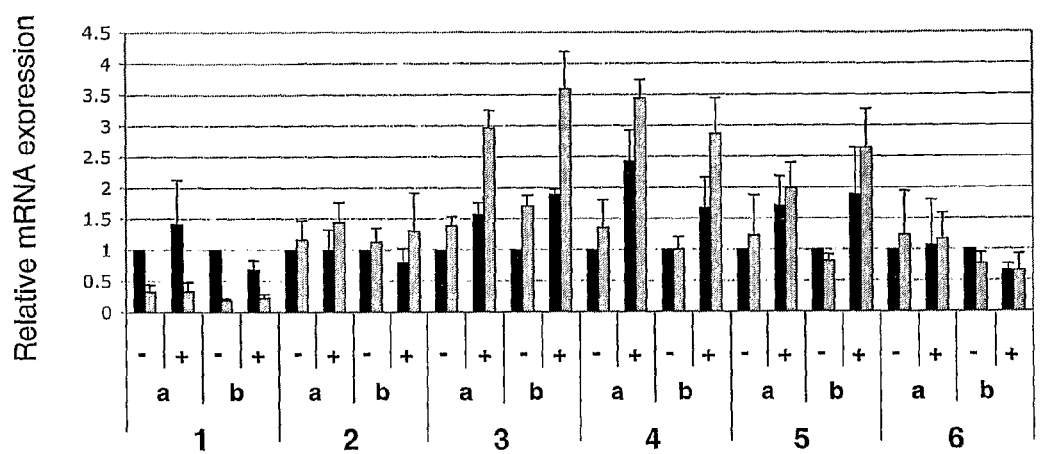
FIG. 4 is a bar chart showing the expression levels assessed by RT-PCR of selected genes in mouse embryonic stem (mES) cells. mRNA levels are indicated for: TRIM24 (1), p53 (2), p21 (3), mdm2 (4), perp (5), and nanog (6), following treatment of mES cells with a control siRNA molecule (filled bars) or a TRIM24-targeting siRNA molecule (striped bars); without (−) or with (+) exposure to doxorubicin. For each experiment, samples were analysed 5 hours (a) and 12 hours (b) after induction of p53 with doxorubicin. Expression levels are shown as normalised values relative to the expression level of 18S rRNA. Results are shown as an average of 3 or 4 separate experiments with between 3 and 5 separate RT-PCR measurements of each sample.
Figure 5:
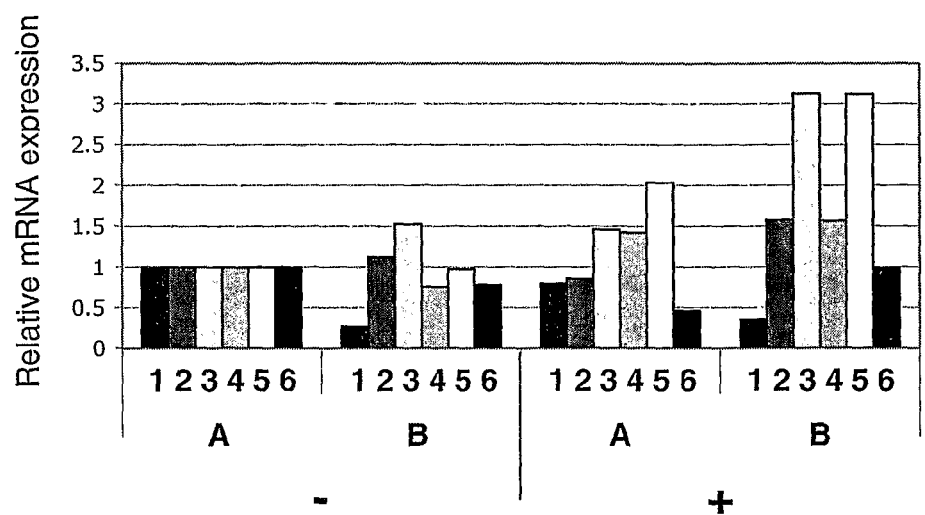
FIG. 5 is a bar chart showing the expression levels assessed by RT-PCR of selected genes in mouse embryonic stem (mES) cells. mRNA levels are indicated for: TRIM24 (1), p53 (2), p21 (3), perp (4), mdm2 (5), and nanog (6), following treatment of mES cells with a control siRNA molecule (A) or a TRIM24-targeting siRNA molecule (B); without (−) or with (+) exposure to doxorubicin. Results indicated are an average of two separate experiments.
Figure 6:
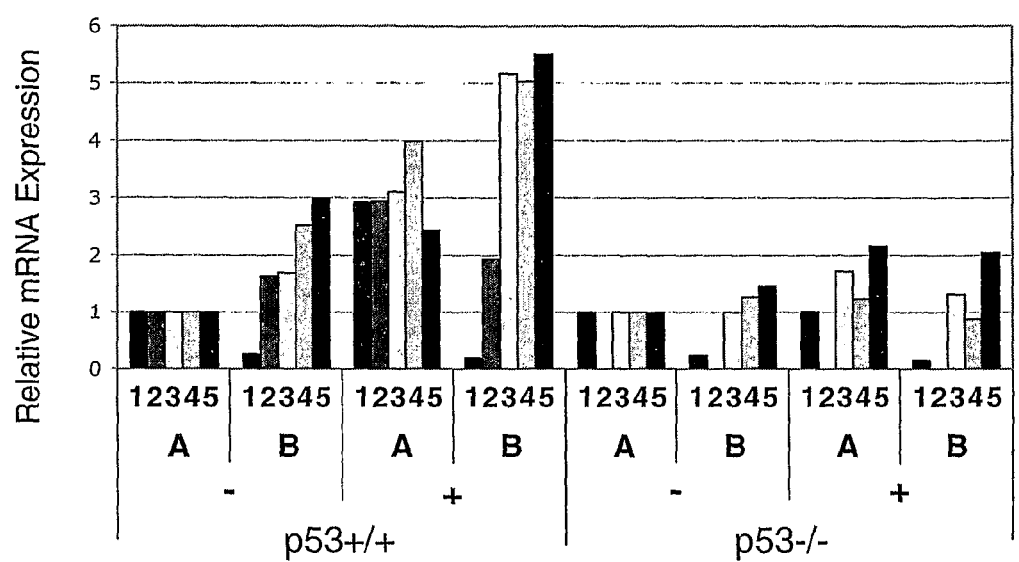
FIG. 6 is a bar chart showing the expression levels assessed by RT-PCR of selected genes in mouse embryonic fibroblast (MEF) cells. mRNA levels are indicated for: TRIM24 (1), p53 (2), p21 (3), mdm2 (4), and perp (5), following treatment of MEF cells with a control siRNA molecule (A) or a TRIM24-targeting siRNA molecule (B); without (−) or with (+) exposure to doxorubicin; for MEFs expressing p53 (p53+/+) and for MEFs that do not express p53 (p53−/−). Expression levels are shown as normalised values relative to the expression level of 18S rRNA. Results are shown as an average of 3 separate experiments with between 3 and 5 separate RT-PCR measurements of each sample.

The results of the TRIM24 knockdown experiment are displayed in FIGS. 4 to 6, which data are an average of a number of independent siRNA knockdown experiments.

In more detail, FIG. 4 shows the expression levels of the genes for TRIM24 (1), p53 (2), p21 (3), perp (4), mdm2 (5) and nanog (6) in mouse embryonic stem (mES) cells. First, it can observed that the TRIM24-specific siRNA molecule caused a significant reduction in the level of TRIM24 expression in comparison to the control siRNA molecule, which provides evidence of the efficacy of the experiment. The data further indicate that the loss of TRIM24 expression leads to a significant increase in p53-mediated activation of p21 and mdm2 gene expression in mES cells in response to doxorubicin treatment. The change in p21 expression, as a result of TRIM24 knockdown, has a p-value of 0.003 after 5 hours and 0.034 after 12 hours of treatment. For mdm2 expression, the p-values are both 0.05. By contrast, the data indicate that the expression of the nanog gene is virtually unaltered by the down-regulation of TRIM24. The effect of TRIM24 knockdown on the expression of the perp gene was moderate; indicating that the depletion of TRIM24 causes an increase in its expression.

It should also be noted that the expression level of p53 was not significantly altered by the knockdown of TRIM24. This observation is not entirely a surprise, because it is thought that TRIM24 regulates p53 activity at the post-transcriptional Level (e.g. by binding to p53 as shown herein), rather than at the level of transcription.

FIG. 5 displays the results of a similar experiment in which TRIM24 mRNA is depleted using TRIM24-specific siRNA in mES cells.

As in the above-described experiment, the expression levels of TRIM24 (1), p53 (2), p21 (3), perp (4), mdm2 (5), and nanog (6) mRNA are indicated following treatment of mES cells with a control siRNA molecule (A) or a TRIM24-targeting siRNA molecule (B); with (+) or without (−) exposure to doxorubicin. In agreement with the above data, it can be seen that the depletion of TRIM24 results in an increase in the p53-regulated activation of gene expression. In particular, it can be seen that the expression of p21 and mdm2 are significantly increased on knockdown of TRIM24 and in the presence of doxorubicin; and nanog gene expression, which is repressed when p53 is activated by doxorubicin, is derepressed to control levels when TRIM24 is depleted. In slight contrast to the previous results, perp expression is relatively unaltered in the presence or absence of TRIM24-specific siRNA in this study.

FIG. 6 shows the results of a similar experiment to that displayed in FIGS. 4 and 5, except that the studies were carried out in mouse embryonic fibroblast (MEF) cells. In this case, however, the expression of nanog was not analysed, and the experiments were conducted in parallel in MEF cells that were either positive (p53+/+) or negative (p53−/−) for p53 expression. As in the data presented in FIG. 4, it is apparent that the expression level of p53 (2) is not significantly affected by the TRIM24 knockdown; although, it is clear that p53 expression is induced by doxorubicin. Most notably, it is readily apparent from the data for the p53+/+ cells, that the expression levels of the p53 responsive genes p21 (3), mdm2 (4) and perp (5) are significantly up-regulated on depletion of TRIM24. The relative lack of any increase in expression of these same genes in the p53−/− cells clearly demonstrates the p53-dependence of p21, mdm2 and perp gene activation.

Thus, these data also further support a model in which TRIM24 is a negative regulator of p53 at the protein level.

By way of explanation, the genomewide mapping of oct4 and nanog interactions with chromatin in both mouse and human ES cells suggests that these proteins, which are considered to be stem cell factors that are required for pluripotency, bind to the TRIM24 gene itself (Loh et al., 2006, *Nature Genetics,* 38: 431-440).

Further, recent evidence has suggested that p53 may play a vital role in maintaining stem cells in a self-renewing, pluripotent state. In this regard, it has been shown that the stem cell factor nanog is directly repressed by p53 (as previously mentioned), a mechanism that typically is held in stasis in the absence of differentiation- or stress-signalling (Lin, et al., 2005, *Nature Cell Biol.,* 7: 165-171; Qin et al., 2007, *J. Biol. Chem.* 282: 5842-5852). It is thought that ubiquitous co-repressors, acting directly on nanog chromatin structure, are targeted to that region by the interaction of p53 with the nanog gene. Since nanog appears to be an essential factor in stem cell maintenance, p53-mediated regulation of nanog expression may be intercalated with differentiation and response to stress-signaling so as to avoid propagation of damaged DNA, particularly in a population of stem cells. The present identification of TRIM24 as a regulator of p53 function thus offers potential insights into the surveillance of genomic stability in stem cells, and the control of stem cell maintenance. This, in turn, has implications for TRIM24 as an oncology target, especially with respect to cancer stem cells.

These results are particularly significant because p53 can be considered to be a canonical tumour suppressor gene for which alterations in expression and/or mutations have been detected in over 50% of human cancers. Further, it should be noted that not all cancers are deficient in p53 (many show aberrant expression of p53) and, therefore, the surprising identification of TRIM24 as a negative regulator of p53 provides enormous potential for new cancer therapeutic interventions that target TRIM24. In this regard, recently reported studies have now demonstrated that expression of p53 can cause regression of cancer. For example, in a study by Xue et al. (2007, Nature, 445(7128): 656-660) it was demonstrated that senescence and tumour clearance can be triggered by p53 restoration in murine liver carcinomas. Similarly, Ventura et al., (2007), Nature, 445(7128): 661-665 showed that the restoration of p53 function leads to tumour regression in vivo in mouse models of human cancers.

Without being bound by theory, a number of mechanisms by which TRIM24 could negatively regulate p53 activity can be envisaged. First, the data provided herein appears to suggest that the regulation of p53 by TRIM24 is likely to be mediated via a direct protein-protein interaction, rather than through gene regulation, by way of example. In one model a simple non-enzymatic protein-protein interaction between TRIM24 and p53 may be sufficient to inhibit p53 activity. In addition, or in the alternative, the TRIM24-mediating inhibition of p53 may be via an enzymatic modification of p53. There are at least two mechanisms (and possibly up to four) by which an enzymatic modification of p53 may be achieved by TRIM24. For instance, it has been previously reported that TRIM24 can act as a protein kinase (Fraser et al., 1998, *J. Biol. Chem.*, 273: 16199-16204). In addition, TRIM24 is known to contain a RING domain, which has been predicted (although not yet demonstrated) to possess E3-like ubiquitin ligase activity, which may catalyse ubiquitylation and possibly also sumoylation or neddylation of a target polypeptide.

In this regard, it is well established that both phosphorylation and ubiquitination are important post-translational modifications of p53 and, more recently, it has been shown that p53 may also be regulated by neddylation (Xirodimas et al., 2004, *Cell*, 118: 83-97). Whether TRIM24 is capable of modifying p53 by phosphorylation, ubiquitylation, sumoylation and/or neddylation can be tested experimentally using standard procedures for measuring such activities. For example, kinase and/or ubiquitinase activity can be measured in vitro and/or in vivo.

The presence of BROMO and PHD domains within TRIM24 also suggests that TRIM24 could interact with p53 through acetylated or methylated lysine residues (through the BROMO and/or PHD interaction motifs, respectively). Again, routine experiments known to the person skilled in the art can be used to determine whether the TRIM24—p53 interaction is mediated by acetylation and/or methylation: see for example, Jacobson et al., (2000), *Science*, 288(5470): 1422-1425 for methodology in relation to BROMO domain binding; and Martin et al., (2006), *Mol. Cell. Biol.*, 26(21): 7871-7879 for methodology in relation to interactions through PHD domains.

Once any TRIM24-mediated p53 post-translational modifications have been identified, it is envisaged that a high-throughput assay can be used to identify small molecule inhibitors of the appropriate TRIM24 activity. Any small-molecule inhibitors of the appropriate activity that are identified may be used as therapeutic agents in the treatment of p53-associated cancers (or cancer models); or may be used to study p53 and TRIM24 signalling pathways.

Detection of TRIM24 Polypeptides

The present invention also relates to methods for detecting and/or diagnosing the presence of cancer in a subject, comprising detecting and/or quantifying the expression of TRIM24 in a biological sample obtained from said subject. The means of detection and/or quantification may involve detecting and/or quantifying a TRIM24 polypeptide or a portion or fragment thereof.

Thus, the TRIM24 polypeptide may be a full-length TRIM24 polypeptide, or may comprise or consist of a fragment of at least 6 consecutive amino acids of TRIM24. Suitably, the TRIM24 polypeptide or fragment thereof is derived from SEQ ID NO: 2 (see also FIG. 2). More suitably, the fragment or portion comprises or consists of at least 8, at least 10, at least 12, or at least 15 consecutive amino acids from SEQ ID NO: 2. Still more suitably, the fragment or portion of TRIM24 polypeptide comprises or consists of 16 consecutive amino acids of SEQ ID NO: 2. In general, the C-terminal sequence of TRIM24 is beneficially used for the selection of TRIM24-specific antibodies, because this region appears to be less conserved between TRIM family members. For example, a known C-terminal sequence of human TRIM24 (NP_003843) for the generation of TRIM24 antibodies is: KRLKSIEERQLLK.

In some cases, it may be necessary to detect or quantify a variant or derivative of the TRIM24 polypeptide or fragment or portion thereof. In such cases, the variant or derivative suitably has a sequence that is at least 50%, 60%, 70%, 80% or 90% identical to SEQ ID NO: 2 or the portions or fragments described herein. Mouse and human TRIM24 are approximately 93% identical over the full-length of their sequences. Beneficially, therefore, a variant or derivative of human TRIM24 has a sequence that is at least 93%, at least 95%, at least 98% or at least 99% identical to SEQ ID NO: 2 or the portions or fragments described herein. By TRIM24, it is meant the short or long isoform (as previously discussed), and therefore, the invention encompasses variants or derivatives of the short and/or the long isoforms of TRIM24 (indicated in FIG. 2) having the above-mentioned sequence identity.

One aspect of the invention relates to a method of detecting and/or diagnosing cancer cells in a biological sample. In one embodiment, TRIM24 polypeptides, fragments or portions thereof, in either native or denatured form, can be detected and/or quantified using an antibody or antigen-binding portion thereof. Preferably, the antibody or antigen-binding portion thereof is bound to a label effective to permit detection of the TRIM24 polypeptide, polypeptide fragment or portion; or a cell containing or displaying the polypeptide, polypeptide fragment or portion. Thus, on binding of the antibody or antigen-binding portion to the cancer cell, polypeptide or fragment, the binding event can be detected.

For example, the biological sample obtained from the subject or patient is contacted with the antibody or antigen-binding portion thereof having an appropriate label (e.g. a fluorescent label or radioactive marker), under conditions effective to permit binding of the antibody or antigen-binding portion thereof to the polypeptide, polypeptide fragment, or a cell containing or displaying the polypeptide or fragment thereof, in the biological sample. The presence of the TRIM24 polypeptide or fragment thereof in the sample can then be detected by detection of the label.

Thus, the method of the invention can be used to screen patients for various cancer types advantageously using the same antibody or antigen-binding portion thereof. In this regard, means for enabling an antibody to cross a cell membrane and enter a cell are now known to the person skilled in the art.

It will be appreciated that the method of the invention may also be used to screen subjects in vivo by administering, for example, by parenteral injection, an antibody or antigen binding portion thereof, which is preferably labelled. However, advantageously the method is carried out in vitro, for example, on a biological sample previously obtained from a subject.

Advantageously, the antibody, or antigen-binding portion thereof, is specific to TRIM24. Polyclonal antibodies specific for TRIM24 can be prepared according to standard techniques that are known to the person skilled in the art. Thus, in accordance with the invention a polyclonal antibody that selectively binds to a TRIM24 epitope (for example, a 16 amino acid region of TRIM24), may be raised against an oligopeptide derived from human or mouse TRIM24. Alternatively, monoclonal antibodies to TRIM24 polypeptides, or epitope fragments thereof, may be prepared, for example, according to the methods described by Galfre & Milstein, 1981, *Methods Enzymol.*, 73(Pt B): 3-46. Most suitably, the epitope is derived from human TRIM24 or the antibody is derived against human TRIM24.

In another aspect, the invention also relates to the TRIM24-binding or TRIM24-activity-modifying molecules per se, such as monoclonal antibodies, polyclonal antibodies and the antigen-binding portions thereof.

Monoclonal antibodies may be produced by techniques which are well known in the art, e.g. as described in Kohler & Milstein (1975, *Nature*, 256: 495). Briefly, immune cells (lymphocytes) are obtained from the spleen of a mammal (e.g. a mouse), which has been previously immunised with the antigen of interest either in vivo or in vitro. The antibody-secreting lymphocytes are then fused with (mouse) myeloma cells or transformed cells, which are able to replicate indefinitely in cell culture, to produce an immortal, immunoglobulin-secreting cell line. The resulting fused cells (i.e. hybridomas), are then cultured, and the resulting colonies are screened for the production of the desired monoclonal antibodies. Colonies producing suitable antibodies are cloned and grown, typically in vitro, to produce a monoclonal antibody.

Mammalian lymphocytes are immunised by in vivo immunisation of the animal (e.g. a mouse) with an antigen, e.g. a TRIM24 polypeptide or fragment thereof (as described herein). Immunisations are repeated, as necessary, at intervals of up to a few weeks, to obtain a sufficient titre of antibodies. Following the last antigen injection, the animals are sacrificed and spleen cells removed. Fusion with mammalian myeloma cells, for example, is effected by standard and well-known techniques, e.g. using polyethylene glycol (PEG) or other fusing agents, as described in Milstein & Kohler (1976, *Eur. J. Immunol.*, 6: 511).

Typically, the immortal cell line produced is murine, but may alternatively be derived from cells of other mammalian species, including rats and humans, as known to the person of skill in the art.

Polyclonal antibodies can also be raised using techniques well known in the art. In brief, antigen (as above) is administering subcutaneously to rabbits, for example, which have first been bled to obtain pre-immune serum. The injected material may contain an adjuvant to increase the immune response, for example, a pulverised acrylamide gel containing the antigen may be administered. Rabbits are bled two weeks after the first injection the same antigen is administered three times every six weeks to increase the antibody response. A sample of serum is collected 10 days after each antigen boost, and polyclonal antibodies can be recovered from the serum by affinity chromatography using the corresponding antigen (see e.g. Harlow et al., eds, *Antibodies: A Laboratory Manual*, 1988).

In addition to whole antibodies, the methods of the invention also encompass antigen-binding portions or fragments of such antibodies. Such antigen-binding portions include Fab fragments, F(ab')2 fragments, and Fv fragments, which can be made using conventional procedures, such as proteolytic fragmentation (Goding, 1983, *Monoclonal Antibodies: Principles and Practice*, N.Y. Academic Press, pp 98-118).

TRIM24 levels of expression can be determined in samples taken from solid tumours present in an individual. Typically, such samples are obtained by biopsy of a suspected or known tumour. In certain instances it is advantageous to also take a biopsy of normal (i.e. non-neoplastic) tissue from a site close to that of the tumour so that TRIM24 levels in the sample of tumour tissue can be compared and normalised for that individual. It will be appreciated that across a population there will be polymorphic variations in gene expression and that the inclusion of an internal control in the diagnostic method of the invention represents a valuable optional feature.

The invention also encompasses biological agents, such as antibodies or antigen-binding portions thereof, which are suitable for either killing or ablating cancerous cells. In such cases, the antibody or antigen-binding portion thereof may be conjugated to a secondary moiety to affect the killing of the targeted cancer cells. Suitable mechanisms for killing of a target cell containing a specific antigen for an antibody of the invention, for example, by inducing apoptosis, are known to the person skilled in the art. By way of example, Tse & Rabbitts (2000, *Proc. Natl. Acad. Sci. USA*, 97(22): 2266-12271) describe intracellular antibody-caspase fusion protein-mediated cell killing, induced specifically by the antibody in the presence of its specific antigen.

Detection of TRIM24 Polynucleotides

Expression levels of TRIM24 polynucleotides (e.g. mRNA) can be determined via a number of techniques commonly known to the person of skill in the art. For example, TRIM24 expression can be determined by looking at the level of TRIM24 mRNA in cells.

Total RNA can be extracted from cells in a sample using standard single step RNA extraction procedures (for example, Chomczynski & Sacchi, 1987, *Anal. Biochem.*, 162: 156). Total RNA extraction reagents such as TRIzol® reagent are also suitable (Invitrogen, Life Technologies, Inc.).

Suitable methods for detection of TRIM24 mRNA in a sample from which RNA has been extracted, include but are not limited to: RT-PCR, RNase protection assay, and northern blot assay (Sambrook et al., *Molecular Cloning: a Laboratory Manual*, Cold Spring Harbor Press, Cold Spring Harbor, N.Y.). In addition, the probes may advantageously be immobilised on a substrate so as to form part of an array or microarray, that allows screening of the sample for many different biomarkers in addition to expression of TRIM24.

According to the present invention, homology to the nucleic acid sequences of TRIM24 is not limited simply to sequence identity. Many nucleic acid sequences can demonstrate biologically significant homology to each other despite having apparently low sequence identity. In the present invention homologous nucleic acid sequences are considered to be those that will hybridise to each other under conditions of low stringency, but are advantageously, those that will hybridise to each other under conditions or high stringency (Sambrook et al., supra). By way of example, for nucleic acid molecules over about 500 bp, stringent hybridisation conditions may include a solution comprising about 1 M Na$^+$ at 25° to 30° C. below the melting point, Tm (e.g., 5×SSPE, 0.5% SDS, at 65° C.; see also Ausubel at al., 1995, *Current Protocols in Molecular Biology*, Greene Publishing).

Suitably, the methods of the invention encompass polynucleotide variants and fragments that hybridise to a TRIM24 cDNA, mRNA or fragments thereof under stringent hybridisation conditions. Most advantageously, the polynucleotide variants and fragments are specific to TRIM24.

Thus, a polynucleotide for use in a method of the invention may comprise or consist of the entire unique cDNA nucleic acid sequence of TRIM24 (SEQ ID NO: 1), or may comprise or consist or a fragment thereof. Suitably, where the polynucleotide is a fragment of the sequence of SEQ ID NO: 1, for example, a probe, it may comprise or consist of at least 12 consecutive bases of SEQ ID NO: 1, or at least 15, at least 18, at least 20, at least 30, or at least 50 consecutive bases. In some embodiments the fragment or probe may advantageously comprise or consist of at least 100, at least 150, at least 200, at least 300, or at least 500 consecutive bases of SEQ ID NO: 1. For example, the sequences to which the siRNA molecules disclosed herein anneal to TRIM24 mRNA are particularly useful sequences against which probes may be targeted for use in the methods and systems of the invention.

Treatment of Cancer

The present invention also relates to methods and compositions for the treatment of cancer. Reagents for the inhibition of TRIM24 expression and/or biological activity include, but are not limited to, antisense nucleic acid molecules, siRNA (or shRNA), ribozymes, small molecules, and antibodies or the antigen binding portions thereof. For a review of nucleic acid-based technologies see, for example, Kurreck, J. (2003) "Antisense technologies—Improvement through novel chemical modifications", *Eur. J. Biochem.* 270: 1628-1644. The reagents for inhibition of TRIM24 may affect TRIM24 expression and/or biological activity indirectly; for example, by acting on a factor that affects TRIM24 gene expression or that modifies or inhibits TRIM24 biological activity. Advantageously, the reagent for use as an inhibitor of TRIM24 acts directly on TRIM24, to affect TRIM24 gene expression at the mRNA level (e.g. transcription or mRNA stability), or the protein level (e.g. translation or biological activity).

(1) Antisense nucleic acid sequences are complementary to and will hybridise with TRIM24 mRNA in-vivo. Antisense nucleic acid sequences may be in the form of single stranded DNA or RNA molecules that hybridise to all or a part of the sequence of TRIM24 mRNA (corresponding cDNA shown in FIG. 1, SEQ ID NO: 1). Typically, an antisense molecule is at least 12 nucleotides in length and at least 90%, 93%, 95%, 98%, 99% or 100% complementary to the chosen target nucleotide sequence. Antisense oligonucleotides can be of any reasonable length, such as 12, 15, 18, 20, 30, 40, 50, 100, 200 or more nucleotides, having the advantageous above-mentioned complementarity to its corresponding target nucleotide sequence.

An antisense oligonucleotide may contain modified nucleotides (or nucleotide derivatives), for example, nucleotides that resemble the natural nucleotides, A, C, G, T and U, but which are chemically modified. Chemical modifications can be beneficial, for example, in: providing improved resistance to degradation by endogenous exo- and/or endonucleases, to increase the half-life of an oligonucleotide in vivo; enhancing the delivery of an oligonucleotide to a target cell or membrane; or increasing the bioavailability of a oligonucleotide.

Typically, an antisense molecule contains a mixture of modified and natural nucleotides, and in particular, the 5' most and/or the 3' most nucleotides (e.g. the two outermost nucleotides at each end of the strand) may be modified to increase the half-life of the antisense molecule in vivo. In addition, or in the alternative, the backbone of an antisense molecule may be chemically modified, e.g. to increase resistance to degradation by nucleases. A typical backbone modification is the change of one or more phosphodiester bonds to a phosphorothioate bonds. An antisense molecule may suitably also comprise a 5' cap structure and/or a poly-A 3' tail, which act to increase the half-life of the antisense molecule in the presence of nucleases.

Antisense oligonucleotides can be used to inhibit expression of TRIM24 in target tissues and cells in vivo, or such molecules may be used in an ex vivo treatment, or in an in vitro diagnostic test.

Requirements for the design and synthesis of antisense molecules against a specific target gene (via its corresponding RNA sequence), methods for introducing and expressing antisense molecules in a cell, and suitable means for modifying such antisense molecules are known to the person of skill in the art.

For example, antisense molecules for use in therapy may be administered to a patient directly at the site of a tumour (for example, by injection into the cell mass of the tumour), or they can be transcribed from a vector that is transfected into the tumour cells. Transfection of tumour cells with gene therapy vectors can be achieved, for example, using suitable liposomal delivery systems or viral vectors (Hughes, 2004, *Surg. Oncol.,* 85(1): 28-35).

(2) Another means of specifically down-regulating a target gene, such as the TRIM24 gene is to use RNA interference (RNAi). Naturally, RNAi is typically initiated by long double-stranded RNA molecules, which are processed by the Dicer enzyme into 21 to 23 nucleotides long dsRNAs having two-nucleotide overhangs at the 5' and 3' ends. The resultant short dsRNA molecules are known as small interfering RNAs (siRNAs). These short dsRNA molecules are then thought to be incorporated into the RNA-induced silencing complex (RISC), a protein-RNA complex, which acts as a guide for an endogenous nuclease to degrade the target RNA.

It has been shown that short (e.g. 19 to 23 bp) dsRNA molecules (siRNAs) can initiate RNAi, and that such molecules allow for the selective inactivation of gene function in vivo, for example, as described in Elbashir et al. (2001, *Nature,* 411: 494-498). Thus, this technique provides a means for the effective and specific targeting and degradation of TRIM24 mRNA in cells in vivo (as demonstrated herein, see e.g. FIG. 4). Accordingly, the invention provides siRNA molecules and their use to specifically reduce or eliminate the expression of TRIM24 in tumour cells.

Suitable double-stranded siRNA molecules can be formed from two substantially complementary oligonucleotide strands, a sense (non-targeting) strand and an antisense (targeting) strand, which anneal to form a double-stranded region of any suitable length. The double stranded region may be between 17 and 29 nucleotides, suitably between 18 and 25 nucleotides, more suitably between 19 and 23 nucleotides, and most suitably between 19 and 21 nucleotides. Alternatively, an siRNA molecule can be generated from a short hairpin (or fold-back stem-loop structure) within a single RNA molecule (i.e. an shRNA molecule), which may give rise to siRNA following intracellular processing. Such an approach can be advantageous for RNAi therapy because it requires the synthesis of a single RNA molecule only, it may allow a less complex/time-consuming annealing process, and the resultant molecule may be more stable than its double-stranded counterpart.

Advantageously, the double-stranded (complementary) region of the siRNA or shRNA molecule contains no mismatches in the region of complementarity. However, one or two mismatches are usually tolerated. Suitably, where there are mismatches, those mismatches are in the non-targeting (sense) strand of the siRNA molecule (or non-targeting/sense portion of an shRNA molecule). Mismatches may also be tolerated at the ends of the RNA strands (as described below).

The two strands of an siRNA molecule (or the two complementary regions of an shRNA molecule) may anneal with no overhangs at either the 3' or 5' end of the strand(s). However, 3' or 5' overhangs of at least 1 nucleotide may be present. Typically, the overhang is at one or both 3' ends of the respective strands. A 1-, 2-, or 3-nucleotide 3' overhang is suitable, and advantageously there is a 2-nucleotide 3' overhang on each strand. It should be noted that where there is an overhang, the overhanging nucleotides, particularly those on the targeting strand, need not be complementary to the target sequence. Thus, the overhanging nucleotides are beneficially selected to enhance the properties of the siRNA molecule (for example, resistance to nucleases), and for ease of manufacture. Generally, an siRNA molecule has a two-nucleotide dTdT or UU 3' overhang.

In the case of an shRNA molecule for use in accordance with the invention, the loop separating the two complementary regions (or portions) may be between 3 and 23 nucleotides in length. Typically, the loop is less than 10 nucleotides, and more suitably it is less than 7 nucleotides.

As in the case of antisense and ribozyme technology, an siRNA or shRNA molecule for in vivo use advantageously contains one or more chemically modified nucleotides and/or one or more modified backbone linkages.

Advantageously, an siRNA molecule for use in accordance with the invention is targeted to a unique sequence of the TRIM24 mRNA strand, as shown in, for example, FIG. 1 for human TRIM24. Similarly, mouse TRIM24 can advantageously be targeted for RNAi using one or more of the siRNA molecules (siRNA1 to 4) given in the Examples. A suitable sequence length for targeting with an siRNA molecule may comprise approximately 17 to 23 consecutive nucleotides, suitably 19 to 23 nucleotides, and more suitably between 19 and 21 consecutive nucleotides of SEQ ID NO: 1.

Suitably, the antisense strand of the siRNA molecule, or the antisense portion of the shRNA molecule is substantially complementary to the target nucleotide sequence. By "substantially complementary" it is meant that the sequences are sufficiently complementary that the antisense strand of the resultant siRNA molecule can anneal to the target sequence sufficiently effectively to cause degradation of the target mRNA in vivo. More suitably, there are less than three mismatches in the region of complementarity, beneficially there is only 2 or 1 mismatch. Most advantageously, there are no mismatches in the complementarity between the antisense strand or portion of the siRNA or shRNA molecule and the target sequence. However, where there are overhanging nucleotides, these need not be complementary with the target sequence.

It is within the ability of the person of skill in the art, using known sequence databases to determine a suitable sequence of TRIM24 for targeting by siRNA. In a particularly advantageous embodiment the target sequence chosen is unique in an animal genome, and most suitably it is unique in the human genome.

It is possible to purchase siRNA or shRNA molecules that target particular sequences or genes. Commercially available shRNA molecules that target TRIM24 are: TRCN0000021259, TRCN0000021260, TRCN0000021261, TRCN0000021262 and TRCN0000021263 (Sigma-Aldrich, Dorset, UK).

TRCN0000021259 (Clone ID: NM_003852.2-1128s1c1; Accession Number(s): NM_003852.3, NM_015905.2; Region: CDS; TRIM24 isoform) has the sequence: 5'-CCGG CGCATGAAACTTATGCAACAACTCGAGTTGTTGCAT AAGTTTCATGCGTTTTT-3'. This molecule targets the TRIM24 CDS, and the sequence underlined (above) corresponds to nucleotides 1230-1251 in the cDNA sequence of TRIM24 shown in FIG. 1 (indicated in bold).

TRCN0000021260 (Clone ID: NM_003852.2-2762s1c1; Accession Number(s): NM_003852.3, NM_015905.2; Region: CDS; TRIM24 isoform) has the sequence: 5'-CCG GCCATGAAATGAGCCTGGCTTTCTCGAGAAAGCCA GGCTCATTTCATGGTTTTT-3'. This molecule targets the TRIM24 CDS, and the sequence underlined (above) corresponds to nucleotides 2965-2986 in the cDNA sequence of TRIM24 shown in FIG. 1 (also indicated in bold).

TRCN0000021261 (Clone ID: NM_003852.2-2217s1c1; Accession Number(s): NM_003852.3, NM_015905.2; Region: CDS; TRIM24 isoform) has the sequence: 5'-CCGG CCTGTTGTTATAGTGAAGCAACTCGAGTTGCTTCAC TATAACAACAGGTTTTT-3'. This molecule targets the TRIM24 CDS, and the sequence underlined (above) corresponds to nucleotides 2421-2441 in the cDNA sequence of TRIM24 shown in FIG. 1 (also indicated in bold).

TRCN0000021262 (Clone ID: NM_003852.2-1222s1c1; Accession Number(s): NM_003852.3, NM_015905.2; Region: CDS; TRIM24 isoform) has the sequence: 5'-CCG GGCAGCAGTACAGCATTACTTTCTCGAGAAAGTAAT GCTGTACTGCTGCTTTTT-3'. This molecule targets the TRIM24 CDS, and the sequence underlined (above) corresponds to nucleotides 1323-1344 in the cDNA sequence of TRIM24 shown in FIG. 1 (also indicated in bold).

TRCN0000021263 (Clone ID: NM_003852.2-2622s1c1; Accession Number(s): NM_003852.3, NM_015905.2; Region: CDS; TRIM24 isoform) has the sequence: 5'-CCGG CGAGACTTATCTAAACCAGAACTCGAGTTCTGGTTT AGATAAGTCTCGTTTTT-3'. This molecule targets the TRIM24 CDS, and the sequence underlined (above) corresponds to nucleotides 2826-2846 in the cDNA sequence of TRIM24 shown in FIG. 1 (also indicated in bold).

Suitable sequences of TRIM24 mRNA for targeting with siRNA or shRNA molecules according to the present invention include at least 19 consecutive bases selected from the sequences: CGCATGAAACTTATGCAACAAC, GCCATGAAATGAGCCTGGCTTT, CCTGTTGTTATAGTGAAGCAA, GGCAGCAGTACAGCATTACTTT and CGAGACTTATCTAAACCAGAA.

The invention encompasses TRCN0000021259, TRCN0000021260, TRCN0000021261, TRCN0000021262 and TRCN0000021263 for use in medicine; and advantageously for use in down-regulating TRIM24 expression for the treatment of cancer in an animal, most suitably in a human. The invention further encompasses the use of shRNA molecules TRCN0000021259, TRCN0000021260, TRCN0000021261, TRCN0000021262 and TRCN0000021263 for modulating p53-signalling pathways. Furthermore, the invention encompasses siRNA and shRNA molecules that target at least 19 consecutive bases selected from the sequences: CGCATGAAACTTATGCAACAAC, GCCATGAAATGAGCCTGGCTTT, CCTGTTGTTATAGTGAAGCAA, GGCAGCAGTACAGCATTACTTT and CGAGACTTATCTAAACCAGAA for use in medicine, and suitably for down-regulating TRIM24 expression for the treatment of cancer in an animal, more suitably, a human. Methods of using the above siRNA and shRNA molecules for the treatment of cancer are also included.

By way of example, beneficial siRNA molecules for use in accordance with the invention may comprise:
(a) 5'-CGCATGAAACTTATGCAACAAC-3' (sense strand) and
  5'-GTTGTTGCATAAGTTTCATGCG-3' (antisense strand);
(b) 5'-GCCATGAAATGAGCCTGGCTTT-3' (sense strand) and
  5'-AAAGCCAGGCTCATTTCATGGC-3' (antisense strand);
(c) 5'-CCTGTTGTTATAGTGAAGCAA-3' (sense strand) and
  5'-TTGCTTCACTATAACAACAGG-3' (antisense strand);
(d) 5'-GGCAGCAGTACAGCATTACTTT-3' (sense strand) and
  5'-AAAGTAATGCTGTACTGCTGCC-3' (antisense strand);
(e) 5'-CGAGACTTATCTAAACCAGAA-3' (sense strand) and
  5'-TTCTGGTTTAGATAAGTCTCG-3' (antisense strand).

Alternatively, siRNA molecules for use in the methods and treatments of the invention may comprise 19, 20 or 21 consecutive nucleotides from any of the sequences shown in (a) to (e) above.

Suitable siRNA molecules for targeting mouse TRIM24 may be selected from: siRNA1: 5'-AAACUGACCUGUCGAGACUUU-3' (sense strand) and 5'p-AGUCUCGACAGGUCAGUUUUU-3' (antisense strand); siRNA2: 5'-GCAAGCGGCUGAUUACAUAUU-3' (sense strand) and 5'p-UAUGUAAUCAGCCGCUUGCUU-3' (antisense strand); siRNA3: 5'-UAAGUUCAGUGACGACUCAUU-3' (sense strand) and 5'p-UGAGUCGUCACUGAACUUAUU-3' (antisense strand); siRNA4: 5'-UAGAGCACGUCAUGCAUUUUU-3' (sense strand) and 5'p-AAAUGCAUGACGUGCUCUAUU-3' (antisense strand).

In each of the above siRNA molecules, there may advantageously be included a two-base 3' overhang of dTdT or UU, by way of example. Likewise, the above siRNA molecules may comprise one or more modification to the nucleic acid or backbone bonds, as previously described.

(3) Inhibitors of TRIM24 biological activity and/or function can include antibodies (as described above), small molecules, polysaccharides and glycoproteins. Inhibitors of TRIM24 biological activity and/or function may act via a number of mechanisms such as by binding directly to the TRIM24 protein, or inhibiting a regulatory pathway that controls TRIM24 and thereby leads to suppression of TRIM24 function.

Antibodies and fragments that specifically bind to TRIM24 polypeptides may be used to treat cancers. The invention includes the use of antibodies and antibody fragments that are fused to other moieties that can have a cytotoxic effect on cancer cells. Preparation of anti-TRIM24 antibodies is described above.

Furthermore, there is also the possibility of inhibiting TRIM24 activity by expressing (at high levels) a dominant negative form of TRIM24, i.e. a modified TRIM24 that lacks the ability to regulate p53, but could interfere with endogenous TRIM24 in, for example, cancer cells. Beneficially, such a dominant negative form of TRIM24 would retain the ability to bind to p53 but would not be able to chemically modify it, for example by ubiquitylation; and so it would not be able to promote the degradation of p53.

(4) It is also possible to knock-down endogenous gene expression using artificial transcription factors, such as poly-zinc finger peptides, which are engineered to bind to a specific genomic sequence in the target cell (Isalan & Choo, 2001, *Methods Enzymol.*, 340: 593-609; and Beerli et al., 1998, *Proc. Natl. Acad. Sci. USA.*, 95: 14628-33). Typically, an artificial poly-zinc finger protein is engineered to specifically recognise a sequence upstream of the target gene, and will have a transcriptional regulatory domain (e.g. a repression domain, such as the KRAB repression domain; or an activation domain, such as VP64), appended to it in order to alter the expression of the target gene. Suitably, such an artificial transcription factor for use in accordance with the invention targets genomic sequences upstream of the TRIM24 gene, advantageously in the known 5' promoter sequences; and includes a transcriptional repression domain (e.g. KRAB) to down-regulate TRIM24 expression. Optionally, therefore, the expression of TRIM24 in a target cell, i.e. a cancer cell, may be repressed using an engineered artificial transcription factor, such as a poly-zinc finger protein (e.g. having six-zinc finger), as described, for example, in Reynolds at al., (2003), *Proc. Natl. Acad. Sci. USA.*, 100(4): 1615-20, and Papworth et al., (2003), *Proc. Natl. Acad. Sci. USA.*, 100(4): 1621-6.

Pharmaceutical preparations of the invention are formulated to conform to regulatory standards and can be administered orally, intravenously, topically, or via other standard routes. The pharmaceutical preparations may be in the form of tablets, pills, lotions, gels, liquids, powders, suppositories, suspensions, liposomes, microparticles or other suitable formulations known in the art.

Thus, the invention encompasses the use of each of the above-identified siRNA and shRNA molecules in the manufacture of a medicament for treating cancer. Suitably, the cancer is selected from: breast cancer, retinal cancer, prostate cancer, androgen-sensitive prostate cancer, colon cancer, acute lymphoblastic leukaemia, and renal cancer.

Drug Discovery

TRIM24 proteins (polypeptides or fragments thereof) can be recombinantly expressed individually or in combination to create transgenic cell lines and purified proteins for use in drug screening. Cell lines over-expressing TRIM24 or fragments thereof can be used, for example, in high-throughput screening methodologies against libraries of compounds (e.g. "small molecules"), antibodies or other biological agents. These screening assays may suitably be either cell-based assays, in which defined phenotypic changes are identified (analogous to calcium signalling in GPCR FLIPR screening), or can serve as the source of high levels of purified proteins for use in affinity-based screens such as radioligand binding and fluorescence polarisation. Suitable fragments of TRIM24 for use in drug discovery screening may include, for example, the RING domain, the BROMO domain, and/or the PHD finger domain of TRIM24 (see for example, Le Douarin et al., 1996, *EMBO J.*, 15: 6701-6715).

Small molecules and/or antibodies (or the antigen-binding portions thereof), which are identified as exerting an effect on TRIM24 (or a suitable fragment of TRIM24), for example, inhibition of an enzymatic activity of TRIM24, such as a ubiquitylation or sumoylation activity, may be suitable for use as a therapeutic agent. By way of example, a small molecule capable of inhibiting the E3 ubiquitin ligase activity of TRIM24 may be useful as an agent for inhibiting the regulation of p53 by TRIM24. Therapeutic agents may be formulated for delivery in any suitable method known to the person skilled in the art.

Manipulation of the expression (decrease or increase) of TRIM24 in cellular systems can be used to identify dependent genes that may be suitable downstream drug discovery targets, as discussed hereinbefore. Elucidation of the signal transduction pathways that interact with, control, or are controlled by TRIM24 (for example, the above-described pathways involving the interaction of TRIM24 with p53), will enable the adoption of a more "systems-biology" based approach to drug discovery.

(i) Screen for Inhibition of an Enzymatic Activity of TRIM24

First, an assay is designed in which the isolated TRIM24 (or TRIM24 fragment) demonstrates an enzymatic activity. It is proposed, in view of the data given herein and the sequence elements of TRIM24, that p53 activity may be regulated (e.g. repressed) by ubiquitylation via the E3 ubiquitin ligase activity of the RING domain of TRIM24. Assays for E3 ligase activity, and particularly with respect to proteins of the TRIM family, are known to the person skilled in the art (Vichi et al., 2005, Proc. Natl. Acad. Sci. USA, 102(6): 1945-1950). Such assays can be modified to assay the ubiquitination activity of TRIM24 or a fragment thereof.

For example, full-length TRIM24 or a fragment thereof, which contains a domain postulated to possess an enzymatic activity (such as the RING domain) can be expressed, purified and isolated by any means known to the person skilled in the art. By way of example, full-length TRIM24 may be expressed in bacteria from a bacterial expression vector, for example, as a GST-fusion protein to allow purification of the expression product, and finally to obtain isolated TRIM24. TRIM24 or a fragment thereof may alternatively be expressed in any other convenient system, such as expression in insect cells using a baculovirus expression vector.

Ubiquitylation/sumoylation activity may be dependent on the presence of a substrate, ubiquitin, an E1 ubiquitin-activating enzyme, an E2 ubiquitin-conjugating enzyme and an E3 ubiquitin ligase enzyme. Thus, an E3 ubiquitin ligase assay may be constructed in vitro by combining the purified TRIM24 (or fragment) with mammalian E1, and E2 enzyme, ATP, ubiquitin/SUMO and a protein substrate, as described in Vichi et al. (above).

The reaction mixture is incubated under suitable conditions of pH, temperature and time (e.g. pH7.4, 30° C./60 mins) to allow ubiquitylation of the substrate, before the reaction is stopped and the products of the reaction are analysed. For example, the products of the reaction may be separated by SDS-polyacrylamide gel, transferred to a nitrocellulose membrane, probed with antibodies specific for ubiquitin and/or stained to visualise protein bands. Alternatively, products of the reaction could be analysed by mass spectrometry (e.g. MALDI-TOF mass spectrometry).

The substrate for the E3 ubiquitin ligase activity of TRIM24 may be the E2 ubiquitin-conjugating enzyme itself, and/or TRIM24 may ubiquitylate/sumoylate itself—i.e. auto-ubiquitylation/sumoylation. However, the E3 ubiquitin ligase activity of some RING domain-containing proteins can be substrate specific. Thus, it may be advantageous to carry out a number of similar assays using different E2 ubiquitin-conjugating enzymes or additional substrates (e.g. free GST). Beneficially, p53 (or a p53-tagged protein) is used as a substrate for ubiquitylation/sumoylation. In this way, the ability of TRIM24 to modify p53 can be confirmed, and moreover, an assay for potentially therapeutic (small-molecule) regulators of this activity can be developed, as described below.

Next, a screen for identifying small-molecule inhibitors of the E3 ubiquitin/SUMO ligase activity of TRIM24 is conducted. Advantageously, the screen is designed to detect small-molecules that inhibit the E3 ligase activity of TRIM24 in an assay in which p53 is ubiquitylated/sumoylated. However, to identify a modulator (e.g. an inhibitor) of TRIM24 it is not necessary for the presence of p53 in the assay.

For example, a multi-well (e.g. 96-well or 384-well format) E3 ligase activity assay screen can be set up, wherein each well contains a small-molecule (drug), in addition to TRIM24 (or a fragment thereof), and the further reactants necessary for E3 ligase activity directed at p53 as the target, for example. The products of the reactions are then analysed, as described above (or using alternative methods of analysis suitable for high-throughput screening), to detect molecules that inhibit the ubiquitylation/sumoylation of p53. Advantageously, the screen is automated for high-throughput screening of small molecules.

Any molecule, including a small molecule drug, a polyamine, an aptamer, antibody (or fragment thereof), or nucleic acid (e.g. an siRNA molecule) that is identified as affecting a catalytic activity of TRIM24, irrespective of the presence of p53, is thus identified as a modulator of TRIM24. Beneficially, the modulator of TRIM24 affects the E3 ligase activity of TRIM24.

(ii) Screen for Modulator of TRIM24 Regulation of p53

It is proposed herein that TRIM24 represses the activity of p53 by binding to p53 and/or by chemically modifying p53; for example, by ubiquitylation or sumoylation, as discussed above. FIGS. 4 to 6 (already described) demonstrate that one consequence of the inhibition of TRIM24 (i.e. by knockdown of TRIM24 RNA using RNAi technology) is the up-regulation of p53 responsive genes such as p21, perp and mdm2. Thus, RNAi molecules specific for TRIM24 can be considered to be a small-molecule modulator of TRIM24 regulation of p53; and RNAi molecules specific for TRIM24 can likewise be considered to be a modulator of p53 activity (as demonstrated by the up-regulation of p53-responsive genes). Thus, one aspect of the invention is directed to modulators (advantageously small-molecules) of TRIM24 activity, and advantageously of p53 activity. Such modulators may be used, beneficially, to treat cancer in an animal (such as a human), and particularly to treat cancers associated with an up-regulation of TRIM24 activity, and/or cancers associated with a down-regulation of p53 activity. Since as many as 50% of known cancers exhibit aberrant p53 activity, the small molecules identified according to the present invention should provide considerable utility for the treatment of cancer.

To identify additional small-molecule modulators of p53 activity, an assay is designed to identify molecules that up-regulate p53-responsive genes in the presence of p53 and TRIM24 (or a fragment thereof). Advantageously, such modulators may up-regulate p53 activity by inhibiting the repression of p53 by TRIM24.

To create such an assay, it is first necessary to design an expression vector in which a reporter construct is expressed under the control of a p53-responsive promoter.

p53-responsive reporter constructs are known to the skilled person in the art (see for example, Thornborrow & Manfredi, 1999, J. Biol. Chem., 274(47): 33747-33756; Miyashita & Reed, 1995, Cell, 80: 293-299; Datto et al., 1995, J. Biol. Chem., 270: 28623-28628). Such a reporter construct can be produced by inserting a p53-responsive promoter in front of a suitable reporter gene. A p53-responsive promoter can be obtained, for example, by cloning the promoter sequences (or at least the minimal promoter sequences) from known p53-responsive genes, such as the 5' promoter regions of p21, perp, mdm2, bax, or maspin; or by artificially synthesising a p53-responsive promoter by inserting the known p53-response element upstream of a suitable reporter gene.

A p53-response element has been previously described (Thornborrow & Manfredi, supra; el-Deiry et al., 1992, *Nat. Genet.*, 1: 45-49; Funk at al., 1992, *Mol. Cell. Biol.* 12: 2866-2871; Halazonetis et al., 1993, *EMBO J.,* 12: 1021-1028), and comprises two palindromic decamers of 5'-RRRCW-WGYYY-3' (SEQ ID NO: 26) (where R is a purine, Y is a pyrimidine, and W is adenine or thymine) separated by 0-13 bp; forming 4 repeats of the pentamer 5'-RRRCW-3', which alternate between the top and bottom strands of the duplex DNA.

A suitable reporter gene can be any gene that it conveniently expressed in eukaryotic cells and can be readily detected, such as CAT, LacZ, luciferase, or GFP (including any one of the many GFP-like derivatives). An advantageous reporter gene is luciferase. Suitably, the luciferase (or other reporter) is expressed under the control of p53-responsive elements or under the control of, for example, the p21 5' promoter sequence described in Datto et al., supra.

p53 can be expressed in a eukaryotic cell using a p53 expression vector; for example, a vector containing a gene encoding p53, which is under the control of a suitable eukaryotic promoter, such as the cytomegalovirus (CMV) promoter. Suitable p53 expression vectors are known to the person skilled in the art and, advantageously, allow the expression of wild-type human p53 in a eukaryotic cell (Thornborrow & Manfredi, supra; Baker et al., 1990, *Science,* 249: 912-915; Srivastava et al., 1993, *Oncogene,* 8: 2449-2456).

Advantageously, TRIM24 is also expressed in the appropriate eukaryotic cell from the above p53 expression vector, or from a separate expression vector. Such a vector should contain a gene encoding TRIM24 under the transcriptional control of eukaryotic promoter, for example, the CMV promoter already mentioned. Where an expression vector is under the control of an element such as CMV, it may also be necessary to provide the CMV RNA polymerase enzyme, e.g. in another or the same vector.

Beneficially, the expression constructs also contain selection markers to allow the selection of cells containing each of the relevant constructs. Suitable selection markers and systems for the selection of transformed/transfected cells are well known to the skilled person in the art.

The assay for a modulator of p53 activity may be carried out using methods that will be understood by the skilled person in the art. Briefly, by way of example, a p21-promoter luciferase reporter construct may be co-transfected with the p53 expression vector into eukaryotic cells. A suitable eukaryotic cell may be a Jurkat cell. After e.g. 48 hours, the cells may be harvested and analysed for reporter expression, for example, for luciferase activity measured using a Luminometer. This gives the expression level of the reporter construct driven by p53 alone. In a parallel experiment, the cells may be co-transfected with the reporter construct and with expression vector(s) for expressing p53 and TRIM24. The luciferase activity detected in these cells is indicative of the effect of TRIM24 on the activity of p53, and in view of the results described in more detail elsewhere herein, would be expected to be lower than in the absence of TRIM24.

To detect modulators of the TRIM24 regulation of p53 (and hence, modulators of p53 activity), the above tests may be carried out in the presence of (libraries of) small molecules and then identifying (populations of) cells that express more or less reporter (luciferase) than in the presence of TRIM24 and p53 alone. By carrying out (automated) high-throughput screening of candidate small molecules, for example, from small molecule libraries, modulators that either up- or down-regulate the TRIM24-p53 interaction may be identified. Advantageously, small molecules that up-regulate the expression of the p53-responsive reporter construct in the presence of TRIM24 and p53 are isolated in this way. Such molecules can be considered to modulate the effect of TRIM24 on p53 and, beneficially, to inhibit the effect of TRIM24 on p53. These molecules are candidate therapeutic drugs for use in treating cancers, and more suitably, cancers associated with the up-regulation of TRIM24.

Thus, in another aspect, the invention is directed to methods for the detection/identification/isolation of small molecule modulators of p53 activity (via TRIM24), which method comprises determining whether the modulator interacts with and affects the ability of TRIM24 to regulate p53. Advantageously, the method is directed to identifying a modulator of TRIM24 and p53, which up-regulates p53 activity; for example, as demonstrated by the increase in expression of a reporter gene that is under the influence of a p53-responsive promoter.

The invention is also directed to compositions, for example, pharmaceutical compositions comprising such modulators of p53 and their use in treating cancer in an individual (e.g. a human), suitably, for treating a cancer associated with up-regulation of TRIM24.

Modulators of TRIM24 and p53 include the p53 RNAi molecules described elsewhere herein.

Kits

In accordance with the present invention, any of the polynucleotides, antibodies or antigen-binding portions thereof may be included in a kit for use in detecting and/or diagnosing cancer in a subject. In addition, a kit may be provided for treating cancer in a patient in need thereof, in which case, the kit may in addition or alternatively, comprise a therapeutic drug/agent as described herein. Further, a kit may be provided for the manipulation of p53 signalling pathways, in which case, the kit may in addition or alternatively, comprise a small molecule or agent as described herein, which inhibits the activity or expression of TRIM24, or which inhibits the interaction (binding) of TRIM24 with p53.

Typically, such kits comprise: (i) either one or more polynucleotides (as described herein), which are capable of specifically recognising TRIM24 cDNA, mRNA and/or polynucleotide fragments of TRIM24 cDNA or mRNA; and/or (ii) one or more antibodies or antigen-binding portions thereof, which are capable of specifically recognising TRIM24 polypeptides.

In some embodiments, the one or more polynucleotides, antibodies or antigen-binding portions thereof that are capable of specifically recognising TRIM24 polypeptides, polynucleotides or fragments thereof are labelled (or otherwise modified) to allow detection and/or quantification of the amount of TRIM24 polynucleotide or polypeptide detected. Suitable labels for conjugating to polynucleotides or polypeptides (e.g. antibodies) are known to the person of skill in the art, and include fluorescent labels.

Thus, the invention relates to a diagnostic kit for detecting and/or diagnosing cancer in a sample of tissue obtained from a subject, comprising at least one TRIM24 binding molecule capable of binding specifically to a TRIM24 polypeptide or mRNA, in a manner that enables the expression level of TRIM24 in the sample to be determined. In one embodiment, the TRIM24 binding molecule in the diagnostic kit comprises at least one polynucleotide probe capable of hybridising under stringent hybridisation conditions to at least 18 contiguous bases from SEQ ID NO: 1. In some embodiments the polynucleotide probe is immobilised on a substrate, for example, as part of a microarray.

Alternatively, the TRIM24 binding molecule in the diagnostic kit for detecting and/or diagnosing cancer in a subject, comprises at least one antibody or antigen binding portion thereof capable of specifically recognising a TRIM24 polypeptide or a portion or fragment thereof. Advantageously, the antibody or antigen binding portion thereof is capable of specifically recognising at least 8 consecutive amino acids from SEQ ID NO: 2.

The kits of the invention may advantageously also include instructions for use of the kit.

The invention is further described in the following non-limiting example.

EXAMPLE

Experimental

Materials and Methods

The practice of the present invention will employ, unless otherwise indicated, conventional techniques of chemistry, molecular biology, microbiology, recombinant DNA and immunology, which are within the capabilities of a person of ordinary skill in the art. In addition, such techniques are explained in the literature, for example: J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, & A. Kahn, 1996, *DNA Isolation and Sequencing: Essential Techniques*, John Wiley & Sons; J. M. Polak & James O'D. McGee, 1990, *In Situ Hybridization: Principles and Practice*; Oxford University Press; M. J. Gait (Editor), 1984, *Oligonucleotide Synthesis: A Practical Approach*, Irl Press; and D. M. J. Lilley & J. E. Dahlberg, 1992, *Methods of Enzymology*: DNA Structure Part A: Synthesis and Physical Analysis of DNA Methods in Enzymology, Academic Press.

TAP-p53 Transgenic Mouse Generation

A transgenic mouse can be generated using procedures known in the art, as described, for example, in *Manipulating the Mouse Embryo: A Laboratory Manual*, by Andras Nagy (Editor), Marina Gertsenstein (Editor), Kristina Vintersten (Editor), Richard Behringer (Editor), Cold Spring Harbor Laboratory Press; 3rd edition (Dec. 15, 2002); and *Gene Targeting: A Practical Approach* by Alexandra L. Joyner (Editor), Oxford University Press, USA; 2nd edition (Feb. 15, 2000).

The wild-type mouse p53 locus contains eleven exons. The targeting vector was designed to insert a loxP-flanked PGK-neo cassette into the last intron of p53 and at the same time insert the TAP tag in frame into the terminal exon. The neo cassette was then removed using transient cre expression in ES cells to generate the p53-TAP allele. This allele differs from the wild-type allele by the presence of a single loxP site in the terminal intron and fusion of the TAP-tag to the C-terminus of p53. ES cells containing one wild-type and the p53-TAP allele were used for blastocyst injection and creation of p53-TAP knock-in mice. The mES cells ($p53^{TAP/+}$) are used further for TAP-p53 purification studies.

SDS-PAGE and Silver Staining

Protein extracts were prepared in the manner described by Dignam et al., (1983) *Nucleic Acids Res.*, 11:1475-89, and 10 µg of protein lysate was separated on 7.5% polyacrylamide gels. Proteins were separated by denaturing gel electrophoresis (Laemmli U. K., 1970, *Nature*, 227:680-5), and visualized by silver stain (Morrissey, J. H., 1981, *Anal. Biochem.* 117: 307-310).

Mass Spectrophotometry

The identities of the proteins of interest were confirmed by mass spectrophotometry, which was carried out according to standard procedures in the art (Jung et al., 2005, *Mol. Endocrinol.*, 19(10): 2451-2465).

This study led to the identification of four proteins that displayed a close association with p53. Two of these proteins, mdm2 and p53-binding protein 1, are already known to be p53-interacting proteins, thus validating the system. Another protein identified as a p53-interacting protein was TRIM24 (human sequence of TRIM24 given in SEQ ID NO: 2). Interestingly, however, no p53-interacting proteins were identified in the absence of doxorubicin, which confirmed that the result was p53-dependent.

Accordingly, TRIM24 has been identified as a protein showing a close association and a strong interaction with p53.

RNAi Transfection

Four double-stranded siRNA molecules against mouse TRIM24 RNA were manufactured (Dharmacon RNA Technologies, Chicago, Ill., USA), with the following nucleotide sequences:

siRNA1: 5'-AAACUGACCUGUCGAGACUUU-3' (sense strand; SEQ ID NO: 3) and
5'p-AGUCUCGACAGGUCAGUUUUU-3' (antisense strand; SEQ ID NO: 22);
siRNA2: 5'-GCAAGCGGCUGAUUACAUAUU-3' (sense strand; SEQ ID NO: 4) and
5'p-UAUGUAAUCAGCCGCUUGCUU-3' (antisense strand; SEQ ID NO: 23);
siRNA3: 5'-UAAGUUCAGUGACGACUCAUU-3' (sense strand; SEQ ID NO: 5) and
5'p-UGAGUCGUCACUGAACUUAUU-3' (antisense strand; SEQ ID NO: 24);
siRNA4: 5'-UAGAGCACGUCAUGCAUUUUU-3' (sense strand; SEQ ID NO: 6) and
5'p-AAAUGCAUGACGUGCUCUAUU-3' (antisense strand; SEQ ID NO: 25);

To perform RNA knock-down of TRIM24 mRNA, the pool of four siRNA molecules (above) was transfected into mES cells using the Lipofectamine™ 2000 reagent system (Invitrogen) according to the manufacturers instructions. Briefly 1 µl of lipofectamine 2000 is used per 20 pmols of siRNA to be transfected, to give a final concentration of 100 nM siRNA. $1.5 \times 10^5$ mES cells were transfected with the pool of siRNA molecules. Cells were then incubated for 48 hours at 37° C. prior to treatment with doxorubicin (0.5 µg/ml), or with vehicle only as a negative control.

Cell samples were taken for analysis at 5 hours and 12 hours following treatment with doxorubicin or with a (negative) vehicle control.

Parallel experiments were also conducted in which a control siRNA molecule (i.e. one that does not target TRIM24) was used.

RNA Isolation, Reverse Transcription PCR (RT-PCR) and Real-Time PCR

Total RNA was isolated using Trizol® reagent (Invitrogen) and treated with DNase1 (Invitrogen) according to the manufacturer's instructions. RNA was quantified spectrophotometrically (NanoDrop). 500 ng of total RNA was reverse transcribed using random hexamers (AB Gene) and 1 µl of Superscript™ (Invitrogen) according to manufacturers' instructions. 3 µl (7.5 ng cDNA) of the reaction mixture (diluted to 200 µl) was used in subsequent PCRs. All PCRs were carried out on an Applied Biosystems 7500 Fast machine incorporating Sybrgreen PCR Master Mix (Applied Biosystems) according to standard protocols (see also Chao et al., 2003, *J. Biol. Chem.*, 278: 41028-41033).

Cycles for real-time PCRs were as follow: 95° C./10 min, 1 cycle; 95° C./30 sec, 55° C./30 sec, 72° C./45 sec, 40 cycles; for all genes analysed with the exception of perp. In the case of perp a temperature of 60° C. was substituted for 55° C. in the above described PCR protocol.

The primers sequences used to detect and quantify mouse TRIM24, p53, p21, mdm2, perp, nanog and 18S rRNA are indicated below:

```
TRIM24
(forward primer)
5'-GCAAGCGGCTGATTACATACA-3'         (SEQ ID NO: 45)

(reverse primer)
5'-TGGTCACAGGAGAAGCATCAC-3'         (SEQ ID NO: 46)

p53
(forward primer)
5'-ACATGACGGAGGTCGTGAGA-3'          (SEQ ID NO: 47)

(reverse primer)
5'-TTTCCTTCCACCCGGATAAG-3'          (SEQ ID NO: 48)

p21
(forward primer)
5'-TCTCAGGGCCGAAAACG-3'             (SEQ ID NO: 49)

(reverse primer)
5'-CGCTTGGAGTGATAGAAATCTG-3'        (SEQ ID NO: 50)

mdm2
(forward primer)
5'-ATTGCCTGGATCAGGATTCAGTT-3'       (SEQ ID NO: 51)

(reverse primer)
5'-ACCTCATGATCCTCATCTGAGA-3'        (SEQ ID NO: 52)

perp
(forward primer)
5'-TCATCCTGTGCATCTGCTTC-3'          (SEQ ID NO: 53)

(reverse primer)
5'-GGGTTATCGTGAAGCCTGAA-3'          (SEQ ID NO: 54)

nanog
(forward primer)
5'-TCCAGCAGATGCAAGAACTC-3'          (SEQ ID NO: 55)

(reverse primer)
5'-GTGCTGAGCCCTTCTGAATC-3'          (SEQ ID NO: 56)

18S rRNA
(forward primer)
5'-TCAAGAACGAAAGTCGGAGGTT-3'        (SEQ ID NO: 57)

(reverse primer)
5'-GGACATCTAAGGGCATCACAG-3'         (SEQ ID NO: 58)
```

The average threshold (Ct) was determined for each gene and normalized with respect to 18S rRNA levels. Similar experiments to that described above were conducted in mouse embryonic fibroblast (MEF) cells. The results of the real time-PCR experiments are displayed in FIGS. 4 to 6 and are described in detail above.

In brief, the data demonstrates that the expression of p53 responsive genes in both mES and MEF cells was significantly increased as a result of TRIM24 knock-down. These results, therefore, indicate that TRIM24 exhibits a negative regulatory activity on p53. Genes which showed particularly strong p53-dependent expression were p21, mdm2 and perp in MEF cells; and p21 and mdm2 in mES cells (FIGS. 4 to 6). The fact that this effect was p53 dependent was demonstrated by the data in FIG. 6, wherein in the absence of p53, the above genes are not up-regulated. Notably, the down-regulation of TRIM24 did not have a significant effect on the expression of p53 itself, which is consistent with a model in which TRIM24 modulates p53 at the protein level and not at the RNA level.

Finally, the experiments demonstrate the efficacy of targeting TRIM24 to modulate the activity of p53, and in particular of using RNAi to modulate the activity of p53 (via a down-regulation of TRIM24).

The data further suggests the applicability of down-regulating TRIM24 expression or activity to de-repress the activity of p53, for example, to treat cancer; particularly to treat cancers associated with p53 activity.

Antibody Generation

Affinity-purified rabbit polyclonal antibodies were prepared against the TRIM24 polypeptide sequence (SEQ ID NO: 2) using standard procedures, such as described above. A suitable region of the TRIM24 polypeptide against which to target an antibody is the C-terminal region. Most suitably, the epitope sequence selected is a sequence present in TRIM24 but absent from all or most other TIF1 proteins.

Expression in Breast Cancer Cells

MCF7 (p53-positive breast cancer) cells were transfected with a FLAG-tagged TRIM24 expression construct and incubated +/− doxorubicin (which induces p53 protein through a DNA damage response pathway). Briefly, nanogramme quantities of Flag-Trim24 plasmid were transfected per well of a 6-well plate containing MCF7 cells. 24 hrs post-transfection, cells were treated with Doxorubicin (0.5 μg/ml) for 24 hrs. Cells were then harvested and protein lysates were immunoblotted as indicated.

Figure 7:
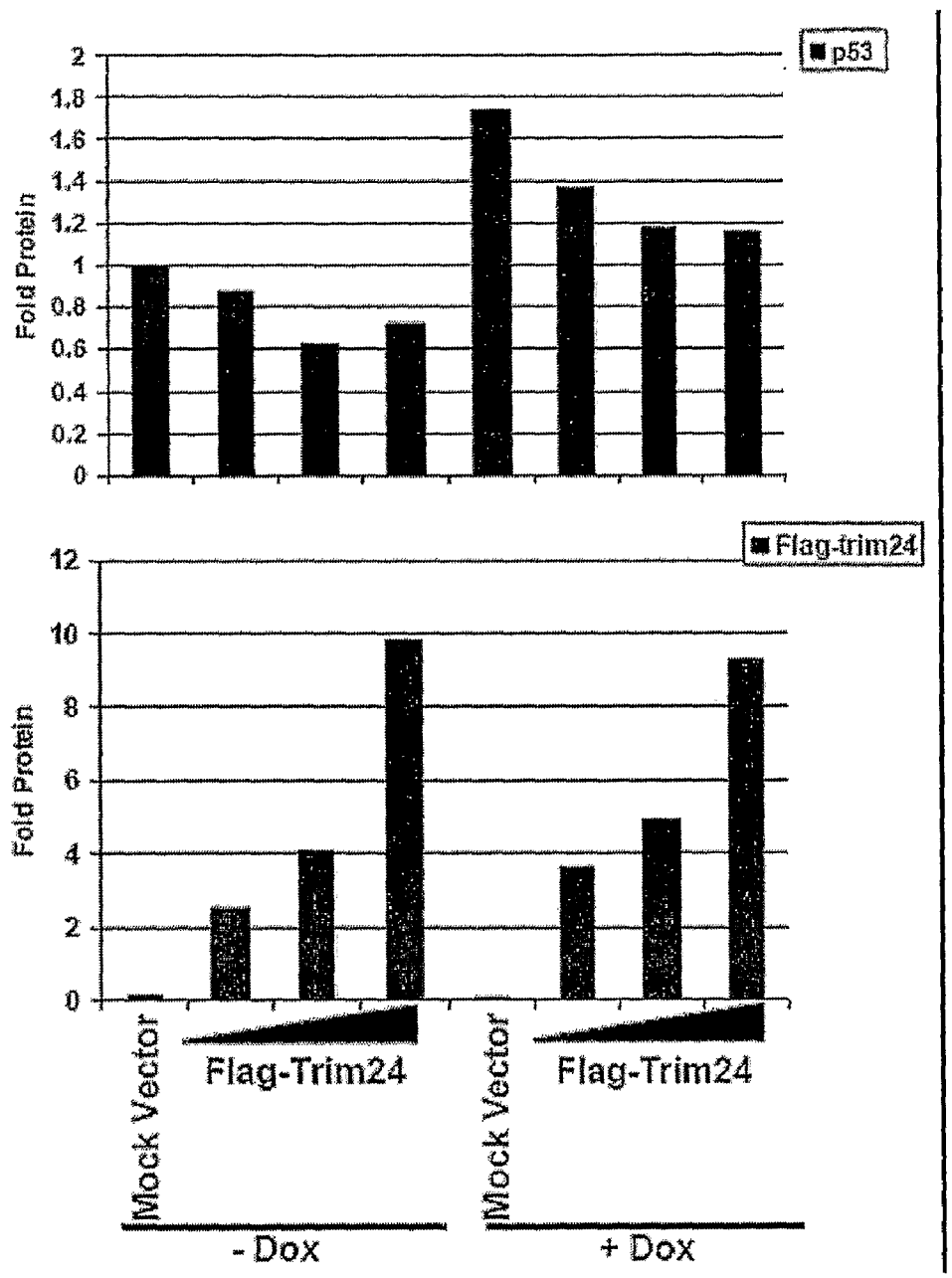
FIG. 7 shows a graphical representation of the levels of p53 and TRIM24 protein assessed by western blotting when MCF7 (p53-positive breast cancer) cells were transfected with a FLAG-tagged TRIM24 expression construct and incubated +/− doxorubicin (which induces p53 protein through a DNA damage response pathway).

Levels of p53 and TRIM24 protein were assessed by western blotting and the results represented graphically in FIG. 7. These demonstrate that in cells transfected with an empty/mock expression vector, doxorubicin treatment leads to p53 protein up-regulation, as expected. The extent of this up-regulation diminishes with increasing levels of TRIM24 protein (with a plateau). This is consistent with a negative regulatory effect of TRIM24 on p53 protein levels.

Figure 8:
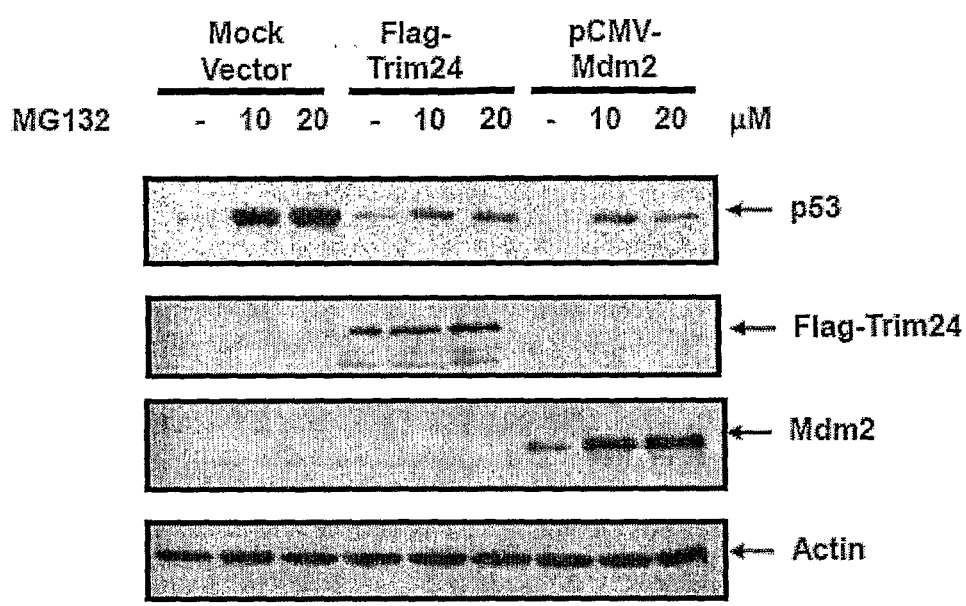
FIG. 8 is a photograph of a Western Blot in which MCF7 cells were transfected with empty vector, or plasmids expressing hMdm2 or Flag-Trim24. In cells transfected with the control vector, MG132 led to a substantial increase in the level of p53 protein.

MCF7 cells were transfected with empty vector, or plasmids expressing hMdm2 or Flag-Trim24 (500 ng) per well of a 6-well plate. 24 hrs post-transfection, cells were treated with MG132 (10 and 20 μM) for 8 hrs. Cells were then harvested and protein lysates were immunoblotted as indicated. In cells transfected with the control vector, MG132 led to a substantial increase in the level of p53 protein as assessed by western blotting (see FIG. 8). In contrast, over-expression of either TRIM24 or MDM2 protein attenuated much of this increase in p53 levels. This is consistent with these proteins exerting a negatively regulatory effect on p53 protein levels, possibly through proteasome-independent mechanisms or by processes that are not inhibited by MG132 (velcade).

siRNA Knock Down of TRIM24 in Human Cancer Cell Lines

The Clustal 2.0.5 program was used to generate multiple sequence alignments of the human TRIM24 protein coding transcripts available in the public domain. siRNA sequences were designed which were expected to be in common to all isoforms/variants of TRIM24 and they are marked in FIG. 9. Underlined sequences represent sirna target. A * refers to sequence which is the same for all transcripts. A − refers to a gap inserted by CLUSTAL during the alignment process. Numbers at the end of the sequence refer to base pairs.

The siRNA target sequences described in FIG. 9 were used to design the siRNA sequences, shown in the table in FIG. 10.

The effects of TRIM24 knockdown were assessed in HCT116, PC3, A549, MCF7 and T47D cancer cell lines transfected singly with the siRNA sequences described in FIG. 10. On day 1 cells were automatically seeded into Greiner microclear collagen coated 384 well plates or Fortitude 384 well plates (HCT116) at the following densities: HCT116: 1500 or 2000 cells/well; PC3: 1000 or 1500 cells/well; A549: 1000 or 1500 cells/well; MCF7: 1500 or 2000 cells/well; T47D: 3500 or 4000 cells/well.

On day 2 siRNA transfections were performed at 30 nM using 0.076 microlitres of Dharmafect2 per well and up to 7 siRNAs targeting TRIM24 from Ambion/AB Silencer and Silencer Select Library.

On day 4 cells were observed and prepared for readouts. For quantitative real-time RT-PCR (qRT-PCR) cells were lysed and frozen, and RNA extracted using the standard protocol from Invitek (Invisisorb 96-well plate kit). Subsequently qRT-PCR was performed using standard reagents and methodologies from Applied Biosystems, using the Sybrgreen intercalation detection method. Briefly, the reverse transcription reaction was performed using ABI's High Capacity cDNA reagents with random hexamers. The qPCR step was performed using Quantace qPCR mastermix in an 11 microlitre volume containing 500 nM of sequence-specific primers. The reaction was run on an ABI 7900HT system and relative down-regulation of positive target mRNAs was calculated against 18S rRNA "house-keeper" amplification levels, comparing treated samples to samples transfected with a negative i.e. non-specific siRNA.

Figure 11:
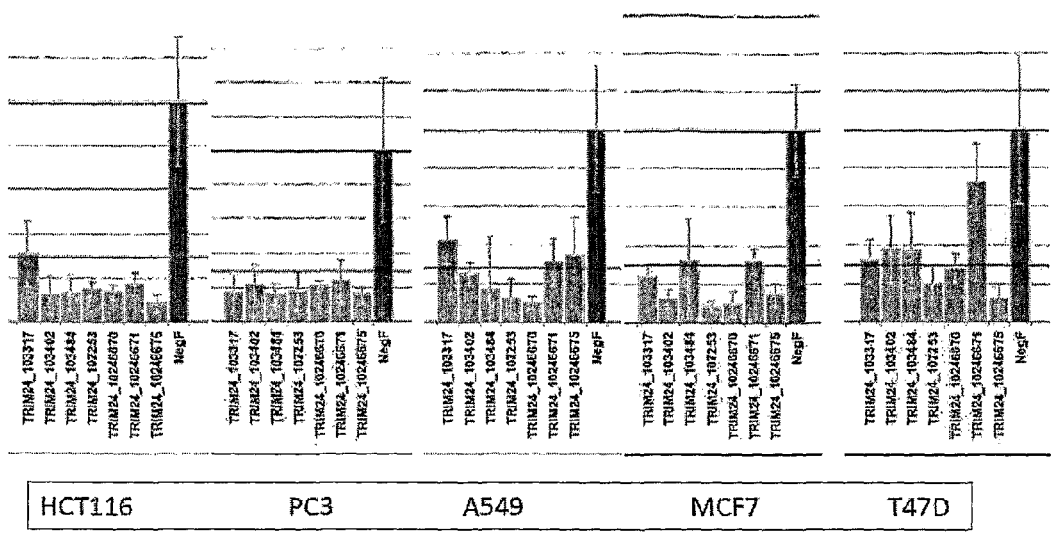
FIG. 11 shows graphical representations of TRIM24 knockdown in HCT116, PC3, A549, MCF7 and T47D cancer cell lines transfected singly with the siRNA sequences described in FIG. 10. The upper dark line represents the 100% expression level in un-transfected cells, the lower dark line represents the 70% inhibition level.

The data are expressed graphically in FIG. 11. The upper dark line represents the 100% expression level in un-transfected cells, the lower dark line represents the 70% inhibition level. The results show that all 7 siRNAs resulted in significantly decreased levels of TRIM24 transcript although some variation was observed for different sequences in different cell lines.

Following successful establishment of the optimal transfection conditions and siRNA sequences for knockdown of TRIM24 transcript levels, the transfections were repeated and the numbers of cell nuclei assessed using Hoechst staining followed by automated microscopy acquisition and automated image analysis.

Briefly, on day 4 post-transfection cells were fixed with paraformaldehyde and retained overnight at 4° C. On day 5, the cells were washed, incubated with Hoechst stain (to detect nuclei), and stored at 4° C. in the dark following a final wash. Automated image acquisition was performed using the ImageXpress Micro system from Molecular Devices, using 4 sites per well at 10× magnification and binning. Image analysis was performed using Cellenger from Definiens, adopting the parameters to specific cell types and staining densities.

Figure 12:
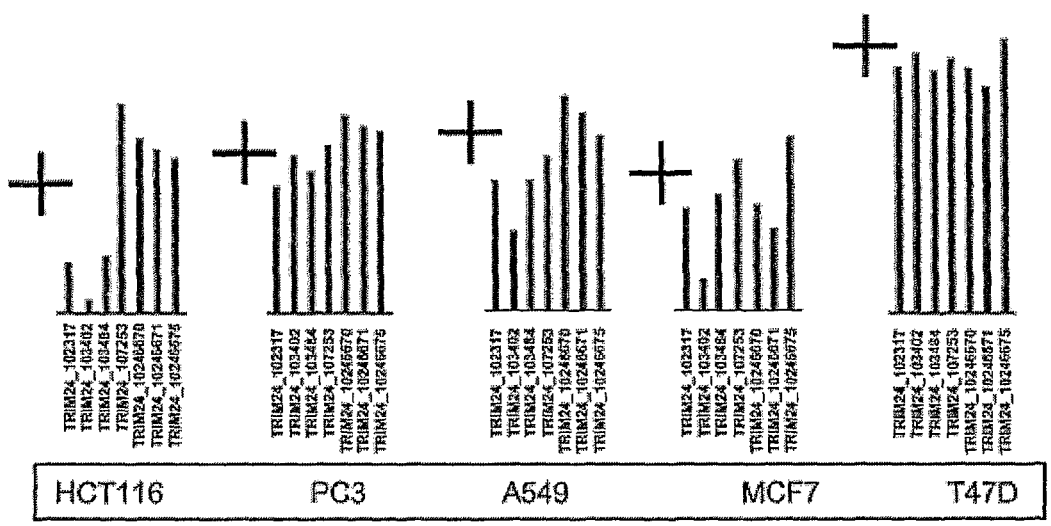
FIG. 12 further shows a graphical representations of TRIM24 knockdown in HCT116, PC3, A549, MCF7 and T47D cancer cell lines transfected singly with the siRNA sequences described in FIG. 10 but where the data has been normalized to the levels for the negative control i.e. non-specific siRNA and presented as % of the NegF value shown in FIG. 11. The figure displays information regarding cell proliferation in the respective cell lines. The large cross on the figures represents the 100% level.

Data were normalized to the levels for the negative i.e. non-specific siRNA and presented as % of this in FIG. 12. The large cross on the figures represents the 100% level. The results demonstrate that knockdown of TRIM24 leads to significant decreases in cell numbers of HCT116, A549 and MCF7 cells. There was no effect of TRIM24 knockdown in PC3 and T47D cells, despite comparable levels of target gene expression across the different cell types.

It is significant that TRIM24 knockdown only led to decreases in cell number in the HCT116, A549 and MCF7 cells, as these cell lines all express wildtype p53. The other two cell lines express no/mutant p53 (PC3) or mutant p53 (T47D). These data are consistent with the effects of TRIM24 being dependent on its interaction with p53.

Following successful establishment of the optimal transfection conditions and siRNA sequences for knockdown of TRIM24 transcript levels, the transfections were repeated and the degree of cellular confluency assessed using anti-tubulin staining followed by automated microscopy acquisition and automated image analysis.

Briefly, on day 4 post-transfection cells were fixed with paraformaldehyde, non-specific sites were blocked and the samples were incubated with primary antibody against tubulin overnight at 4° C. On day 5, the cells were washed, incubated with sFITC-linked secondary antibody and stored at 4° C. in the dark following a final wash. Automated image acquisition was performed using the ImageXpress Micro system from Molecular Devices, using 4 sites per well at 10× magnification and binning. Image analysis was performed using Cellenger from Definiens, adopting the parameters to specific cell types and staining densities.

Data were normalized to the levels for the negative i.e. non-specific siRNA and presented as % of this in FIG. 12. The large cross on the figures represents the 100% level. The degree of confluence was calculated as:

Degree of well bottom habitation; formally:

$$\{[\text{number of FITC pixels}]+[\text{number of (all) nuclei pixels}]/361920\}*100\%$$

Figure 13:
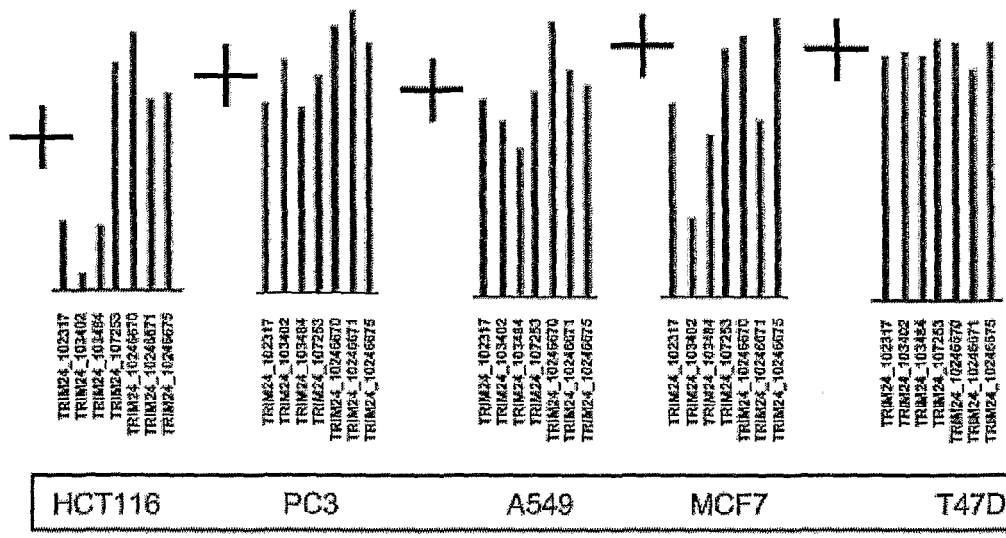
FIG. 13 further shows a graphical representation of TRIM24 knockdown in HCT116, PC3, A549, MCF7 and 147D cancer cell lines transfected singly with the siRNA sequences described in FIG. 10 but where the degree of cellular confluency has been assessed in the respective cell lines. Data were normalized to the levels for the negative control i.e. non-specific siRNA and presented as % of this. The large cross on the figures represents the 100% level.

The results shown in FIG. 13 demonstrate that knockdown of TRIM24 leads to significant decreases in cell numbers of HCT116, MCF7 and to a lesser extent A549 cells. There was no effect of TRIM24 knockdown in PC3 and T47D cells, despite comparable levels of target gene expression across the different cell types.

It is significant that TRIM24 knockdown only led to decreases in cell number in the HCT116, A549 and MCF7 cells, as these cell lines all express wildtype p53. The other two cell lines express no/mutant p53 (PC3) or mutant p53 (T47D).

These data are consistent with the effects of TRIM24 being dependent on its interaction with p53.

shRNA Knock Down of TRIM24 in Human Breast Cancer Cells

Figure 14:
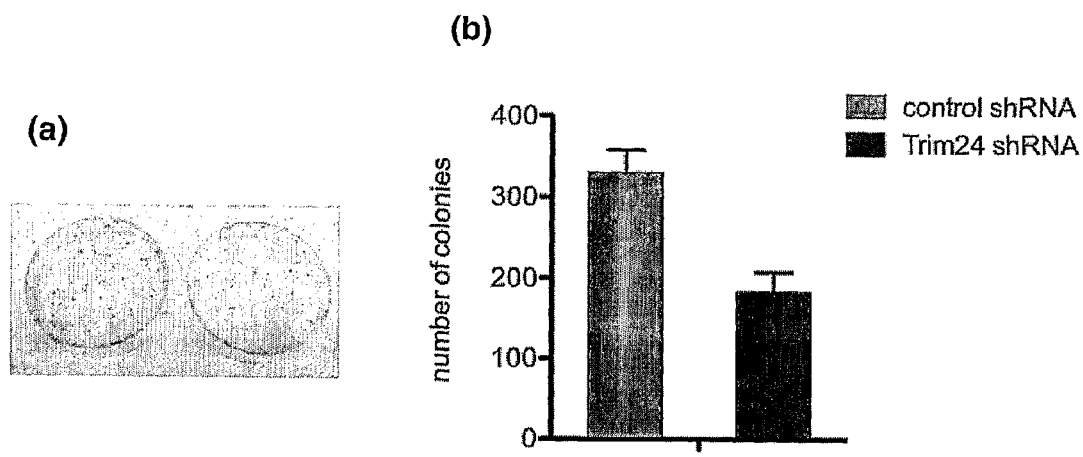
FIG. 14 (*a*) shows a photograph of cell culture dishes in which a MCF7 breast cancer cell line has been transfected with an shRNA-expressing plasmid targeting TRIM24 expression. The left hand Petri dish shows colony formation where cells have been transfected with control shRNA; the right hand Petri dish shows colony formation where cells have been transfected with an shRNA-expressing plasmid targeting TRIM24 expression. (b) The results of 72 hour growth and assessment by a colony formation assay are shown and expressed graphically.

TRIM24 was depleted by stable transfection of shRNA-expressing plasmid targeting TRIM24 in the MCF7 breast cancer cell line. The results of 72 hour growth and assessment by a colony formation assay are shown and expressed graphically in FIG. 14. These data demonstrate that knockdown of TRIM24 leads to substantially decreased colony formation in MCF7 breast cancer cell lines. This is consistent with the data on cell proliferation shown in FIGS. 12 and 13.

siRNA Knock Down of TRIM24 in Pluripotent Cells

Figure 15:
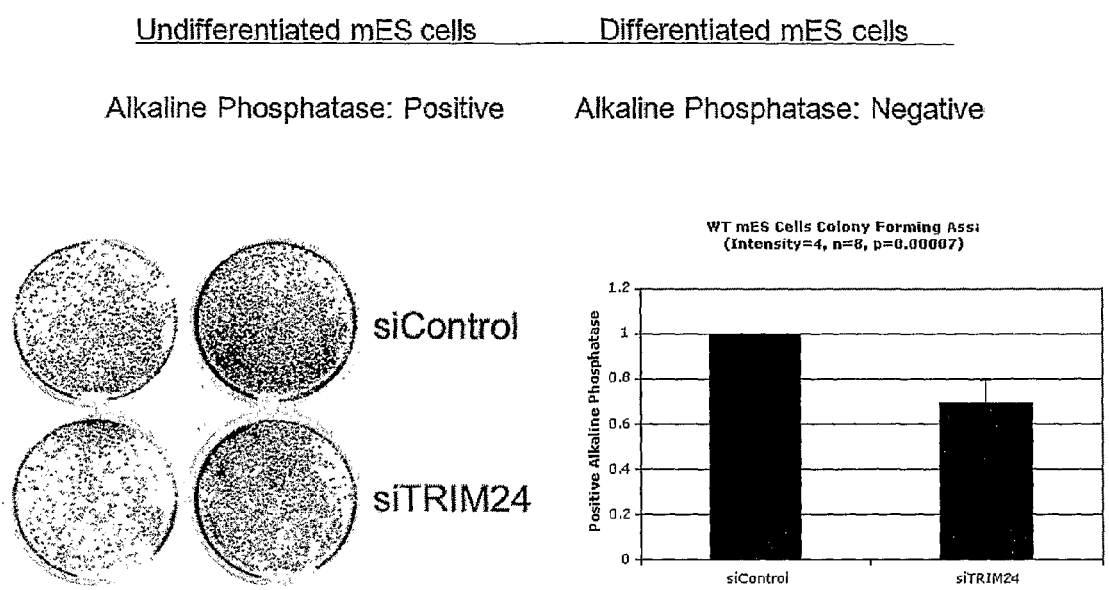
FIG. 15 (left hand panel) shows a photograph of cell culture dishes in which mouse ES cells were plated in equal numbers and levels of alkaline phosphatase activity quantified 48 hours later. Transient depletion of TRIM24 by siRNA induced spontaneous differentiation of mES cells, as compared to control siRNA treated cells. Graphical representation of the data are shown in the right hand panel.

Mouse ES (mES) cells were grown in the presence of LIF to inhibit differentiation. Cells were plated in equal numbers and levels of alkaline phosphatase activity quantified 48 hours later. Transient depletion of TRIM24 by siRNA induced spontaneous differentiation of mES cells, as compared to control siRNA treated cells (FIG. 15). These data demonstrate a significant role for TRIM24 in the maintenance of pluripotency in mES cells. Such an effect is also significant in the stem cell model of cancer. If ablation of TRIM24 in cancer stem cells has the same effect as in mES cells, inhibition of this protein will provide a useful therapeutic intervention by promoting cancer stem cell differentiation at the expense of cancer stem cell self-renewal.

Online Resources:

Gene Expression Omnibus (GEO) at NCBI:

http://www.ncbi.nlm.nih.gov/geo/

Oncomine: http://www.oncomine.org/main/index.jsp

Biocarta pathways: http://www.biocarta.com/genes/index.asp

ENTREZ GENE: http://www.ncbi.nlm.nih.gov/entrez/query.fcgi?db=gene

ENTREZ Homologene:

http://www.ncbi.nlm.nih.gov/entrez/query.fcgi?db=homologene

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

The invention claimed is:

1. A method of identifying a modulator of TRIM24 (TIF-1 a) activity comprising:
   (i) exposing a TRIM24 polypeptide, or a cell expressing such a peptide, to a plurality of candidate compounds;
   (ii) determining whether one or more of the candidate compounds modulate the E3 ligase activity of TRIM24 or its binding to p53; and
   (iii) providing a compound determined to modulate the E3 ligase activity of TRIM24 or its binding to p53.

2. The method of claim 1, wherein the candidate compounds are tested for their effect on E3 ligase activity of TRIM24.

3. The method of claim 2, wherein the E3 ligase activity is a ubiquitylation/sumoylation activity.

4. The method of claim 1, wherein the TRIM24 activity is an E3 ligase activity and the method comprises:
   assessing the E3 ligase activity of a TRIM24 polypeptide or a fragment thereof in an assay to determine a base-level E3 ligase activity for the TRIM24 polypeptide or fragment thereof;
   contacting the TRIM24 polypeptide or fragment thereof with the one or more candidate compounds;
   assessing the E3 ligase activity of the TRIM24 polypeptide or fragment thereof in an E3 ligase assay in the presence of the one or more candidate compounds to determine a test E3 ligase activity for the TRIM24 polypeptide or fragment thereof in the presence of the one or more candidate compounds; and
   determining whether the base-level E3 ligase activity for the TRIM24 polypeptide or fragment thereof is different to the test E3 ligase activity; and
   where the base-level E3 ligase activity is different to the test E3 ligase activity for the TRIM24 polypeptide or fragment thereof in the presence of the one or more candidate compounds, identifying that compound as a modulator of TRIM24 activity.

5. The method of claim 4, wherein the E3 ligase activity is determined with respect to the ability to conjugate a ubiquitin or ubiquitin-like protein to a predetermined substrate.

6. The method of claim 5, wherein the ubiquitin-like protein comprises a Small Ubiquitin-like Modifier (SUMO) protein.

7. The method of claim 5, wherein the substrate comprises p53 polypeptide or a fragment or derivative of p53.

* * * * *